US011858946B2

(12) United States Patent
Hergenrother et al.

(10) Patent No.: US 11,858,946 B2
(45) Date of Patent: *Jan. 2, 2024

(54) SMALL MOLECULES ACTIVE AGAINST GRAM-NEGATIVE BACTERIA

(71) Applicant: The Board of Trustees of the University of Illinois, Urbana, IL (US)

(72) Inventors: Paul J. Hergenrother, Champaign, IL (US); Michelle Richter, Urbana, IL (US); Andrew Riley, Savoy, IL (US); Bryon S. Drown, Champaign, IL (US); Martin Chavez, La Porte, IN (US); Sarah Tasker, Urbana, IL (US); Alfredo Garcia, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 187 days.

This patent is subject to a terminal disclaimer.

(21) Appl. No.: 17/306,008

(22) Filed: May 3, 2021

(65) Prior Publication Data

US 2022/0112203 A1    Apr. 14, 2022

Related U.S. Application Data

(63) Continuation of application No. 16/084,117, filed as application No. PCT/US2017/022029 on Mar. 13, 2017, now Pat. No. 10,995,097.

(60) Provisional application No. 62/327,092, filed on Apr. 25, 2016, provisional application No. 62/306,838, filed on Mar. 11, 2016.

(51) Int. Cl.

| | |
|---|---|
| *C07D 413/14* | (2006.01) |
| *C07D 413/04* | (2006.01) |
| *C07D 413/10* | (2006.01) |
| *C07D 471/04* | (2006.01) |
| *C07D 471/14* | (2006.01) |
| *C07D 498/04* | (2006.01) |
| *A61P 31/04* | (2006.01) |
| *C07D 413/12* | (2006.01) |
| *C07D 491/052* | (2006.01) |
| *C07D 407/06* | (2006.01) |
| *C07D 407/12* | (2006.01) |
| *C07C 225/20* | (2006.01) |
| *C07D 471/20* | (2006.01) |
| *C07D 263/20* | (2006.01) |
| *C07J 1/00* | (2006.01) |
| *C07J 13/00* | (2006.01) |
| *C07J 21/00* | (2006.01) |
| *C07J 41/00* | (2006.01) |
| *C07J 43/00* | (2006.01) |
| *C07J 73/00* | (2006.01) |
| *C07D 417/12* | (2006.01) |

(52) U.S. Cl.
CPC .......... *C07D 491/052* (2013.01); *A61P 31/04* (2018.01); *C07C 225/20* (2013.01); *C07D 263/20* (2013.01); *C07D 407/06* (2013.01); *C07D 407/12* (2013.01); *C07D 413/04* (2013.01); *C07D 413/10* (2013.01); *C07D 413/12* (2013.01); *C07D 413/14* (2013.01); *C07D 417/12* (2013.01); *C07D 471/04* (2013.01); *C07D 471/14* (2013.01); *C07D 471/20* (2013.01); *C07D 498/04* (2013.01); *C07J 1/0011* (2013.01); *C07J 13/007* (2013.01); *C07J 21/008* (2013.01); *C07J 41/0011* (2013.01); *C07J 41/0055* (2013.01); *C07J 41/0088* (2013.01); *C07J 43/003* (2013.01); *C07J 73/00* (2013.01); *C07C 2603/82* (2017.05)

(58) Field of Classification Search
CPC .. C07D 413/04; C07D 413/10; C07D 413/12; C07D 413/14; C07D 417/12; C07D 471/04; C07D 471/14; C07D 498/04; A61P 31/04

See application file for complete search history.

(56) References Cited

U.S. PATENT DOCUMENTS

| | | | |
|---|---|---|---|
| 5,668,286 | A | 9/1997 | Yamada et al. |
| 5,700,799 | A | 12/1997 | Hutchinson et al. |
| 6,686,363 | B2 | 2/2004 | Fukuda |
| 9,611,266 | B2 | 4/2017 | Hergenrother et al. |
| 10,995,097 | B2 * | 5/2021 | Hergenrother ......... C07J 43/003 |
| 11,274,106 | B2 * | 3/2022 | Hergenrother ....... C07D 498/16 |
| 2003/0013737 | A1 | 1/2003 | Gordeev et al. |
| 2003/0225107 | A1 | 12/2003 | Fukuda |
| 2004/0162279 | A1 | 8/2004 | Barbachyn et al. |
| 2005/0004174 | A1 | 1/2005 | Gordeev et al. |
| 2005/0070526 | A1 | 3/2005 | Agarwal et al. |
| 2005/0118624 | A1 | 6/2005 | Ma et al. |

(Continued)

FOREIGN PATENT DOCUMENTS

| | | |
|---|---|---|
| EP | 2130831 A1 | 12/2009 |
| EP | 2500022 B1 | 12/2015 |

(Continued)

OTHER PUBLICATIONS

Forbis; Journal of the American Chemical Society 1973, 95, 5003-5013. (Year: 1973).*

(Continued)

*Primary Examiner* — Daniel R Carcanague
(74) *Attorney, Agent, or Firm* — Haukaas Fortius PLLC; Michael Haukaas

(57) ABSTRACT

Disclosed are novel compounds that accumulate in Gram-negative bacteria. Also disclosed are method of antimicrobial treatment using the compounds.

9 Claims, 22 Drawing Sheets

(56) References Cited

U.S. PATENT DOCUMENTS

| | | | |
|---|---|---|---|
| 2007/0167414 | A1 | 7/2007 | Agarwal et al. |
| 2010/0069441 | A1 | 3/2010 | Gordeev et al. |
| 2011/0245258 | A1 | 10/2011 | Jain et al. |
| 2012/0157434 | A1 | 6/2012 | Gordeev et al. |
| 2012/0258980 | A1 | 10/2012 | Igarashi et al. |
| 2015/0322530 | A1 | 11/2015 | Orsulic et al. |
| 2016/0257651 | A1 | 9/2016 | Hiramatsu et al. |
| 2017/0096436 | A1 | 4/2017 | Hergenrother et al. |

FOREIGN PATENT DOCUMENTS

| | | | |
|---|---|---|---|
| JP | 2004203809 | A | 7/2004 |
| WO | 1995007271 | A1 | 3/1995 |
| WO | 03093247 | A2 | 11/2003 |
| WO | 2006022794 | A1 | 3/2006 |
| WO | 2009001192 | A3 | 5/2010 |
| WO | 2017017631 | A2 | 2/2017 |
| WO | 2017156519 | A1 | 9/2017 |

OTHER PUBLICATIONS

Nakamura; "The development of deoxynybomycins as potent and selective antibiotics against fluoroquinolone resistant bacteria". 2015. University of Illinois at Urbana-Champaign, Masters Dissertation. (Year: 2015).*

Parkinson; "Deoxynyboquinones as NQO1-targeted anticancer compounds and deoxynybomycins as potent and selective antibiotics". 2015. University of Illinois at Urbana-Champaign, PhD Dissertation. (Year: 2015).*

Pattelli; "Targeting Drug Resistant Bacteria: Deoxynybomycin and its Derivatives". Presented at University of Illinois at Urbana-Champaign Undergraduate Research Symposium, 2016. Downloaded Apr. 11, 2023 from https://www.ideals.illinois.edu/items/92573 (Year: 2016).*

Richter; "Development of predictive guidelines for compound accumulation in gram-negative bacteria". Oct. 4, 2017. University of Illinois at Urbana-Champaign, PhD Dissertation. (Year: 2017).*

Bair et al., "Chemistry and Biology of Deoxynyboquinone, a Potent Inducer of Cancer Cell Death," J. Am. Chem. Soc., 132(15):5469-5478, Mar. 2010.

Bisacchi et al., "A "Double-Edged" Scaffold: Antitumor Power within the Antibacterial Quinolone," Curr Med Chem., 23(6):520-577, Feb. 2016.

Chemical Abstracts STN Registry Database, Record for RN 123601-72-9, Nov. 1989.

Egawa et al., "Deoxynybomycin is a Selective Anti-Tumor Agent Inducing Apoptosis and Inhibiting Topoisomerase I," Biol Pharm Bull., 23(9):1036-1040, Sep. 2000.

Gleave et al., "Synthesis and Antibacterial Activity of [6,5, 5] and [6,6, 5] Tricyclic Fused Oxazolidinones," Bioorg Med Chem Lett., 8(10):1231-1236, May 1998.

Hiramatsu et al., "Curing Bacteria of Antibiotic Resistance: Reverse Antibiotics, A Novel Class of Antibiotics in Nature," Int J Antimicrob Agents, 39(6):478-485, Jun. 2012.

International Search Report and Written Opinion of the ISA/US dated Sep. 14, 2018 in International Application No. PCT/US2018/387458; 6pgs.

International Search Report and Written Opinion of the ISA/US dated Jul. 18, 2017 in International Application No. PCT/US2017/022029 ; 14pgs.

Li et al., "Synthesis and Antibacterial Activity of (S)-5-Acetyl Aminomethyl-3-[(4- Substituted-Aminomethyl}phenyl]-2-Oxazolidinone Derivatives," Yao Xue Xue Bao, 41(5):418-425, May 2006.

Naganawa et al., "Deoxynybomycin from a *Streptomyces*," J Antibiot. (Tokyo), 23(7):365-368, Jul. 1970.

Parkinson et al., "Deoxynybomycins Inhibit Mutant DNA Gyrase and Rescue Mice Infected with Fluoroquinolone-Resistant Bacteria," Nature Comm., 6(2947):1-9, 2015.

Poel et al., "Antibacterial Oxazolidinones Possessing a Novel C-5 Side Chain. (5R)-trans-3-[3-Fluoro-4-(1-oxotetrahydrothiopyran-4-yl)phenyl]-2-oxooxazolidine-5-carboxylic Acid Amide (PF-00422602), a New Lead Compound," J Med Chem., 50(24):5886-5889, Nov. 2007.

Richter et al., "Predictive Compound Accumulation Rules Yield a Broad-Spectrum Antibiotic," Nature, 545:299-304, May 2017.

Richter et al., "Predictive Rules for Compound Accumulation Yield a Broad-Spectrum Antibiotic," Nature, 545(7654):299-304, May 2017.

Zhou et al., "Design at the Atomic Level: Generation of Novel Hybrid Biaryloxazolidinones as Promising New Antibiotics," Bioorg Med Chem Lett., 18(23):6179-6183, Dec. 2008.

* cited by examiner

TABLE 1

| SPECIES | STRAIN | 6DNM<br>NO PRIMARY AMINE<br>RB = 0<br>GLOB = 0.04<br>ClogD7.4 = 1.22<br>MW = 296<br>ACCUM = 298 | 6DNM-NH3<br>PRIMARY AMINE<br>RB = 1<br>GLOB = 0.09<br>ClogD7.4 = -0.87<br>MW = 325<br>ACCUM = 1114 | 6DNM-amide<br>NO PRIMARY AMINE<br>RB = 1<br>GLOB = 0.13<br>ClogD7.4 = 0.30<br>MW = 367<br>ACCUM = 134 | 6DNM-acid<br>NO PRIMARY AMINE<br>RB = 1<br>GLOB = 0.07<br>ClogD7.4 = -2.32<br>MW = 354<br>ACCUM = 111 | CIPRO |
|---|---|---|---|---|---|---|
| S. AUREUS (GRAM-POSITIVE) | ATCC 29213 | 1 | 2 | 32 | >32 | 0.125 |
| | CLINICAL ISOLATE: NRS3 | 0.06 | 0.03 | 0.5 | 16 | 8 |
| E. COLI (GRAM-NEGATIVE) | MG1655 | >32 | 2 | >32 | >32 | 0.02 |
| | CLINICAL ISOLATES: | | | | | |
| | ELZ4017 | >32 | 0.5 | >32 | >32 | 0.004 |
| | ELZ4045 | >32 | 0.5 | >32 | >32 | 0.008 |
| | ELZ4042 | >32 | 0.5 | >32 | >32 | 0.03 |
| | ELZ4346 | >32 | 2 | >32 | >32 | 64 |
| | ELZ4004 | >32 | 4 | >32 | >32 | 6 |
| | ELZ4081 | >32 | 4 | >32 | >32 | 16 |
| | ELZ4277 | >32 | 8 | >32 | >32 | 32 |
| | ELZ4072 | >32 | 8 | >32 | >32 | >64 |
| | ELZ4239 | >32 | 16 | >32 | >32 | 64 |
| | ELZ4139 | >32 | 16 | >32 | >32 | >64 |
| | BAA-2452 | >32 | 4 | >32 | >32 | >64 |

GRAM-NEGATIVE (CONT.)

| | | | | | | |
|---|---|---|---|---|---|---|
| A. BAUMANNII | ATCC 19606 | 16 | 4 | >32 | >32 | 0.5 |
| | CLINICAL ISOLATES: | | | | | |
| | KB304 | >32 | 2 | >32 | >32 | 32 |
| | KB349 | >32 | 2 | >32 | >32 | 16 |
| | WO22 | 16 | 2 | >32 | >32 | 16 |
| | BD335 | 16 | 8 | >32 | >32 | 64 |
| | IF101 | >32 | 16 | >32 | >32 | 64 |
| K. PNEUMONIAE | ATCC 27736 | >32 | 1 | >32 | >32 | <0.03 |
| | CLINICAL ISOLATES: | | | | | |
| | 4-38 | >32 | 4 | >32 | >32 | 1 |
| | 6-73 | >32 | 8 | >32 | >32 | >64 |
| E. CLOACAE | ATCC 29893 | 32 | 0.5 | >32 | >32 | <0.03 |
| | CLINICAL ISOLATES: | | | | | |
| | 1-60 | 32 | 2 | >32 | >32 | 1 |
| | 3-46 | >32 | 4 | >32 | >32 | 16 |
| P. AERUGINOSA | PAO1 | >32 | 16 | >32 | >32 | 0.25 |

SMALL MOLECULES ACTIVE AGAINST GRAM-NEGATIVE BACTERIA

RELATED APPLICATIONS

This application claims priority to U.S. application Ser. No. 16/084,117 filed Sep. 11, 2018, now U.S. Pat. No. 10,995,097, issued May 4, 2021, which is a National Stage filing under 35 U.S.C. § 371 of International Application No. PCT/US2017/022029 filed Mar. 13, 2017, which claims priority under 35 U.S.C. § 119(e) to U.S. Provisional Patent Application Nos. 62/306,838 filed Mar. 11, 2016 and 62/327,092 filed Apr. 25, 2016, which applications are hereby incorporated by reference.

BACKGROUND

Drug-resistant bacteria are a major public health concern, with Gram-negative bacteria particularly troubling as they are insensitive to many commonly used antibiotics. Exacerbating this problem is the fact that a new class of antibiotics active against Gram-negative bacteria has not been introduced into the clinic since the quinolones in 1968. This void in discovery is not due to a lack of effort; as one example, in 2007 GlaxoSmithKline reported screening ~500,000 synthetic compounds for whole cell activity against *Escherichia coli*, but no tractable hits were identified.

The difficulty of killing Gram-negative pathogens is largely attributed to the structure of their outer membranes. Gram-negative bacteria possess two cellular membranes, with the outer membrane allowing only very slow passive diffusion of small molecules. Once inside the cell, small molecules are susceptible to efflux pumps; thus, in order to accumulate in Gram-negatives, small molecules must cross the outer membrane at a faster rate than they are pumped out. In order to accumulate to a level sufficient for activity, small molecules typically must cross the outer-membrane via channel proteins called porins, which are narrow β-barrels lined with charged amino acids that serve as selective gateways to entry for many small molecule antibiotics. For many Gram-negative species, antibiotics enter through general porins such as OmpF, the prototypical porin of *E. coli*. Although general porins are wider than typical substrate specific channels, most contain a relatively narrow constriction zone, limiting the size of small molecules capable of diffusing through. For example, the constriction zone of OmpF is approximately 7×11 Å, which is believed to restrict passive diffusion of small molecules to an estimated 600 Da.

Central to the problem of Gram-negative antibiotic discovery is a limited understanding of the physicochemical properties that enable small molecule accumulation in Gram-negative bacteria, with current knowledge based largely on retrospective analyses of known antibiotics, and free energy calculations of small molecule permeation across the outer membrane. In 2008 O'Shea and Moser reported that antibiotics effective against Gram-negative pathogens almost always have a molecular weight (MW) less than 600 Da and tend to be very polar as measured by $ClogD_{7.4}$, observations consistent with porin architecture. Retrospective studies by others have re-enforced these observations that Gram-negative active compounds tend to be small and highly polar. However, there are a number of antibiotics that meet these polarity and size criteria but are inactive against Gram-negative species, suggesting these properties do not fully encompass the determinants for small molecule accumulation. Additionally, retrospective analyses are highly skewed by the over-representation of certain drug classes. For example, an analysis by AstraZeneca showed that carboxylic acids are present on up to 40% of Gram-negative active compounds in their collection; however, these carboxylic-acid-containing compounds are almost exclusively β-lactams. While a handful of compound accumulation studies in whole cells have been performed, broad conclusions cannot be drawn from these small data sets (10-20 compounds and all within a single structural class). Perhaps most importantly, the canonical view about the importance of $ClogD_{7.4}$ and MW for Gram-negative activity has not led to general strategies to convert Gram-positive-only compounds into broad-spectrum antibiotics. The seminal observation over 50 years ago that derivatizing penicillin G into ampicillin results in broad-spectrum activity has not been generalizable, and important classes of experimental therapeutics and FDA-approved antibiotics have coverage only against Gram-positive organisms despite intensive derivatization efforts.

Therefore, there exists a need for novel Gram-negative antibiotics and methods of use thereof. There also exists a need for improved understanding of physicochemical properties that enable small molecule accumulation in Gram-negative bacteria.

SUMMARY

In one aspect, provided herein are novel compounds of any one of formulas (I), (II), (III), (IV), (V), (VI), (VII), (VIII), or (IX), or a pharmaceutically acceptable salt thereof.

In another aspect, provided herein is a method of antimicrobial treatment, comprising, administering to a subject in need thereof a therapeutically effective amount of a compound of any one of formulas (I), (II), (III), (IV), (V), (VI), (VII), (VIII), or (IX), or a pharmaceutically acceptable salt thereof, thereby killing or inhibiting the growth of at least a portion of a plurality of microorganisms in the subject.

In another aspect, provided herein is a method of antimicrobial treatment, comprising:

providing a sample comprising a plurality of microorganisms;

contacting the sample with a compound disclosed herein;

thereby killing or inhibiting the growth of at least a portion of the plurality of microorganisms in the sample.

BRIEF DESCRIPTION OF THE FIGURES

FIG. 19 tabulates structures, parameters, and antibacterial evaluation of exemplary compounds of formula (IX).

DETAILED DESCRIPTION OF THE INVENTION

Overview

Figure 1:
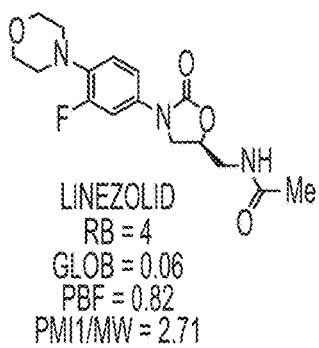
FIG. 1 depicts exemplary compounds that serve as scaffolds for the compounds disclosed herein.
Figure 1:
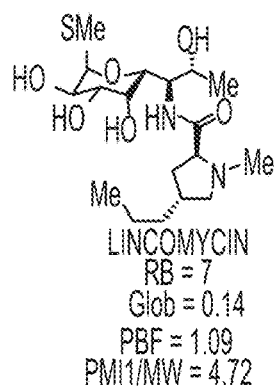
Figure 1:
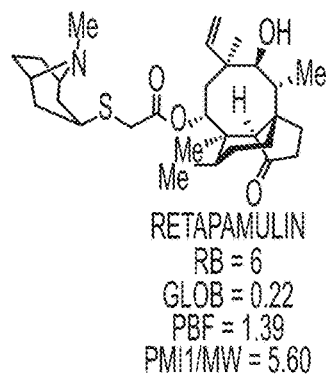
Figure 1:
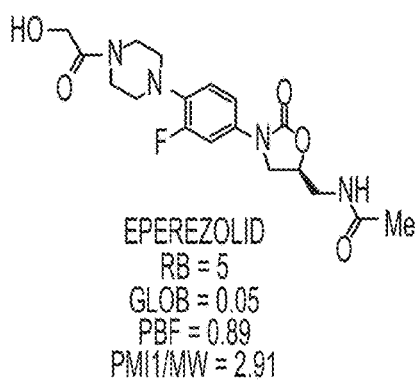
Figure 1:
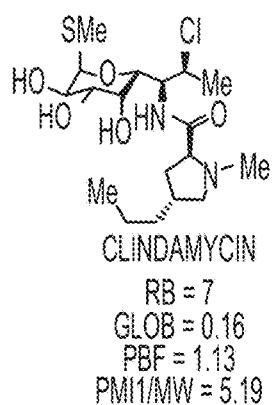
Figure 1:
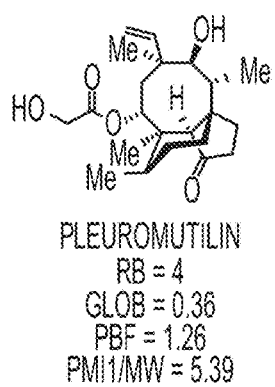
Figure 1:
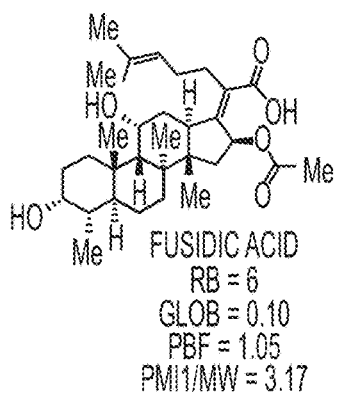
Figure 1:
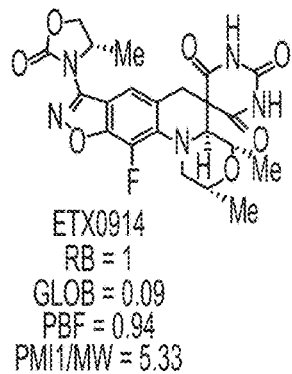
Figure 1:
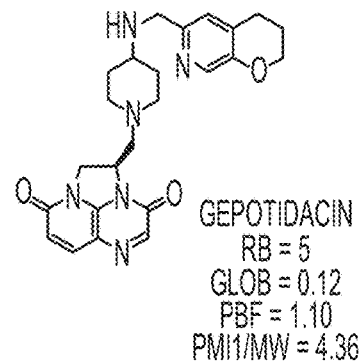
Figure 1:
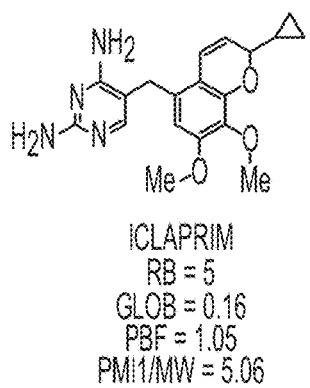

The canonical view about the importance of highly polar molecules with a molecular weight less than 600 Da for Gram-negative activity has not led to general strategies to convert Gram-positive-only compounds into broad-spectrum antibiotics. The seminal observation over 50 years ago that derivatizing penicillin G into ampicillin results in broad-spectrum activity has not been generalizable, and important classes of experimental therapeutics and FDA-approved antibiotics have coverage only against Gram-positive organisms despite intensive derivatization efforts.

A systematic analysis of the accumulation of an unbiased and structurally diverse set of small molecules in Gram-negative bacteria has not been previously reported. According to the present disclosure, a diverse set of 100 compounds was assembled, and their capacity to accumulate in *E. coli*, and by extension other Gram-negative bacteria, was quantified. As there are many variables affecting small molecule accumulation (e.g., multiple porins, efflux pumps, and varying lipopolysaccharides of the cellular envelope), model systems were not utilized, and instead compounds were assessed in accumulation assays using whole cells. From these experiments, and from follow-on structure-activity relationship (SAR) studies and computational analyses, predictive guidelines of small molecule accumulation in Gram-negative bacteria have been developed.

Described herein are novel compounds and methods of use thereof as antibiotics.

In some embodiments, the compounds disclosed herein comprise an ionizable nitrogen atom. In some embodiments, the compounds disclosed herein comprise a terminal —N(R$^5$)$_m$ moiety, wherein R$^5$ is independently selected from the group consisting of hydrogen, (C$_1$-C$_6$)alkyl, cycloalkyl, heterocycloalkyl, aryl, heteroaryl, aralkyl, and heteroaralkyl, and m is is 2 or 3. In some embodiments, —N(R$^5$)$_m$ is —NH$_2$, —NHMe, —NHEt, —NMe$_2$, —NEt$_2$, or —NMe(Et); or a protonated form (quaternary amine) thereof. In some embodiments, —N(R$^5$)$_m$ is —NH$_3^+$, —NH$_2$Me$^+$, or —NHMe$_2^+$. In some embodiments, the compounds disclosed herein comprise a terminal —NH$_2$, a primary amine. In some embodiments, the compounds disclosed herein comprise a quaternary amine. In some embodiments, the compounds disclosed herein comprise a terminal —NH$_3^+$.

In some embodiments, the compounds disclosed herein have at least one hydrophobic region. In some embodiments, the compounds disclosed herein are amphiphilic. In some embodiments, the compounds disclosed herein have at least one hydrophobic region and at least one hydrophilic region. In some embodiments, the compounds disclosed herein have an amphiphilic moment greater than 1, greater than 2, greater than 3, greater than 4, greater than 5, greater than 6, greater than 7, greater than 8, greater than 9, or greater than 10. In some embodiments, the compounds disclosed herein have an amphiphilic moment between 1 and 20.

In some embodiments, the amphiphilic moment is between about 2 and about 10 or between about 2 and about 7. In some embodiments, the amphiphilic moment is selected from the group consisting of about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, and about 9.0.

In some embodiments, the compounds disclosed herein are rigid. In some embodiments, the compounds disclosed herein are less flexible. In some embodiments, the compounds disclosed herein have 15 or fewer rotatable bonds (RBs). In some embodiments, the compounds disclosed herein have 12 or fewer rotatable bonds, 11 or fewer rotatable bonds, 10 or fewer rotatable bonds, 9 or fewer rotatable bonds, 8 or fewer rotatable bonds, 7 or fewer rotatable bonds, 6 or fewer rotatable bonds, 5 or fewer rotatable bonds, 4 or fewer rotatable bonds, 3 or fewer rotatable bonds, 2 or fewer rotatable bonds, or 1 or fewer rotatable bonds. In some embodiments, the number of rotatable bonds is selected from the group consisting of 0, 1, 2, 3, 4, 5, 6, 7, 8, 9, 10, 11, and 12. In some embodiments, the number of rotatable bonds is selected from the group consisting of 0, 1, 2, 3, 4, and 5. In some embodiments, the compounds disclosed herein have RB of 7 or less, 6 or less, 5 or less, 4 or less, 3 or less, or 2 or less.

In some embodiments, the compounds disclosed herein have low 3-dimensionality. In some embodiments, the compounds disclosed herein comprise a moiety with a planar feature, such as a phenyl or heteroaromatic ring. In some embodiments, the compounds disclosed herein have low globularity. In some embodiments, the compounds disclosed herein have a globularity (Glob) less than 0.8, less than 0.75, less than 0.7, less than 0.65, less than 0.6, less than 0.55, less than 0.5, less than 0.45, less than 0.4, less than 0.3, less than 0.25, less than 0.2, less than 0.15, or less than 0.1. In some embodiments, the compounds disclosed herein have Glob of 0.4 or less, 0.3 or less, 0.2 or less, or 0.1 or less. In some embodiments, the compounds disclosed herein have Glob of 0.42 or less, 0.4 or less, 0.38 or less, 0.36 or less, 0.34 or less, 0.32 or less, 0.3 or less, 0.28 or less, 0.26 or less, 0.24 or less, 0.22 or less, 0.20 or less, 0.18 or less, 0.16 or less, 0.14 or less, 0.12 or less, 0.1 or less, 0.08 or less, 0.06 or less, 0.04 or less, or 0.02 or less. In some embodiments, the compounds disclosed herein have a globularity between 0 and 0.7. In some embodiments, the globularity is between about 0 and about 0.6, between about 0 and about 0.5, between about 0 and about 0.4, or between about 0 and about 0.3. In some embodiments, the globularity is selected from the group consisting of about 0.01, about 0.02, about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, about 0.30, about 0.31, about 0.32, about 0.33, about 0.34, and about 0.35.

In some embodiments, the compounds disclosed herein have a planar best fit (PBF) between about 0.2 and about 2, between about 0.4 and about 1.8, between about 0.5 and about 1.7, between about 0.6 and about 1.6, between about 0.8 and about 1.5, or between about 0.9 and about 1.4. In some embodiments, the PBF is selected from the group consisting of about 0.45, about 0.5, about 0.55, about 0.6, about 0.65, about 0.7, about 0.75, about 0.8, about 0.85, about 0.87, about 0.89, about 0.9, about 0.92, about 0.94, about 0.96, about 0.98, about 1.0, about 1.02, about 1.04, about 1.06, about 1.08, about 1.1, about 1.12, about 1.14, about 1.16, about 1.18, about 1.2, about 1.22, about 1.24, about 1.26, about 1.28, about 1.3, about 1.32, about 1.34, about 1.36, about 1.38, about 1.4, about 1.5, and about 1.5. In some embodiments, the PBF is about 0.89.

In some embodiments, the compounds disclosed herein have a ratio of principal moment of inertia to molecular weight (PMI1/MW) between about 1 and about 20, between about 1 and about 18, between about 1 and about 15, between about 1 and about 12, between about 1 and about 10, or between about 2 and about 9. In some embodiments, the PMI1/MW is selected from the group consisting of about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, and about 9.0.

In some embodiments, the compounds disclosed herein have a combination of any number of the foregoing properties.

Exemplary Compounds

Provided herein are compounds that are derivatives or analogs of an oxazolidinone, lincosamide, mutilin, pleuromutilin, fusidic acid, ETX0914, gepotidacin, iclaprim, or a deoxynybomycin. In some embodiments, the compound has RB of 6 or less, 5 or less, or 4 or less and a Glob of 0.4 or less, 0.3 or less, 0.2 or less, or 0.1 or less; or a combination of any of the foregoing.

In certain embodiments, the compounds disclosed herein are derivatives or analogs of a compound selected from the group consisting of linezolid, eperezolid, lincomycin, clindamycin, retapamulin, pleuromutilin, fusidic acid, ETX0914, gepotidacin, iclaprim, PF-708093, AZD0914, and deoxynybomycin (FIG. 1).

Exemplary Oxazolidinone Derivatives

In some embodiments of the compounds disclosed herein, the compound is a derivative or analog of an oxazolidinone antibiotic such as linezolid or eperezolid, wherein linezolid is

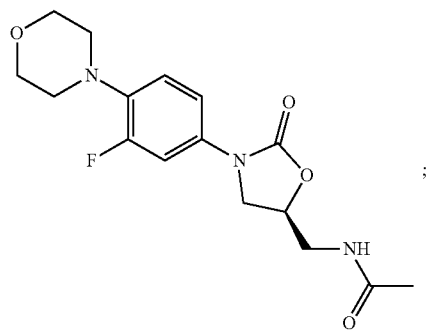 [SMILES: CC(=O)NC[C@H]1CN(c2ccc(N3CCOCC3)c(F)c2)C(=O)O1]

and
wherein eperzolid is

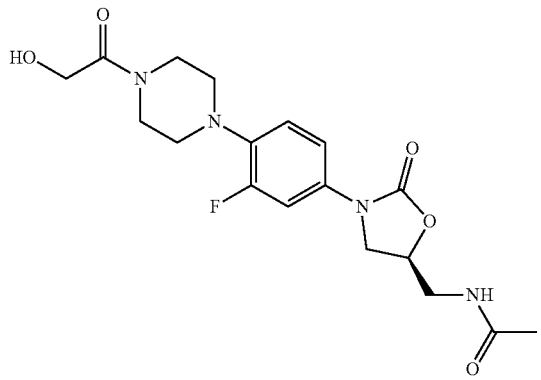

.

The compounds disclosed herein exclude linezolid and eperezolid.

In some embodiments, the oxazolidinone derivative or analog has RB of 4 or less and a Glob of 0.06 or less. In some embodiments, the lincosamide derivative or analog has RB of 4 or less, a Glob of 0.06 or less, PBF of about 0.89, and a PMI1/MW of about 2.7 or 2.9.

In some embodiments, the compound is represented by Formula (I) or a pharmaceutically acceptable salt thereof:

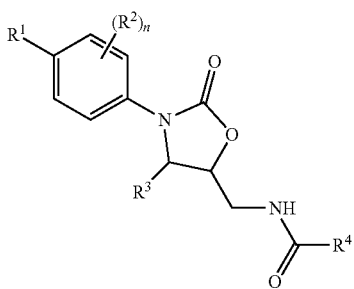

(I)

wherein, independently for each occurrence:

$R^1$ is selected from the group consisting of substituted and unsubstituted —(($C_1$-$C_6$)alkylene)N($R^5$)$_m$, —C(O)(($C_1$-$C_6$)alkylene)N($R^5$)$_m$, cycloalkyl, heterocycloalkyl, aryl, heteroaryl, aralkyl, and heteroaralkyl;

$R^2$ is selected from the group consisting of hydrogen, halogen, ($C_1$-$C_6$)alkyl, cycloalkyl, heterocycloalkyl, aryl, heteroaryl, aralkyl, heteroaralkyl, —OR$^5$, and —N($R^5$)$_m$;

$R^3$ is selected from the group consisting of hydrogen, ($C_1$-$C_6$)alkyl, —(($C_1$-$C_6$)alkylene)N($R^5$)$_m$, —C(O)(($C_1$-$C_6$)alkylene)N($R^5$)$_m$, cycloalkyl, heterocycloalkyl, aryl, heteroaryl, aralkyl, heteroaralkyl, —OR$^5$, and —N($R^5$)$_m$; or $R^2$ and $R^3$, taken together, form a 5-10-membered heterocyclic or heteroaromatic ring comprising one N heteroatom and optionally further comprising one or two heteroatoms independently selected from the group consisting of O, N, and S;

$R^4$ is selected from the group consisting of hydrogen and ($C_1$-$C_6$)alkyl;

$R^5$ is selected from the group consisting of hydrogen, ($C_1$-$C_6$)alkyl, cycloalkyl, heterocycloalkyl, aryl, heteroaryl, aralkyl, and heteroaralkyl;

n is an integer from 1-4; and
m is 2 or 3;
provided that at least one of $R^1$, $R^2$, or $R^3$ comprises a terminal —N($R^5$)$_m$.

In some embodiments, $R^1$ is selected from the group consisting of substituted and unsubstituted cycloalkyl, heterocycloalkyl, aryl, heteroaryl, aralkyl, and heteroaralkyl. In some embodiments, $R^1$ is substituted or unsubstituted heterocycloalkyl, heteroaryl, or heteroaralkyl. In some embodiments, $R^1$ is substituted or unsubstituted heterocycloalkyl or substituted or unsubstituted heteroaryl.

In some embodiments, $R^1$ is represented by

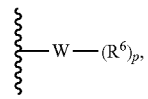

wherein W is selected from the group consisting of substituted and unsubstituted cycloalkyl, heterocycloalkyl, aryl, heteroaryl, aralkyl, and heteroaralkyl. In some embodiments, $R^1$ is represented by

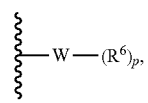

wherein W is heterocycloalkyl or heteroaryl.

In some embodiments, the compound of formula (I) is represented by Formula (Ia) or a pharmaceutically acceptable salt thereof:

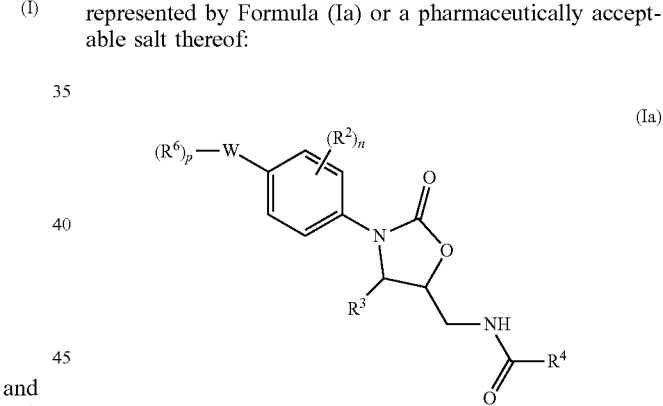

(Ia)

wherein, independently for each occurrence:

$R^1$ is represented by

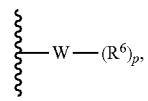

wherein W is heterocycloalkyl or heteroaryl;

$R^2$ is selected from the group consisting of hydrogen, halogen, ($C_1$-$C_6$)alkyl, cycloalkyl, heterocycloalkyl, aryl, heteroaryl, aralkyl, heteroaralkyl, —OR$^5$, and —N($R^5$)$_m$;

$R^3$ is selected from the group consisting of hydrogen, ($C_1$-$C_6$)alkyl, —(($C_1$-$C_6$)alkylene)N($R^5$)$_m$, —C(O)(($C_1$-$C_6$)alkylene)N($R^5$)$_m$, cycloalkyl, heterocycloalkyl, aryl, heteroaryl, aralkyl, heteroaralkyl, —OR$^5$, and —N($R^5$)$_m$; or $R^2$ and $R^3$, taken together, form a 5-10-membered heterocyclic or heteroaromatic ring comprising one N heteroatom and optionally further comprising one or two heteroatoms independently selected from the group consisting of O, N, and S;

$R^4$ is selected from the group consisting of hydrogen and $(C_1\text{-}C_6)$alkyl;

$R^5$ is selected from the group consisting of hydrogen, $(C_1\text{-}C_6)$alkyl, cycloalkyl, heterocycloalkyl, aryl, heteroaryl, aralkyl, and heteroaralkyl;

$R^6$ is selected from the group consisting of $(C_1\text{-}C_6)$alkyl, —$((C_1\text{-}C_6)\text{alkylene})N(R^5)_m$, —$C(O)((C_1\text{-}C_6)\text{alkylene})N(R^5)_m$, cycloalkyl, heterocycloalkyl, aryl, heteroaryl, aralkyl, heteroaralkyl, —$OR^5$, and —$N(R^5)_m$;

n is an integer from 1-4;
m is 2 or 3; and
p is an integer from 0-4;

provided that at least one of $R^2$, $R^3$, or $R^6$ comprises a terminal —$N(R^5)_m$.

In some embodiments, $R^2$ and $R^3$, taken together, form a 5-10-membered heterocyclic or heteroaromatic ring comprising one N heteroatom and optionally further comprising one or two heteroatoms independently selected from the group consisting of O, N, and S.

In some embodiments, the compound of formula (I) is represented by Formula (Ib) or a pharmaceutically acceptable salt thereof:

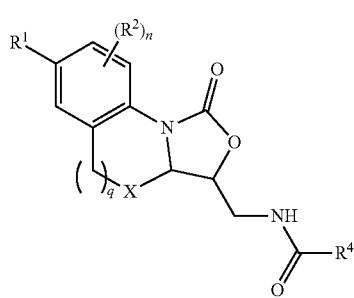

(Ib)

wherein, independently for each occurrence:

$R^1$ is selected from the group consisting of substituted and unsubstituted —$((C_1\text{-}C_6)\text{alkylene})N(R^5)_m$, —$C(O)((C_1\text{-}C_6)\text{alkylene})N(R^5)_m$, cycloalkyl, heterocycloalkyl, aryl, heteroaryl, aralkyl, and heteroaralkyl;

$R^2$ is selected from the group consisting of hydrogen, halogen, $(C_1\text{-}C_6)$alkyl, cycloalkyl, heterocycloalkyl, aryl, heteroaryl, aralkyl, heteroaralkyl, —$OR^5$, and —$N(R^5)_m$;

X is selected from the group consisting of $CH_2$, O, NH, and S;

$R^4$ is selected from the group consisting of hydrogen and $(C_1\text{-}C_6)$alkyl;

$R^5$ is selected from the group consisting of hydrogen, $(C_1\text{-}C_6)$alkyl, cycloalkyl, heterocycloalkyl, aryl, heteroaryl, aralkyl, and heteroaralkyl;

n is an integer from 1-3;
m is 2 or 3; and
q is an integer from 0-5;

provided that at least one of $R^1$ or $R^2$ comprises a terminal —$N(R^5)_m$.

In some embodiments, independently for each occurrence if present:

$R^1$ is selected from the group consisting of substituted and unsubstituted —$((C_1\text{-}C_6)\text{alkylene})N(R^5)_m$, —$C(O)((C_1\text{-}C_6)\text{alkylene})N(R^5)_m$, heterocycloalkyl, and heteroaryl; or $R^1$ is represented by

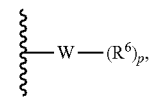

wherein W is heterocycloalkyl or heteroaryl;

$R^2$ is selected from the group consisting of hydrogen, halogen, $(C_1\text{-}C_6)$alkyl, —$OR^5$, and —$N(R^5)_m$;

$R^3$ is selected from the group consisting of hydrogen, $(C_1\text{-}C_6)$alkyl, —$((C_1\text{-}C_6)\text{alkylene})N(R^5)_m$, —$C(O)((C_1\text{-}C_6)\text{alkylene})N(R^5)_m$, —$OR^5$, and —$N(R^5)_m$; or $R^2$ and $R^3$, taken together, form a 5-10-membered heterocyclic or heteroaromatic ring comprising one N heteroatom and optionally further comprising one or two heteroatoms independently selected from the group consisting of O, N, and S;

$R^4$ is $(C_1\text{-}C_6)$alkyl;

$R^5$ is hydrogen or $(C_1\text{-}C_6)$alkyl;

$R^6$ is selected from the group consisting of $(C_1\text{-}C_6)$alkyl, —$((C_1\text{-}C_6)\text{alkyl})N(R^5)_m$, —$C(O)((C_1\text{-}C_6)\text{alkyl})N(R^5)_m$, —$OR^5$, and —$N(R^5)_m$;

X is selected from the group consisting of $CH_2$, O, NH, and S;

n is 1 or 2;
m is 2 or 3;
p is 0 or 1; and
q is 0 or 1.

In some embodiments, $R^1$ is selected from the group consisting of substituted and unsubstituted —$((C_1\text{-}C_6)\text{alkylene})N(R^5)_m$, —$C(O)((C_1\text{-}C_6)\text{alkylene})N(R^5)_m$, heterocycloalkyl, and heteroaryl; or $R^1$ is represented by

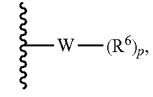

wherein W is heterocycloalkyl or heteroaryl; and $R^5$ is hydrogen or $(C_1\text{-}C_6)$alkyl.

In some embodiments, $R^1$ is selected from the group consisting of substituted and unsubstituted —$((C_1\text{-}C_6)\text{alkylene})N(R^5)_m$, —$C(O)((C_1\text{-}C_6)\text{alkylene})N(R^5)_m$, heterocycloalkyl, and heteroaryl; or $R^1$ is represented by

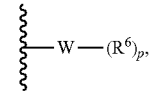

wherein W is heterocycloalkyl or heteroaryl; p is 0 or 1; and $R^5$ is hydrogen or $(C_1\text{-}C_6)$alkyl.

In some embodiments, the heterocycloalkyl or heteroaryl is selected from the group consisting of morpholinyl, piperazinyl, and pyridinyl.

In some embodiments, $R^1$ comprises a terminal —$N(R^5)_m$.

In some embodiments, $R^1$ is unsubstituted —$((C_1\text{-}C_6)\text{alkylene})N(R^5)_m$ or —$C(O)((C_1\text{-}C_6)\text{alkylene})N(R^5)_m$; and $R^5$ is hydrogen or $(C_1\text{-}C_6)$alkyl.

In some embodiments of the compounds of formula (I), (Ia), or (Ib), $R^2$ is selected from the group consisting of hydrogen, halogen, $(C_1\text{-}C_6)$alkyl, —$OR^5$, and —$N(R^5)_m$; and $R^5$ is hydrogen or $(C_1\text{-}C_6)$alkyl. In some embodiments, $R^2$ comprises a terminal —$N(R^5)_m$. In some embodiments $R^2$ is —$N(R^5)_m$. In some embodiments, $R^2$ is halogen.

In some embodiments of the compounds of formula (I), (Ia), or (Ib), $R^3$ is selected from the group consisting of hydrogen, $(C_1-C_6)$alkyl, and —$((C_1-C_6)$alkyene$)N(R^5)_m$; and $R^5$ is hydrogen or $(C_1-C_6)$alkyl. In some embodiments, $R^2$ comprises a terminal —$N(R^5)_m$. In some embodiments, $R^3$ is —$((C_1-C_6)$alkylene$)N(R^5)_m$, —$C(O)((C_1-C_6)$alkylene$)N(R^5)_m$, or —$N(R^5)_m$. In some embodiments $R^3$ is —$((C_1-C_6)$alkyene$)N(R^5)_m$. In some embodiments $R^3$ is hydrogen.

In some embodiments, $R^6$ comprises a terminal —$N(R^5)_m$. In some embodiments, $R^6$ is —$((C_1-C_6)$alkylene$)N(R^5)_m$ or —$C(O)((C_1-C_6)$alkyl$)N(R^5)_m$; $R^5$ is hydrogen or $(C_1-C_6)$alkyl; and p is 0 or 1.

In some embodiments of the compounds of formula (I), (Ia), or (Ib), m is 2. In some embodiments, m is 3.

In some embodiments of the compounds of formula (I), (Ia), or (Ib), p is 0. In some embodiments, p is 1.

In some embodiments of the compounds of formula (I), (Ia), or (Ib), q is 0.

In some embodiments, the compound of formula (I) is selected from the group consisting of:

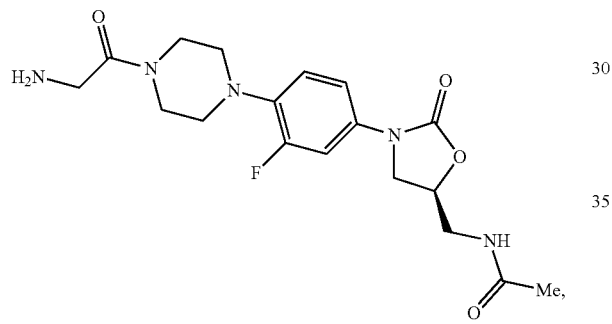

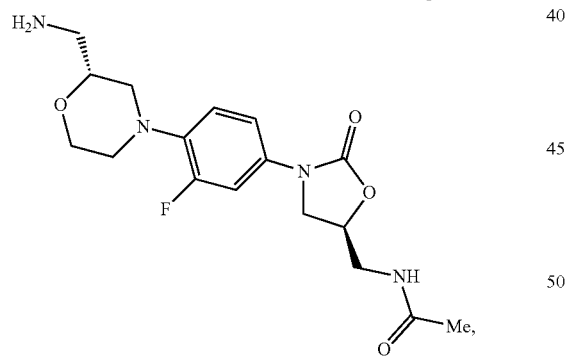

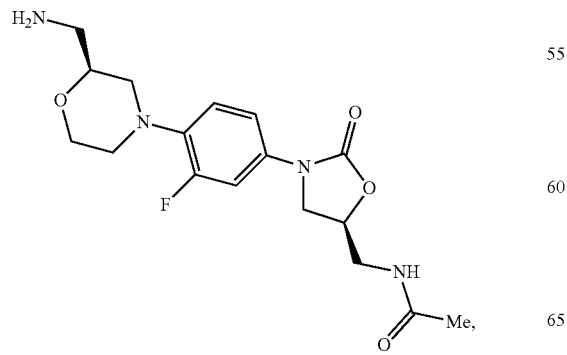

-continued

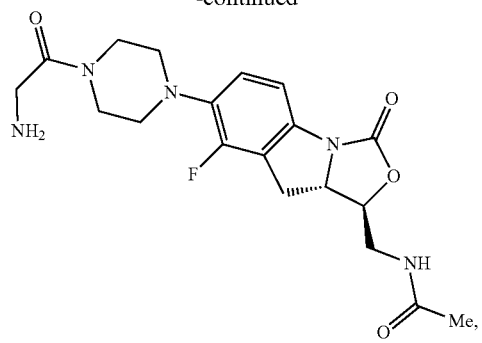

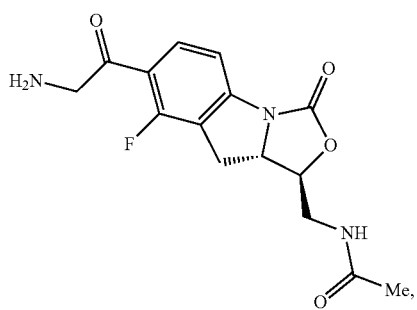

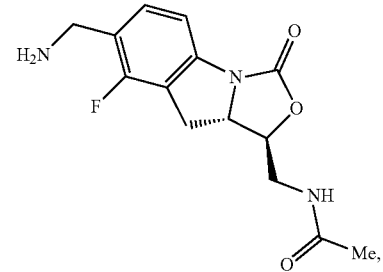

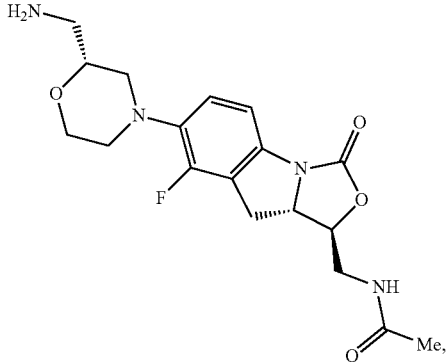

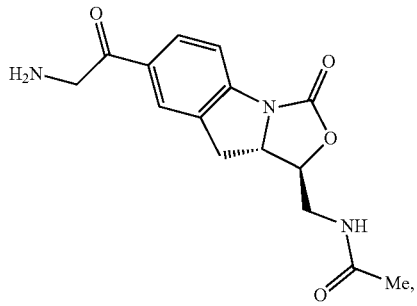

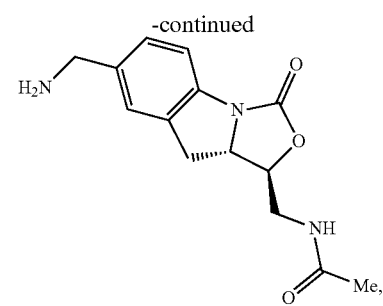
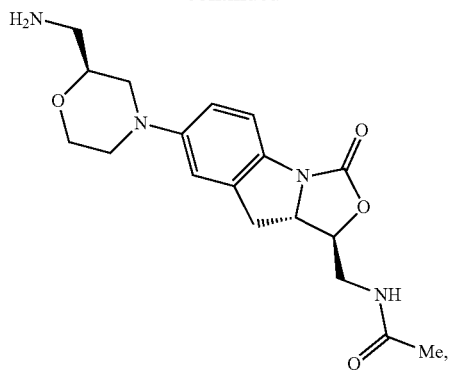
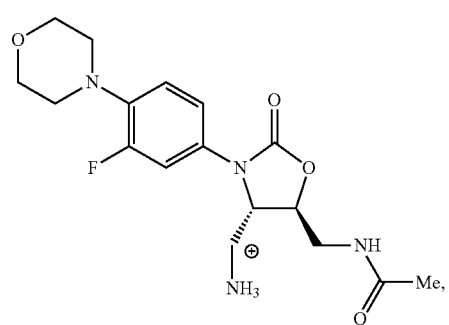
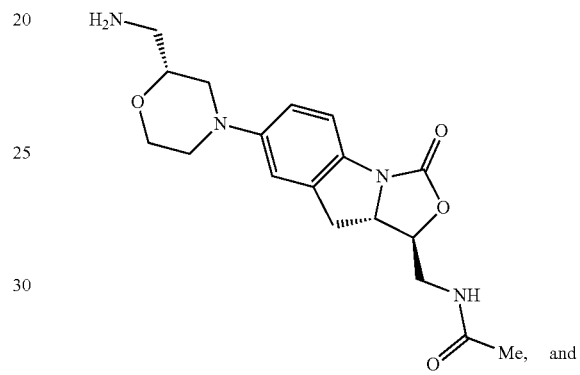
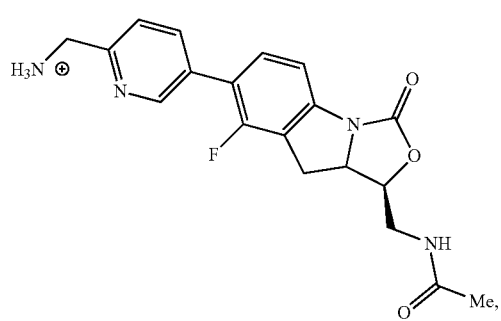
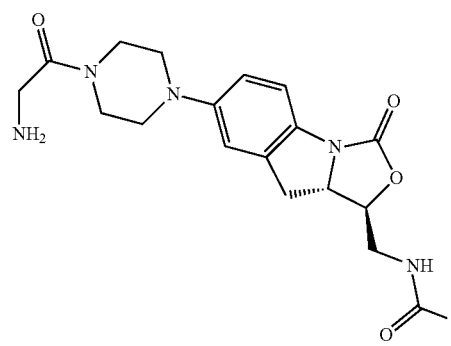
and
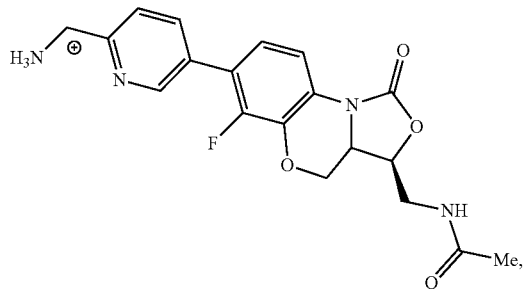
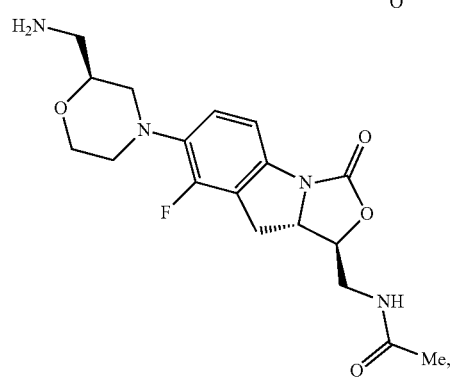
or a pharmaceutically acceptable salt thereof.
In some embodiments, the compound of formula (I) is selected from the group consisting of:
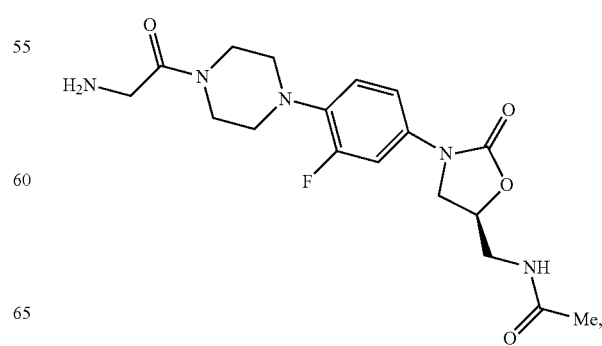

-continued
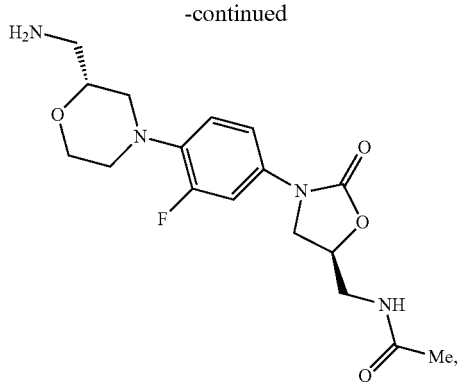
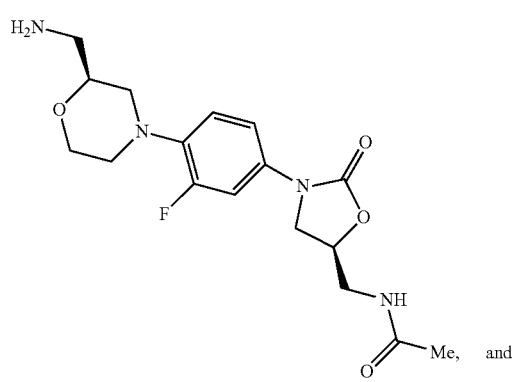
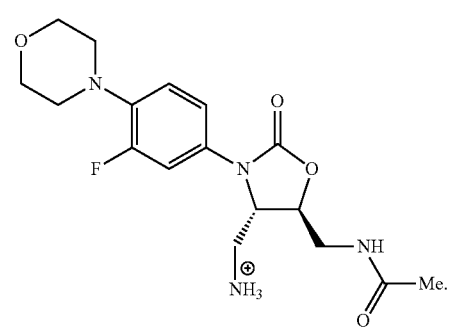
In some embodiments, the compound of formula (I) is selected from the group consisting of:
-continued
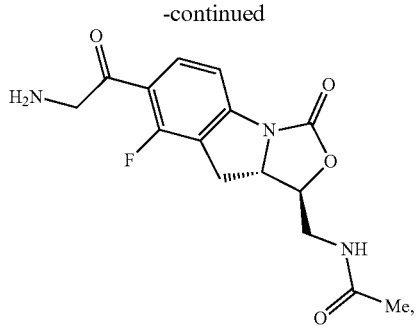
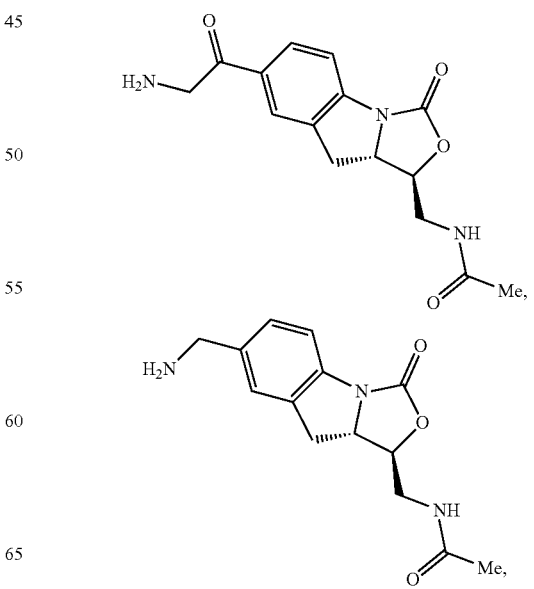

17
-continued

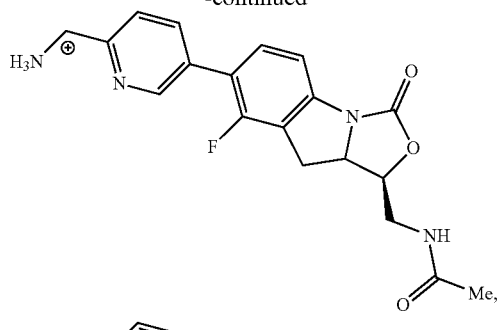

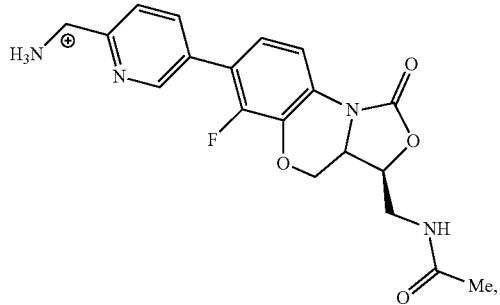

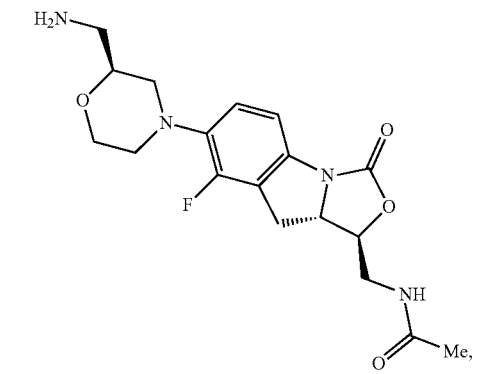

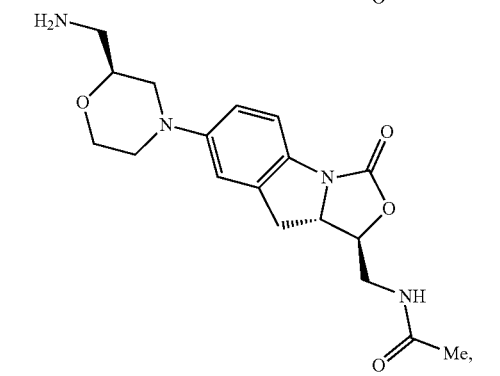

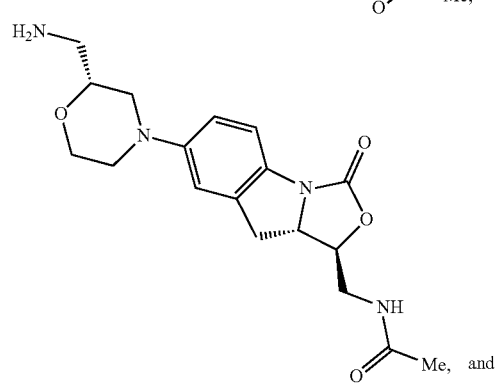

18
-continued

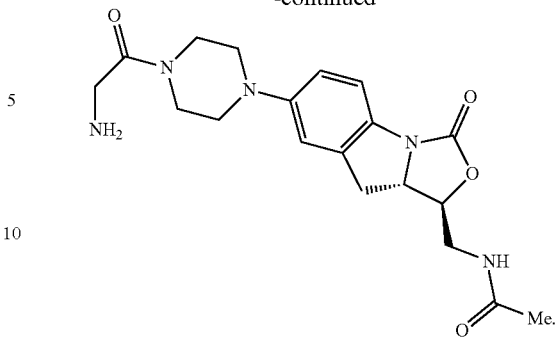

Exemplary PF-708093 Derivatives

In some embodiments of the compounds disclosed herein, the compound is a derivative or analog of PF-708093, wherein PF-708093 is

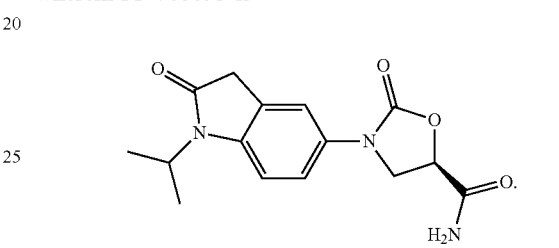

The compounds disclosed herein exclude PF-708093.

In some embodiments, the PF-708093 derivative or analog has RB of 5 or less and a Glob of 0.05 or less.

In some embodiments, the compound is represented by Formula (II) or a pharmaceutically acceptable salt thereof:

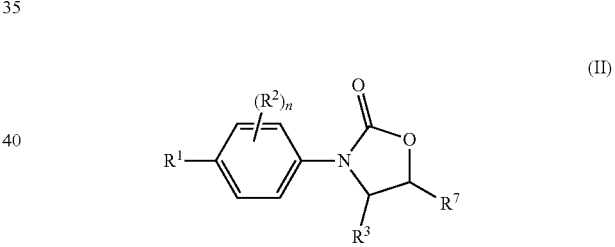

wherein, independently for each occurrence:

$R^1$ is selected from the group consisting of substituted and unsubstituted —$((C_1-C_6)$alkylene$)N(R^5)_m$, —$C(O)((C_1-C_6)$alkylene$)N(R^5)_m$, cycloalkyl, heterocycloalkyl, aryl, heteroaryl, aralkyl, and heteroaralkyl;

$R^2$ is selected from the group consisting of hydrogen, halogen, $(C_1-C_6)$alkyl, cycloalkyl, heterocycloalkyl, aryl, heteroaryl, aralkyl, heteroaralkyl, —$OR^5$, and —$N(R^5)_m$; or $R^1$ and $R^2$, taken together, form a substituted 3-10-membered cycloalkyl or aromatic ring or form a substituted 3-10-membered heterocyclic or heteroaromatic ring comprising 1-3 heteroatoms independently selected from the group consisting of O, N, and S;

$R^3$ is selected from the group consisting of hydrogen, $(C_1-C_6)$alkyl, —$((C_1-C_6)$alkylene$)N(R^5)_m$, —$C(O)((C_1-C_6)$alkylene$)N(R^5)_m$, cycloalkyl, heterocycloalkyl, aryl, heteroaryl, aralkyl, heteroaralkyl, —$OR^5$, and —$N(R^5)_m$;

$R^5$ is selected from the group consisting of hydrogen, $(C_1-C_6)$alkyl, cycloalkyl, heterocycloalkyl, aryl, heteroaryl, aralkyl, and heteroaralkyl;

$R^7$ is selected from the group consisting of —$C(O)N(R^5)_m$, —$((C_1-C_6)$alkylene$)N(R^5)_m$, —$((C_1-C_6)$alkylene$)N$ $(R^5)_m(C(O))((C_1-C_6)alkyl)$, $-C(O)(N(R^5)_m)((C_1-C_6)alkylene)N(R^5)_m$, $-C(O)(N(R^5)_m)(cycloalkyl)N(R^5)_m$, cycloalkyl, heterocycloalkyl, aryl, heteroaryl, aralkyl, and heteroaralkyl;

n is an integer from 1-4; and m is an integer from 1-3;

provided that at least one of $R^1$, $R^2$, $R^3$, or $R^7$ comprises a terminal $-N(R^5)_m$;

provided that the compound of formula (II) is not

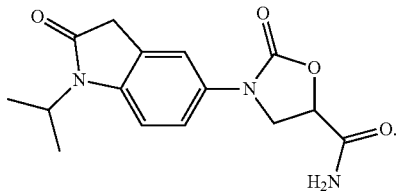 [SMILES: CC(C)N1C(=O)Cc2cc(N3CC(C(N)=O)OC3=O)ccc21]

In some embodiments, $R^1$ is selected from the group consisting of substituted and unsubstituted $-((C_1-C_6)alkylene)N(R^5)_m$, $-C(O)((C_1-C_6)alkylene)N(R^5)_m$, aralkyl, and heteroaralkyl. In some embodiments, $R^1$ is substituted or unsubstituted $-((C_1-C_6)alkylene)N(R^5)_m$ or $-C(O)((C_1-C_6)alkylene)N(R^5)_m$. In some embodiments, $R^1$ is substituted or unsubstituted aralkyl or heteroaralkyl.

In some embodiments, $R^1$ is substituted or unsubstituted cycloalkyl, heterocycloalkyl, aryl, heteroaryl, aralkyl, or heteroaralkyl. In some embodiments, $R^1$ is substituted or unsubstituted cycloalkyl, heterocycloalkyl, aryl, or heteroaryl.

In some embodiments of the compound of formula (II), $R^1$ comprises a terminal $-N(R^5)_m$.

In some embodiments, $R^1$ is selected from the group consisting of substituted cycloalkyl, heterocycloalkyl, aryl, heteroaryl, aralkyl, and heteroaralkyl.

In some embodiments, $R^1$ is represented by

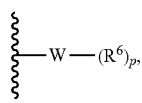

wherein W is selected from the group consisting of substituted and unsubstituted cycloalkyl, heterocycloalkyl, aryl, heteroaryl, aralkyl and heteroaralkyl. In some embodiments, $R^1$ is represented by

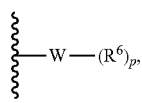

wherein W is cycloalkyl, heterocycloalkyl, aryl, or heteroaryl.

In some embodiments, the compound of formula (II) is represented by Formula (IIa) or a pharmaceutically acceptable salt thereof:

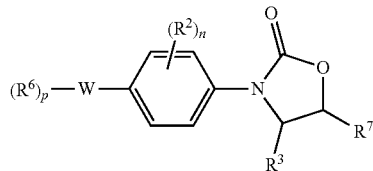

wherein, independently for each occurrence:

$R^1$ is represented by

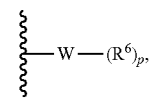

wherein W is cycloalkyl, heterocycloalkyl, aryl, or heteroaryl;

$R^2$ is selected from the group consisting of hydrogen, halogen, $(C_1-C_6)alkyl$, cycloalkyl, heterocycloalkyl, aryl, heteroaryl, aralkyl, heteroaralkyl, $-OR^5$, and $-N(R^5)_m$;

$R^3$ is selected from the group consisting of hydrogen, $(C_1-C_6)alkyl$, $-((C_1-C_6)alkylene)N(R^5)_m$, $-C(O)((C_1-C_6)alkylene)N(R^5)_m$, cycloalkyl, heterocycloalkyl, aryl, heteroaryl, aralkyl, heteroaralkyl, $-OR^5$, and $-N(R^5)_m$;

$R^5$ is selected from the group consisting of hydrogen, $(C_1-C_6)alkyl$, cycloalkyl, heterocycloalkyl, aryl, heteroaryl, aralkyl, and heteroaralkyl;

$R^6$ is selected from the group consisting of $(C_1-C_6)alkyl$, $-((C_1-C_6)alkylene)N(R^5)_m$, $-C(O)((C_1-C_6)alkylene)N(R^5)_m$, cycloalkyl, heterocycloalkyl, aryl, heteroaryl, aralkyl, heteroaralkyl, $-OR^5$, and $-N(R^5)_m$; or p is at least 2, and two $R^6$ groups taken together form an oxo;

$R^7$ is selected from the group consisting of $-C(O)N(R^5)_m$, $-((C_1-C_6)alkylene)N(R^5)_m$, $-((C_1-C_6)alkylene)N(R^5)_m(C(O))((C_1-C_6)alkyl)$, $-C(O)(N(R^5)_m)((C_1-C_6)alkylene)N(R^5)_m$, $-C(O)(N(R^5)_m)(cycloalkyl)N(R^5)_m$, cycloalkyl, heterocycloalkyl, aryl, heteroaryl, aralkyl, and heteroaralkyl;

n is an integer from 1-4;

m is an integer from 1-3; and p is an integer from 0-4;

provided that at least one of $R^2$, $R^3$, $R^6$, or $R^7$ comprises a terminal $-N(R^5)_m$.

In some embodiments, independently for each occurrence:

$R^1$ is represented by

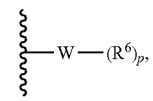

wherein W is cycloalkyl, heterocycloalkyl, or heteroaryl;

$R^2$ is selected from the group consisting of hydrogen, halogen, $(C_1-C_6)alkyl$, $-OR^5$, and $-N(R^5)_m$;

$R^6$ is $-((C_1-C_6)alkylene)N(R^5)_m$ or $-N(R^5)_m$; or p is at least 2, and two $R^6$ groups taken together form an oxo; and p is 1, 2, or 3.

In some embodiments, the cycloalkyl, heterocycloalkyl, or heteroaryl is selected from the group consisting of cyclopropyl, tetrahydrothiopyranyl, and imidazolyl.

In some embodiments, p is at least 2, and two $R^6$ groups taken together form an oxo.

In some embodiments, $R^1$ is represented by

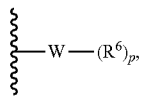

which represents

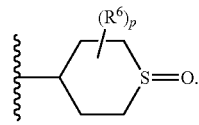

In some embodiments, $R^1$ is represented by

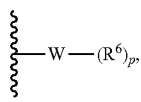

which represents

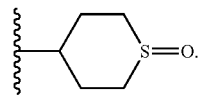

In some embodiments, $R^6$ comprises a terminal $-N(R^5)_m$. In some embodiments, $R^6$ is $-((C_1\text{-}C_6)\text{alkylene})N(R^5)_m$ or $-C(O)((C_1\text{-}C_6)\text{alkylene})N(R^5)_m$.

In some embodiments, $R^6$ is $(C_1\text{-}C_6)$alkyl, cycloalkyl, heterocycloalkyl, aryl, heteroaryl, aralkyl, heteroaralkyl, or $-OR^5$.

In some embodiments, p is 2. In some embodiments, p is 3.

In some embodiments, $R^1$ and $R^2$, taken together, form a substituted 3-10-membered cycloalkyl or aromatic ring or form a substituted 3-10-membered heterocyclic or heteroaromatic ring comprising 1-3 heteroatoms independently selected from the group consisting of O, N, and S.

In some embodiments, the compound of formula (II) is represented by Formula (IIb) or a pharmaceutically acceptable salt thereof:

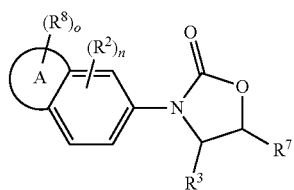

wherein, independently for each occurrence:

$R^2$ is selected from the group consisting of hydrogen, halogen, $(C_1\text{-}C_6)$alkyl, cycloalkyl, heterocycloalkyl, aryl, heteroaryl, aralkyl, heteroaralkyl, $-OR^5$, and $-N(R^5)_m$;

$R^3$ is selected from the group consisting of hydrogen, $(C_1\text{-}C_6)$alkyl, $-((C_1\text{-}C_6)\text{alkylene})N(R^5)_m$, $-C(O)((C_1\text{-}C_6)\text{alkylene})N(R^5)_m$, cycloalkyl, heterocycloalkyl, aryl, heteroaryl, aralkyl, heteroaralkyl, $-OR^5$, and $-N(R^5)_m$;

$R^5$ is selected from the group consisting of hydrogen, $(C_1\text{-}C_6)$alkyl, cycloalkyl, heterocycloalkyl, aryl, heteroaryl, aralkyl, and heteroaralkyl;

$R^7$ is selected from the group consisting of $-C(O)N(R^5)_m$, $-((C_1\text{-}C_6)\text{alkylene})N(R^5)_m$, $-((C_1\text{-}C_6)\text{alkylene})N(R^5)_m(C(O))((C_1\text{-}C_6)\text{alkyl})$, $-C(O)(N(R^5)_m)((C_1\text{-}C_6)\text{alkylene})N(R^5)_m$, $-C(O)(N(R^5)_m)(\text{cycloalkyl})N(R^5)_m$, cycloalkyl, heterocycloalkyl, aryl, heteroaryl, aralkyl, and heteroaralkyl;

$R^8$ is selected from the group consisting of $(C_1\text{-}C_6)$alkyl, $-((C_1\text{-}C_6)\text{alkylene})N(R^5)_m$, $-C(O)((C_1\text{-}C_6)\text{alkylene})N(R^5)_m$, cycloalkyl, heterocycloalkyl, aryl, heteroaryl, aralkyl, heteroaralkyl, $-OR^5$, and $-N(R^5)_m$; or n is at least 2, and two $R^8$ groups taken together form an oxo;

ring A is selected from the group consisting of cycloalkyl, heterocycloalkyl, aryl, and heteroaryl;

n is an integer from 1-3;

m is an integer from 1-3; and o is an integer from 1-4;

provided that at least one of $R^2$, $R^3$, $R^7$, or $R^8$ comprises a terminal $-N(R^5)_m$.

In some embodiments, independently for each occurrence if present:

$R^1$ is represented by

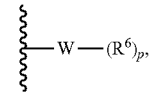

wherein W is cycloalkyl, heterocycloalkyl, or heteroaryl;

$R^2$ is selected from the group consisting of hydrogen, halogen, $(C_1\text{-}C_6)$alkyl, $-OR^5$, and $-N(R^5)_m$; or $R^1$ and $R^2$, taken together, form a substituted 3-10-membered heterocyclic comprising 1-3 heteroatoms independently selected from the group consisting of O, N, and S;

$R^3$ is selected from the group consisting of hydrogen, $(C_1\text{-}C_6)$alkyl, $-((C_1\text{-}C_6)\text{alkylene})N(R^5)_m$, $-C(O)((C_1\text{-}C_6)\text{alkylene})N(R^5)_m$, $-OR^5$, and $-N(R^5)_m$;

$R^5$ is hydrogen or $(C_1\text{-}C_6)$alkyl;

$R^6$ is selected from the group consisting of $(C_1\text{-}C_6)$alkyl, $-((C_1\text{-}C_6)\text{alkylene})N(R^5)_m$, $-C(O)((C_1\text{-}C_6)\text{alkylene})N(R^5)_m$, $-OR^5$, and $-N(R^5)_m$; or p is at least 2, and two $R^6$ groups taken together form an oxo;

$R^7$ is selected from the group consisting of $-C(O)N(R^5)_m$, $-((C_1\text{-}C_6)\text{alkyl})N(R^5)_m$, $-((C_1\text{-}C_6)\text{alkylene})N(R^5)_m(C(O))((C_1\text{-}C_6)\text{alkyl})$, $-C(O)(N(R^5)_m)((C_1\text{-}C_6)\text{alkylene})N(R^5)_m$, $-C(O)(N(R^5)_m)(\text{cycloalkyl})N(R^5)_m$, and heteroaralkyl.

$R^8$ is selected from the group consisting of $(C_1\text{-}C_6)$alkyl, $-((C_1\text{-}C_6)\text{alkylene})N(R^5)_m$, $-C(O)((C_1\text{-}C_6)\text{alkylene})N(R^5)_m$, $-OR^5$, and $-N(R^5)_m$; or o is 2, and two $R^8$ groups taken together form an oxo;

ring A is selected from the group consisting of cycloalkyl, heterocycloalkyl, aryl, and heteroaryl;

n is an integer from 1-3;

m is an integer from 1-3;

o is an integer from 1-4; and p is 1, 2, or 3.

In some embodiments of formula (IIb), $R^8$ is selected from the group consisting of $(C_1\text{-}C_6)$alkyl, $-((C_1\text{-}C_6)\text{al-}$ kylene)N(R⁵)ₘ, —C(O)((C₁-C₆)alkylene)N(R⁵)ₘ, —OR⁵, and —N(R⁵)ₘ; or o is at least 2, and two R⁸ groups taken together form an oxo;

ring A is heterocycloalkyl; and o is 1, 2, or 3.

In some embodiments, the heterocycloalkyl is pyrrolidinyl or azepanyl.

In some embodiments, R⁸ is selected from the group consisting of (C₁-C₆)alkyl, —((C₁-C₆)alkylene)N(R⁵)ₘ, —C(O)((C₁-C₆)alkylene)N(R⁵)ₘ, cycloalkyl, heterocycloalkyl, aryl, heteroaryl, aralkyl, heteroaralkyl, —OR⁵, and —N(R⁵)ₘ. In some embodiments, R⁸ comprises a terminal —N(R⁵)ₘ. In some embodiments, R⁸ is selected from the group consisting of —((C₁-C₆)alkylene)N(R⁵)ₘ, —C(O)((C₁-C₆)alkylene)N(R⁵)ₘ, and —N(R⁵)ₘ. In some embodiments, R⁸ is —((C₁-C₆)alkylene)N(R⁵)ₘ.

In some embodiments, o is 2. In some embodiments, o is 3.

In some embodiments, o is at least 2, and two R⁸ groups taken together form an oxo.

In some embodiments, o is 3, two R⁸ groups taken together form an oxo; and ring A, and the phenylene to which it is attached are represented by

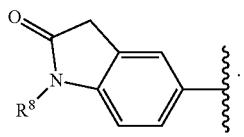

In some embodiments of the compounds of formula (II), (IIa), or (IIb), R² is selected from the group consisting of hydrogen, halogen, (C₁-C₆)alkyl, —OR⁵, and —N(R⁵)ₘ; and R⁵ is hydrogen or (C₁-C₆)alkyl. In some embodiments, R² comprises a terminal —N(R⁵)ₘ. In some embodiments R² is —N(R⁵)ₘ. In some embodiments, R² is halogen.

In some embodiments of the compounds of formula (II), (IIa), or (IIb), R³ is selected from the group consisting of hydrogen, (C₁-C₆)alkyl, and —((C₁-C₆)alkyene)N(R⁵)ₘ; and R⁵ is hydrogen or (C₁-C₆)alkyl. In some embodiments, R³ comprises a terminal —N(R⁵)ₘ. In some embodiments, R³ is —((C₁-C₆)alkylene)N(R⁵)ₘ, —C(O)((C₁-C₆)alkylene)N(R⁵)ₘ, or —N(R⁵)ₘ. In some embodiments R³ is —((C₁-C₆)alkyene)N(R⁵)ₘ. In some embodiments R³ is hydrogen.

In some embodiments, R⁷ is selected from the group consisting of —C(O)N(R⁵)ₘ, —((C₁-C₆)alkylene)N(R⁵)ₘ, —((C₁-C₆)alkylene)N(R⁵)ₘ(C(O))((C₁-C₆)alkyl), —C(O)(N(R⁵)ₘ)((C₁-C₆)alkylene)N(R⁵)ₘ, —C(O)(N(R⁵)ₘ)(cycloalkyl)N(R⁵)ₘ, and heteroaralkyl. In some embodiments, R⁷ comprises a terminal —N(R⁵)ₘ. In some embodiments, R⁷ is selected from the group consisting of —C(O)N(R⁵)ₘ, —((C₁-C₆)alkylene)N(R⁵)ₘ, —C(O)(N(R⁵)ₘ)((C₁-C₆)alkylene)N(R⁵)ₘ, and —C(O)(N(R⁵)ₘ)(cycloalkyl)N(R⁵)ₘ.

In some embodiments of the compounds of formula (II), (IIa), or (IIb), m is 1. In some embodiments, m is 2. In some embodiments, m is 3.

In some embodiments, the compound of formula (II) is selected from the group consisting of:

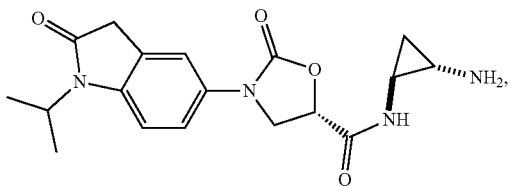

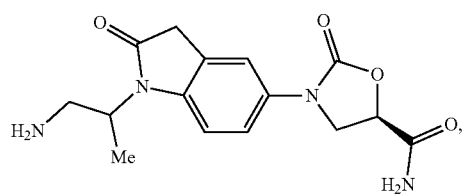

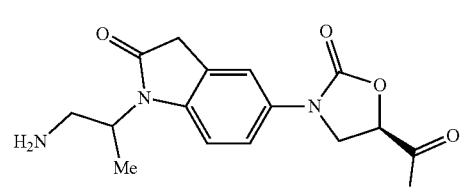

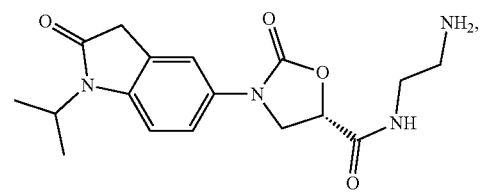

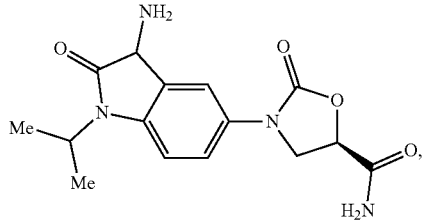

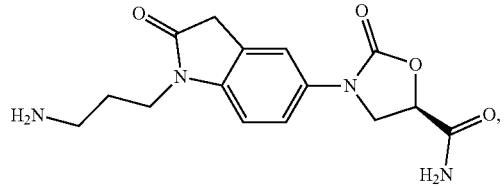

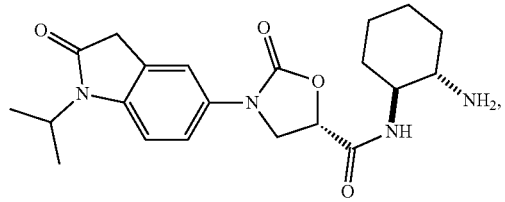

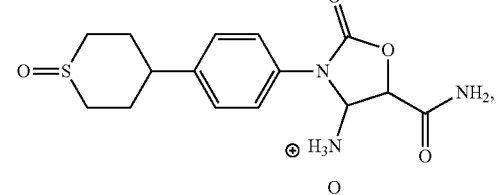

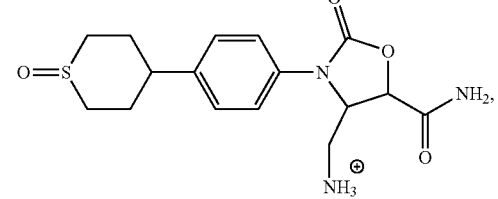

-continued
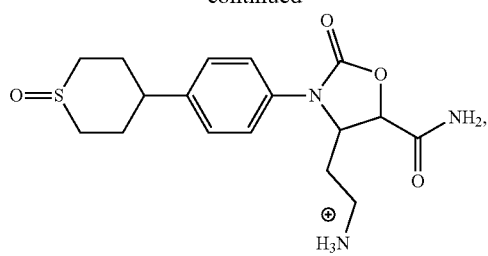
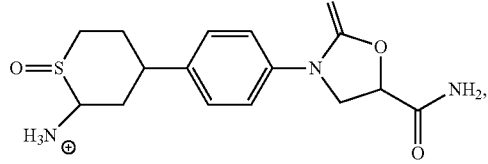
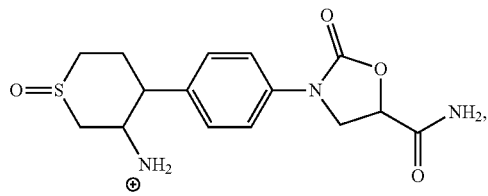
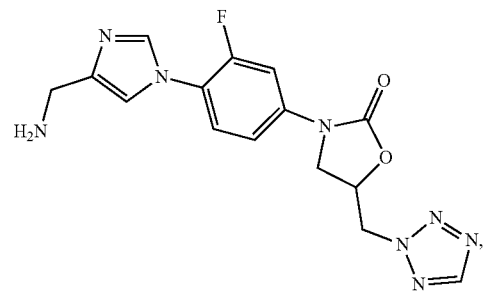
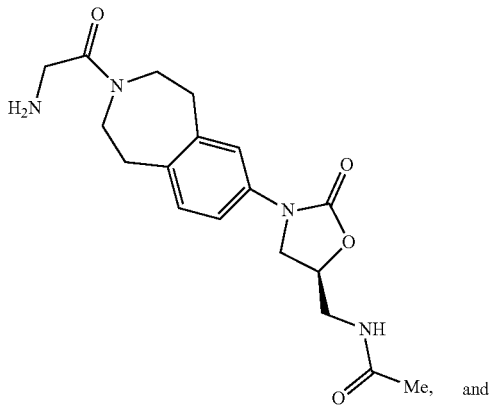
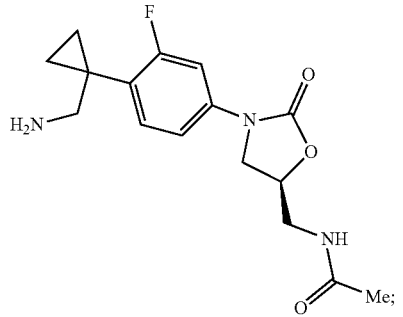
or a pharmaceutically acceptable salt thereof.
In some embodiments, the compound of formula (II) is selected from the group consisting of:
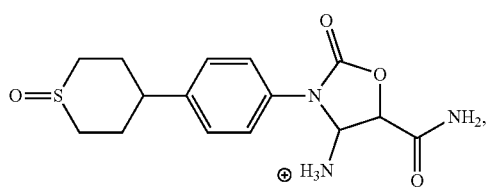
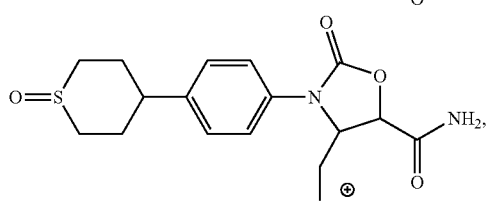
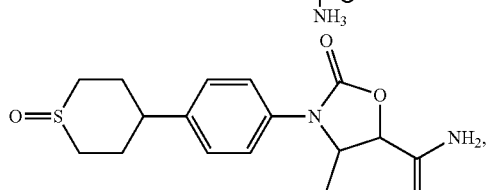
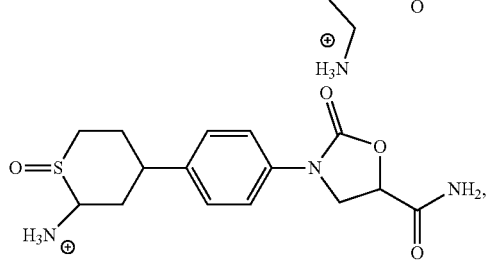
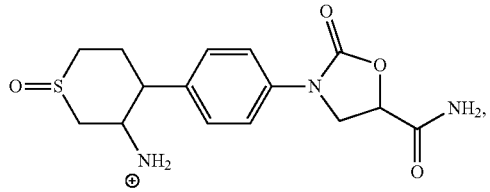
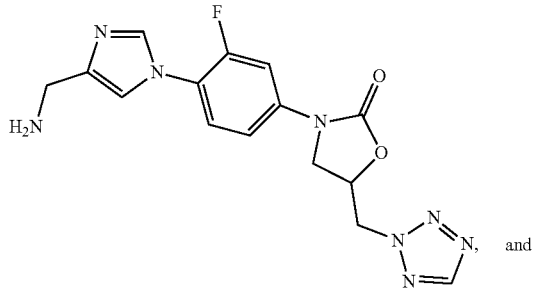
and
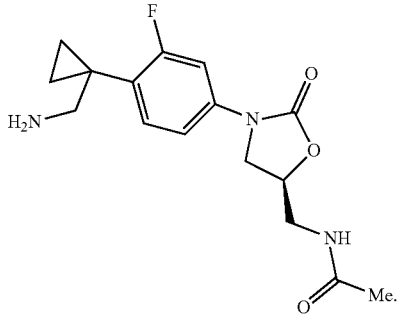

In some embodiments, the compound of formula (II) is selected from the group consisting of:

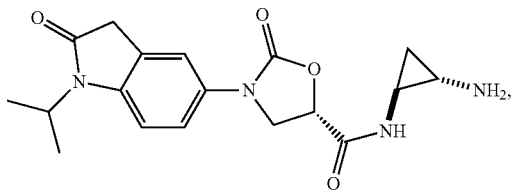

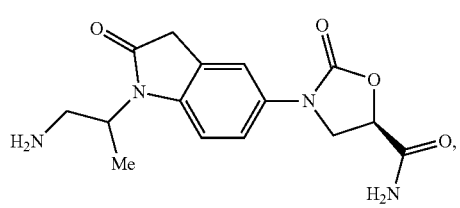

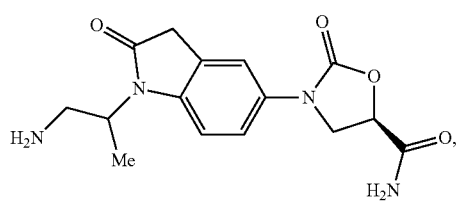

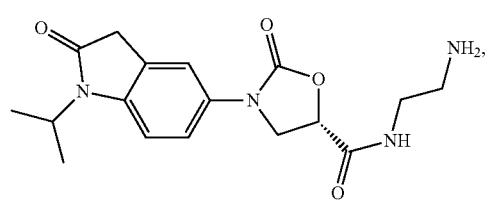

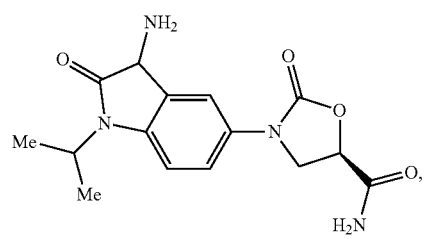

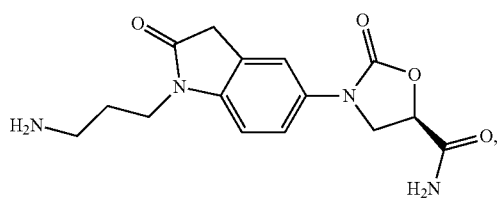

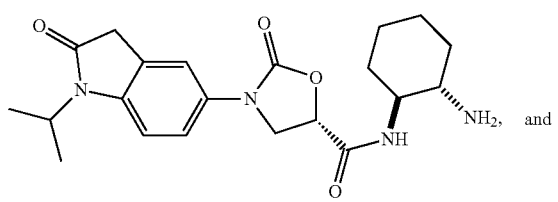

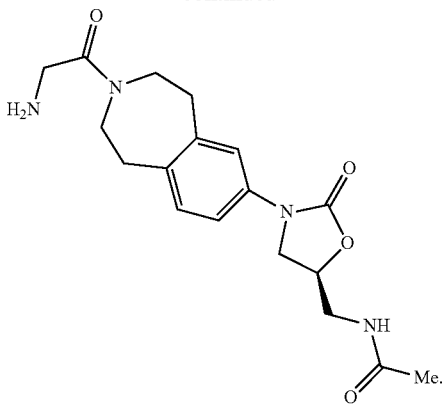 [SMILES: CC(=O)NC[C@H]1CN(c2ccc3c(c2)CCN(C(=O)CN)CC3)C(=O)O1]

Exemplary Mutilin and Pleuromutilin Derivatives

In some embodiments of the compounds disclosed herein, the compound is a derivative or analog of a mutilin or pleuromutilin, such as retapamulin or pleuromutilin, wherein retapamulin is

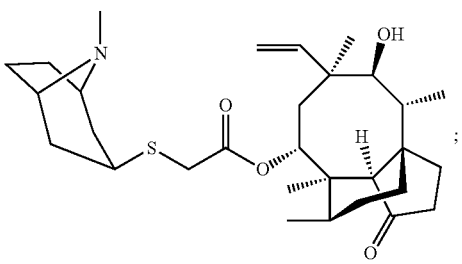

and
wherein pleuromutilin is

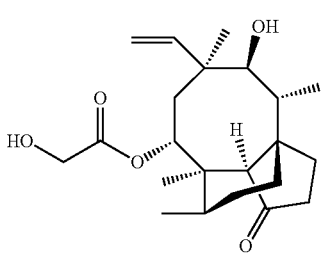

The compounds disclosed herein exclude retapamulin and pleuromutilin.

In some embodiments, the mutilin or pleuromutilin derivative or analog has RB of 6 or less and a Glob of 0.4 or less. In some embodiments, the mutilin or pleuromutilin derivative or analog has RB of 6 or less, a Glob of 0.36 or less, PBF of about 1.3, and a PMI1/MW of about 5.5.

In some embodiments, the compound is represented by Formula (III) or a pharmaceutically acceptable salt thereof:

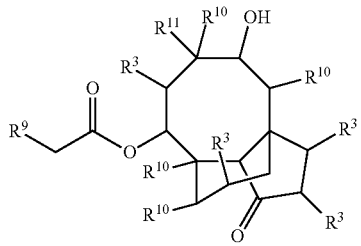

(III)

wherein, independently for each occurrence:

$R^3$ is selected from the group consisting of hydrogen, $(C_1-C_6)$alkyl, $-((C_1-C_6)$alkylene)$N(R^5)_m$, $-C(O)((C_1-C_6)$alkylene)$N(R^5)_m$, cycloalkyl, heterocycloalkyl, aryl, heteroaryl, aralkyl, heteroaralkyl, $-OR^5$, and $-N(R^5)_m$;

$R^5$ is selected from the group consisting of hydrogen, $(C_1-C_6)$alkyl, cycloalkyl, heterocycloalkyl, aryl, heteroaryl, aralkyl, and heteroaralkyl;

$R^9$ is selected from the group consisting of $-((C_1-C_6)$alkylene)$N(R^5)_m$, $-OR^5$, and $-N(R^5)_m$;

$R^{10}$ is selected from the group consisting of $(C_1-C_6)$alkyl, cycloalkyl, heterocycloalkyl, aryl, heteroaryl, aralkyl, and heteroaralkyl;

$R^{11}$ is selected from the group consisting of $(C_1-C_6)$alkyl, $(C_2-C_6)$alkenyl, $(C_2-C_6)$alkynyl, $-((C_1-C_6)$alkylene)$N(R^5)_m$, $-C(O)((C_1-C_6)$alkylene)$N(R^5)_m$, cycloalkyl, heterocycloalkyl, aryl, heteroaryl, aralkyl, and heteroaralkyl; and m is 2 or 3;

provided that at least one of $R^3$, $R^9$, or $R^{11}$ comprises a terminal $-N(R^5)_m$.

In some embodiments, independently for each occurrence:

$R^3$ is selected from the group consisting of hydrogen, $(C_1-C_6)$alkyl, $-((C_1-C_6)$alkylene)$N(R^5)_m$, $-C(O)((C_1-C_6)$alkylene)$N(R^5)_m$, $-OR^5$, and $-N(R^5)_m$;

$R^5$ is hydrogen or $(C_1-C_6)$alkyl;

$R^9$ is selected from the group consisting of $-((C_1-C_6)$alkylene)$N(R^5)_m$, $-OR^5$, and $-N(R^5)_m$;

$R^{10}$ is $(C_1-C_6)$alkyl or cycloalkyl;

$R^{11}$ is selected from the group consisting of $(C_2-C_6)$alkenyl, $(C_2-C_6)$alkynyl, $-((C_1-C_6)$alkylene)$N(R^5)_m$, $-C(O)((C_1-C_6)$alkylene)$N(R^5)_m$, heterocycloalkyl, and heteroaralkyl; and m is 2 or 3.

In some embodiments, $R^3$ is selected from the group consisting of hydrogen, $(C_1-C_6)$alkyl, $-((C_1-C_6)$alkylene)$N(R^5)_m$, $-C(O)((C_1-C_6)$alkylene)$N(R^5)_m$, $-OR^5$, and $-N(R^5)_m$; and $R^5$ is hydrogen or $(C_1-C_6)$alkyl. In some embodiments, $R^3$ comprises a terminal $-N(R^5)_m$. In some embodiments, $R^3$ is $-((C_1-C_6)$alkylene)$N(R^5)_m$, $-C(O)((C_1-C_6)$alkylene)$N(R^5)_m$, or $-N(R^5)_m$. In some embodiments, $R^3$ is $-((C_1-C_6)$alkyene)$N(R^5)_m$. In some embodiments, $R^3$ is hydrogen or $-N(R^5)_m$. In some embodiments, $R^3$ is hydrogen.

In some embodiments, $R^9$ is selected from the group consisting of $-((C_1-C_6)$alkylene)$N(R^5)_m$, $-OR^5$, and $-N(R^5)_m$; and $R^5$ is hydrogen or $(C_1-C_6)$alkyl. In some embodiments, $R^9$ is $-OR^5$ or $-N(R^5)_m$. In some embodiments, $R^9$ comprises a terminal $-N(R^5)_m$.

In some embodiments, $R^9$ is $-((C_1-C_6)$alkylene)$N(R^5)_m$ or $-N(R^5)_m$. In some embodiments, $R^9$ is $-N(R^5)_m$.

In some embodiments, $R^{10}$ is $(C_1-C_6)$alkyl or cycloalkyl. In some embodiments, $R^{10}$ is $(C_1-C_6)$alkyl.

In some embodiments, $R^{11}$ is selected from the group consisting of $(C_2-C_6)$alkenyl, $(C_2-C_6)$alkynyl, $-((C_1-C_6)$alkylene)$N(R^5)_m$, $-C(O)((C_1-C_6)$alkylene)$N(R^5)_m$, heterocycloalkyl, and heteroaralkyl. In some embodiments, $R^{11}$ is $(C_1-C_6)$alkenyl or $-((C_1-C_6)$alkyl)$N(R^5)_m$. In some embodiments, $R^{11}$ comprises a terminal $-N(R^5)_m$. In some embodiments, $R^{11}$ is $-((C_1-C_6)$alkylene)$N(R^5)_m$ or $-C(O)((C_1-C_6)$alkylene)$N(R^5)_m$. In some embodiments, $R^{11}$ is $-((C_1-C_6)$alkylene)$N(R^5)_m$.

In some embodiments, m is 2. In some embodiments, m is 3.

In some embodiments, the compound of formula (III) is selected from the group consisting of:

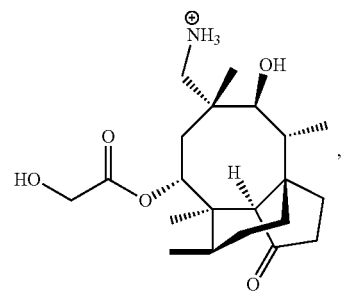

,

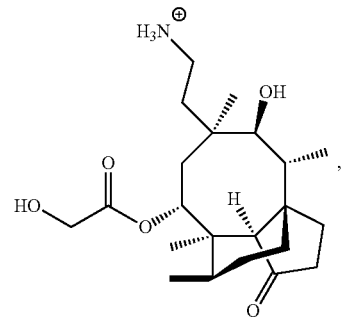

,

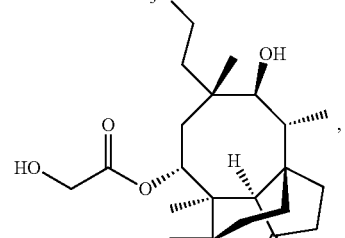

,

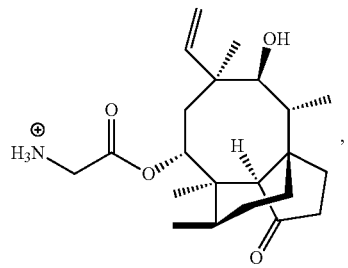

,

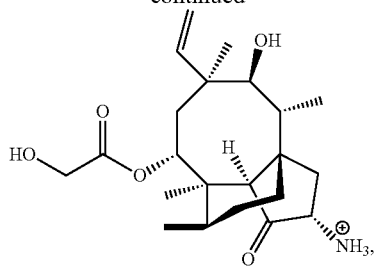

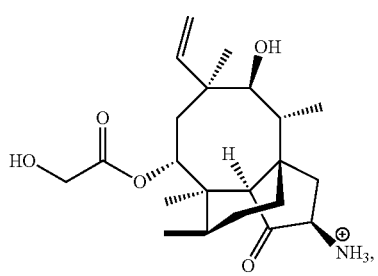

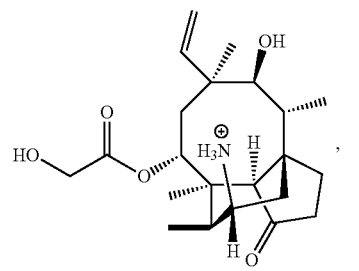

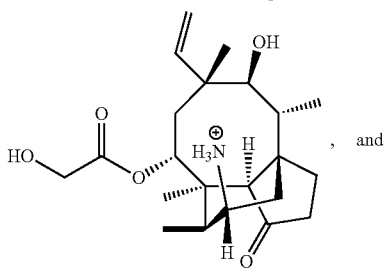, and

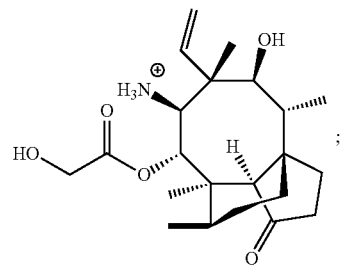;

or a pharmaceutically acceptable salt thereof.

Exemplary Lincosamide Derivatives

In some embodiments of the compounds disclosed herein, the compound is a derivative or analog of a lincosamide antibiotic such as lincomycin or clindamycin, wherein lincomycin is

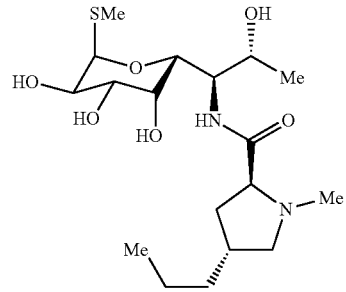

wherein clindamycin is

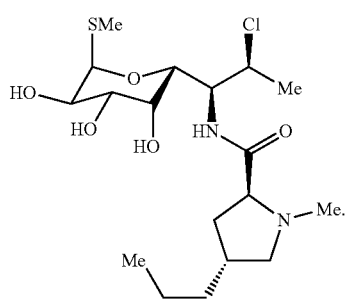

The compounds disclosed herein exclude lincomycin and clindamycin.

In some embodiments, the lincosamide derivative or analog has RB of 7 or less and a Glob of 0.2 or less. In some embodiments, the lincosamide derivative or analog has RB of 7 or less, a Glob of 0.16 or less, PBF of about 1.13, and a PMI1/MW of about 5.

In some embodiments, the compound is represented by Formula (IV) or a pharmaceutically acceptable salt thereof:

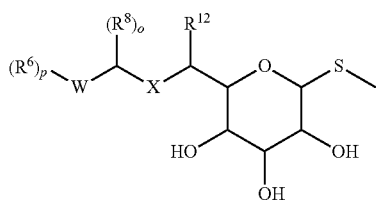

(IV)

wherein, independently for each occurrence:

$R^5$ is selected from the group consisting of hydrogen, $(C_1-C_6)$alkyl, cycloalkyl, heterocycloalkyl, aryl, heteroaryl, aralkyl, and heteroaralkyl;

$R^6$ is selected from the group consisting of $(C_1-C_6)$alkyl, —$((C_1-C_6)$alkylene$)N(R^5)_m$, —$C(O)((C_1-C_6)$alkylene$)N(R^5)_m$, —$OR^5$, and —$N(R^5)_m$;

$R^8$ is selected from the group consisting of $(C_1-C_6)$alkyl, —$((C_1-C_6)$alkylene$)N(R^5)_m$, —$C(O)((C_1-C_6)$alkylene$)N(R^5)_m$, —$OR^5$, and —$N(R^5)_m$; or o is at least 2, and two $R^8$ groups taken together form an oxo;

$R^{12}$ is selected from the group consisting of $(C_1-C_6)$alkyl, —$((C_1-C_6)$alkylene$)OR^5$, —$((C_1-C_6)$alkylene$)Z$, —$((C_1-C_6)$alkylene$)N(R^5)_m$, —$C(O)((C_1-C_6)$alkylene$)N(R^5)_m$, -(cycloalkyl$)N(R^5)_m$, cycloalkyl, heterocycloalkyl, aryl, heteroaryl, aralkyl, and heteroaralkyl; or $R^8$ and $R^{12}$, taken together, form an unsubstituted or substituted 5-10-membered heterocyclic or heteroaromatic ring comprising 1-3 heteroatoms independently selected from the group consisting of O, N, and S;

X is selected from the group consisting of $CH_2$, O, NH, and S;

W is heterocycloalkyl or heteroaryl;

Z is halogen;

m is 2 or 3;

o is 1 or 2; and p is an integer from 1-4;

provided that at least one of $R^6$, $R^8$, or $R^{12}$ comprises a terminal $—N(R^5)_m$;

provided that the compound of formula (IV) is not

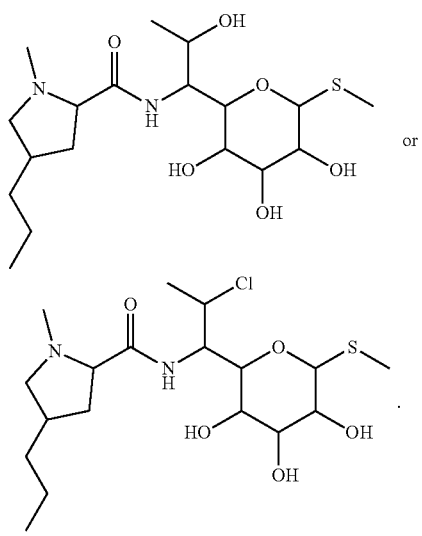

or

In some embodiments, independently for each occurrence:

$R^5$ is hydrogen or $(C_1-C_6)$alkyl;

$R^6$ is selected from the group consisting of $(C_1-C_6)$alkyl, $—((C_1-C_6)$ alkylene$)N(R^5)_m$, $—OR^5$, and $—N(R^5)_m$;

$R^8$ is $—OR^5$ or $—N(R^5)_m$; or o is 2, and two $R^8$ groups taken together form an oxo;

$R^{12}$ is selected from the group consisting of $(C_1-C_6)$alkyl, $—((C_1-C_6)$alkylene$)OR^5$, $—((C_1-C_6)$alkylene$)Z$, $—((C_1-C_6)$alkylene$)N(R^5)_m$, -(cycloalkyl)$N(R^5)_m$, cycloalkyl, heterocycloalkyl, aralkyl, and heteroaralkyl; or $R^8$ and $R^{12}$, taken together, form an unsubstituted or substituted 5-10-membered heteroaromatic ring comprising 1-3 heteroatoms independently selected from the group consisting of O, N, and S;

X is selected from the group consisting of O, NH, and S;

W is heterocycloalkyl or heteroaryl;

m is 2 or 3;

o is 1 or 2; and p is an integer from 1-4.

In some embodiments, $R^6$ is selected from the group consisting of $(C_1-C_6)$alkyl, $—((C_1-C_6)$alkylene$)N(R^5)_m$, $—OR^5$, and $—N(R^5)_m$; and $R^5$ is hydrogen or $(C_1-C_6)$alkyl. In some embodiments, $R^6$ comprises a terminal $—N(R^5)_m$. In some embodiments, $R^6$ is selected from the group consisting of $(C_1-C_6)$alkyl, $—((C_1-C_6)$alkylene$)N(R^5)_m$, and $—N(R^5)_m$.

In some embodiments, the moiety

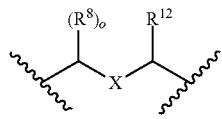

is selected from the group consisting of

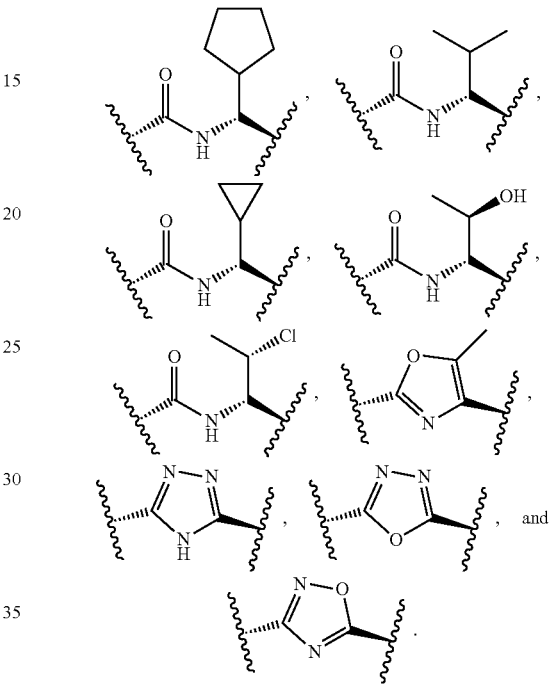

and

In some embodiments, $R^8$ comprises a terminal $—N(R^5)_m$. In some embodiments, $R^8$ is $—((C_1-C_6)$alkylene$)N(R^5)_m$, $—C(O)((C_1-C_6)$alkylene$)N(R^5)_m$, or $—N(R^5)_m$.

In some embodiments, $R^8$ is $—OR^5$ or $—N(R^5)_m$; or o is 2, and two $R^8$ groups taken together form an oxo. In some embodiments, o is 2, and two $R^8$ groups taken together form an oxo.

In some embodiments, $R^{12}$ is selected from the group consisting of $(C_1-C_6)$alkyl, $—((C_1-C_6)$alkylene$)OR^5$, $—((C_1-C_6)$alkylene$)Z$, $—((C_1-C_6)$alkylene$)N(R^5)_m$, -(cycloalkyl)$N(R^5)_m$, cycloalkyl, heterocycloalkyl, aralkyl, and heteroaralkyl. In some embodiments, $R^{12}$ is selected from the group consisting of $(C_1-C_6)$alkyl, $—((C_1-C_6)$alkylene$)OR^5$, $—((C_1-C_6)$alkylene$)Z$, 1-$C_6)$alkylene$)N(R^5)_m$, -(cycloalkyl)$N(R^5)_m$, and cycloalkyl. In some embodiments, $R^{12}$ comprises a terminal $—N(R^5)_m$. In some embodiments, $R^{12}$ is $—((C_1-C_6)$alkylene$)N(R^5)_m$, $—C(O)((C_1-C_6)$alkylene$)N(R^5)_m$, or -(cycloalkyl)$N(R^5)_m$.

In some embodiments, the moiety

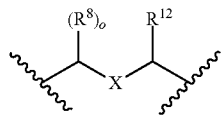

is selected from the group consisting of

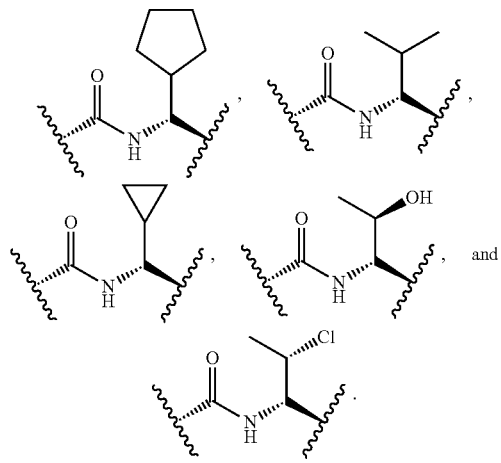

In some embodiments, $R^8$ and $R^{12}$, taken together, form an unsubstituted or substituted 5-10-membered heteroaromatic ring comprising 1-3 heteroatoms independently selected from the group consisting of O, N, and S. In some embodiments, the 5-10-membered heteroaromatic ring is selected from the group consisting of oxazolyl, oxadiazolyl, and triazolyl.

In some embodiments, X is selected from the group consisting of O, NH, and S. In some embodiments, X is NH.

In some embodiments, the moiety

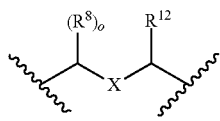

is selected from the group consisting of

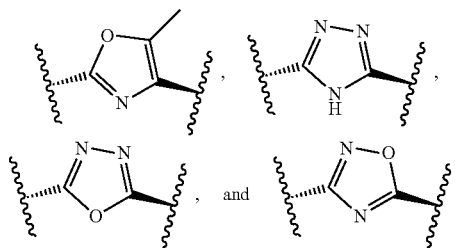

In some embodiments, W is heterocycloalkyl or heteroaryl. In some embodiments, W is heterocycloalkyl. In some embodiments, the heterocycloalkyl is selected from the group consisting of pyrrolidinyl, piperidinyl, and azepanyl.

In some embodiments, the moiety

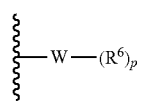

is selected from the group consisting of

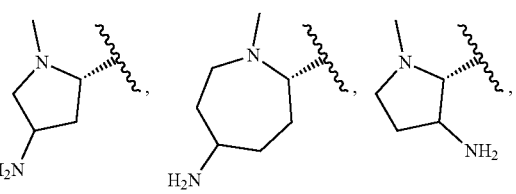

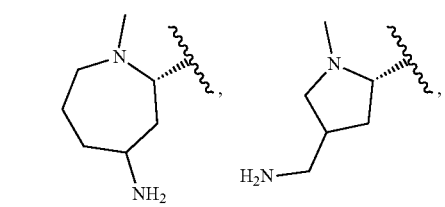

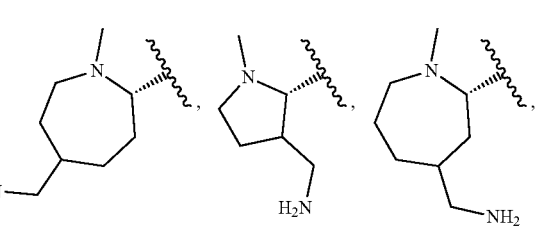

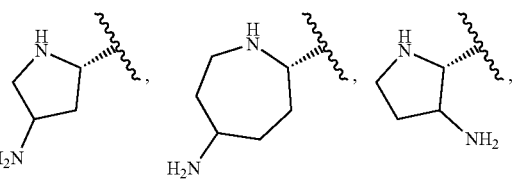

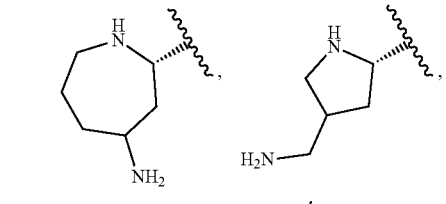

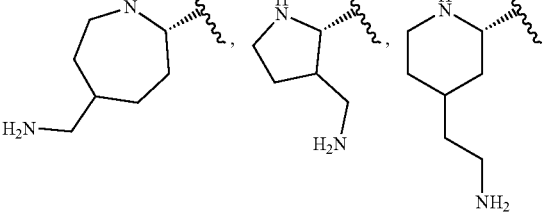

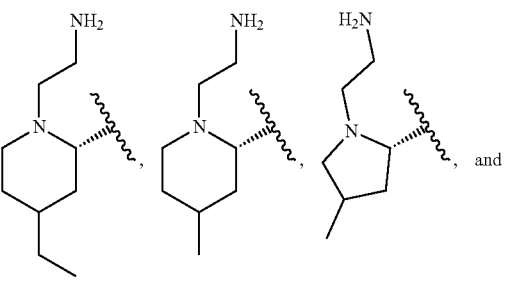

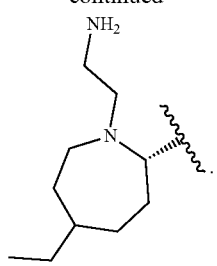

In some embodiments, m is 2. In some embodiments, m is 3.

In some embodiments, p is 1 or 2. In some embodiments, p is 1. In some embodiments, p is 2.

In some embodiments, the compound of formula (IV) is selected from the group consisting of:

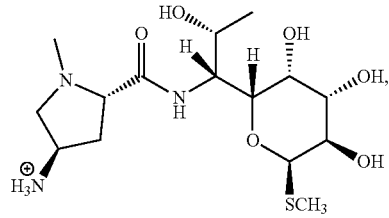

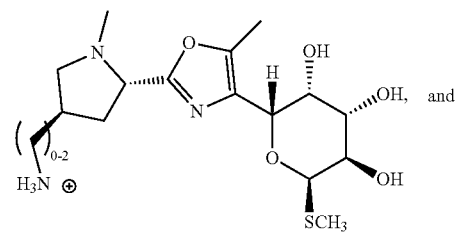

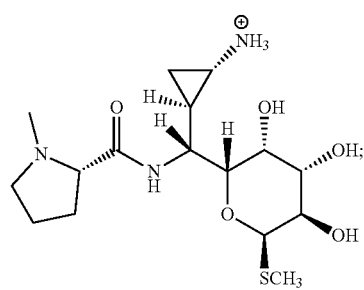

or a pharmaceutically acceptable salt thereof.

Exemplary Iclaprim Derivatives

In some embodiments of the compounds disclosed herein, the compound is a derivative or analog of a diaminopyrimidine dihydrofolate reductase (DHFR)-inhibiting antibiotic such as iclaprim or trimethoprim iclaprim, wherein iclaprim is

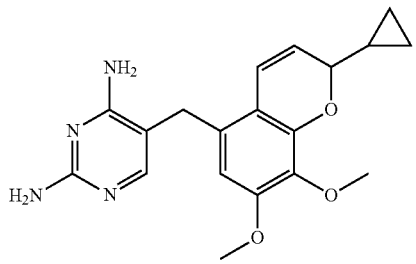

The compounds disclosed herein exclude iclaprim.

In some embodiments, the compound has RB of 5 or less and a Glob of 0.2 or less. In some embodiments, the compound has RB of 5 or less, a Glob of 0.16 or less, PBF of about 1.05, and a PMI1/MW of about 5.

In some embodiments, the compound is represented by Formula (V) or a pharmaceutically acceptable salt thereof:

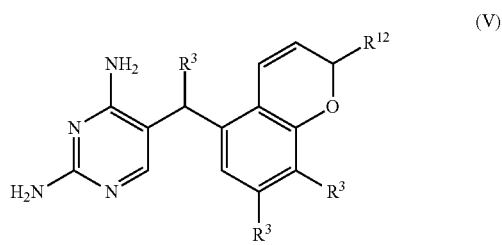

(V)

wherein, independently for each occurrence:

$R^3$ is selected from the group consisting of hydrogen, $(C_1$-$C_6)$alkyl, —$((C_1$-$C_6)$alkylene)N$(R^5)_m$, —C(O)$((C_1$-$C_6)$alkylene)N$(R^5)_m$, —OR$^5$, and —N$(R^5)_m$;

$R^5$ is selected from the group consisting of hydrogen, $(C_1$-$C_6)$alkyl, cycloalkyl, heterocycloalkyl, aryl, heteroaryl, aralkyl, and heteroaralkyl;

$R^{12}$ is selected from the group consisting of $(C_1$-$C_6)$alkyl, —$((C_1$-$C_6)$alkylene)OR$^5$, —$((C_1$-$C_6)$alkylene)Z, —$((C_1$-$C_6)$alkylene)N$(R^5)_m$, —C(O)$((C_1$-$C_6)$alkylene)N$(R^5)_m$, -(cycloalkyl)N$(R^5)_m$, cycloalkyl, heterocycloalkyl, aryl, heteroaryl, aralkyl, and heteroaralkyl; and Z is halogen;

m is 2 or 3;

provided that at least one of $R^3$ or $R^{12}$ comprises a terminal —N$(R^5)_m$.

In some embodiments, independently for each occurrence:

$R^3$ is selected from the group consisting of hydrogen, —$((C_1$-$C_6)$alkylene)N$(R^5)_m$, —C(O)$((C_1$-$C_6)$alkylene)N$(R^5)_m$, —OR$^5$, and —N$(R^5)_m$;

$R^5$ is hydrogen or $(C_1$-$C_6)$alkyl;

$R^{12}$ is selected from the group consisting of $(C_1$-$C_6)$alkyl, —$((C_1$-$C_6)$alkylene)OR$^5$, —$((C_1$-$C_6)$alkylene)Z, —$((C_1$-$C_6)$alkylene)N$(R^5)_m$, -(cycloalkyl)N$(R^5)_m$, cycloalkyl, heterocycloalkyl, aralkyl, and heteroaralkyl; and m is 2 or 3.

In some embodiments, $R^3$ is selected from the group consisting of hydrogen, $(C_1$-$C_6)$alkyl, —$((C_1$-$C_6)$alkylene)N$(R^5)_m$, —C(O)$((C_1$-$C_6)$alkylene)N$(R^5)_m$, —OR$^5$, and —N$(R^5)_m$; and $R^5$ is hydrogen or $(C_1$-$C_6)$alkyl. In some embodiments, hydrogen, —$((C_1$-$C_6)$alkyl)N$(R^5)_m$, —OR$^5$, and —N$(R^5)_m$. In some embodiments, $R^3$ comprises a terminal —N$(R^5)_m$. In some embodiments, $R^3$ is —$((C_1$-$C_6)$alkylene)N$(R^5)_m$, —C(O)$((C_1$-$C_6)$alkylene)N$(R^5)_m$, or —N(R$^5$)$_m$. In some embodiments, R$^3$ is —((C$_1$-C$_6$)alkyene)N(R$^5$)$_m$. In some embodiments, R$^3$ is hydrogen or —N(R$^5$)$_m$. In some embodiments, R$^3$ is hydrogen.

In some embodiments, R$^{12}$ is selected from the group consisting of (C$_1$-C$_6$)alkyl, —((C$_1$-C$_6$)alkylene)OR$^5$, —((C$_1$-C$_6$)alkylene)Z, —((C$_1$-C$_6$)alkylene)N(R$^5$)$_m$, -(cycloalkyl)N(R$^5$)$_m$, cycloalkyl, heterocycloalkyl, aralkyl, and heteroaralkyl; and R$^5$ is hydrogen or (C$_1$-C$_6$)alkyl. In some embodiments, R$^{12}$ is selected from the group consisting of (C$_1$-C$_6$)alkyl, —((C$_1$-C$_6$)alkylene)N(R$^5$)$_m$, -(cycloalkyl)N(R$^5$)$_m$, and cycloalkyl. In some embodiments, R$^{12}$ comprises a terminal —N(R$^5$)$_m$. In some embodiments, R$^{12}$ is —((C$_1$-C$_6$)alkylene)N(R$^5$)$_m$, —C(O)((C$_1$-C$_6$)alkylene)N(R$^5$)$_m$ or -(cycloalkyl)N(R$^5$)$_m$.

In some embodiments, m is 2. In some embodiments, m is 3.

In some embodiments, the compound of formula (V) is selected from the group consisting of:

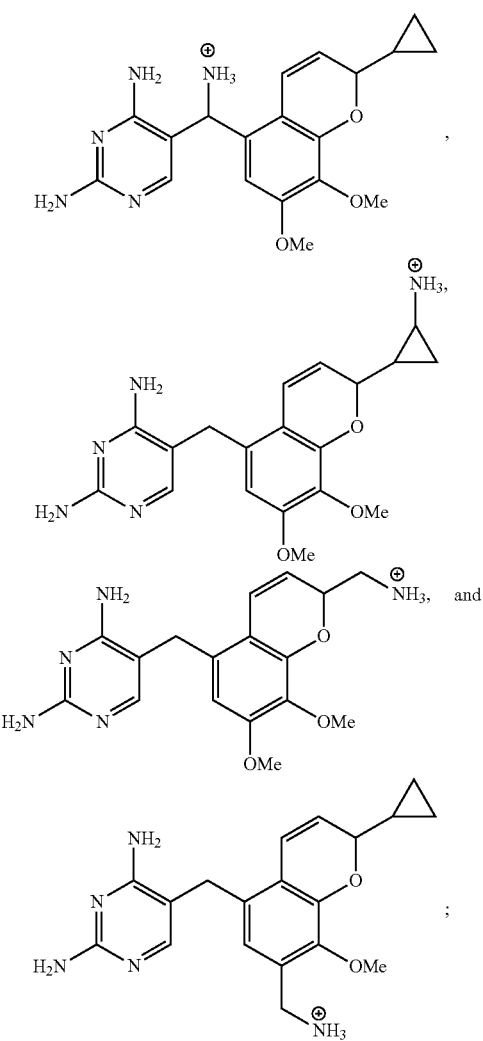

or a pharmaceutically acceptable salt thereof.

Exemplary AZD0914 Derivatives

In some embodiments of the compounds disclosed herein, the compound is a derivative or analog of AZD0914, ETX0914, or QPT-1, wherein AZD0914 or ETX0914 is

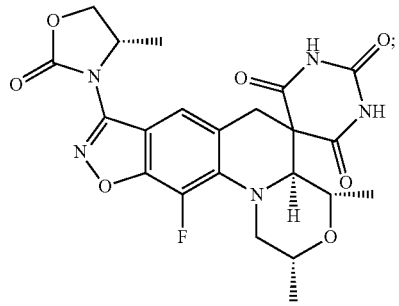

and
wherein QPT-1 is

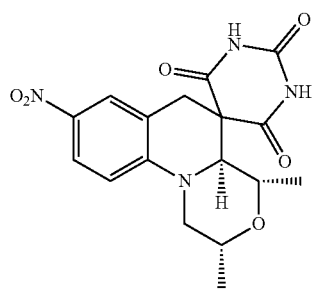

The compounds disclosed herein exclude AZD0914, ETX0914, and QPT-1.

In some embodiments, the compound has RB of 2 or less and a Glob of 0.1 or less. In some embodiments, the lincosamide derivative or analog has RB of 1 or less, a Glob of 0.09 or less, PBF of about 0.94, and a PMI1/MW of about 5.3.

In some embodiments, the compound is represented by Formula (VI) or a pharmaceutically acceptable salt thereof:

(VI)

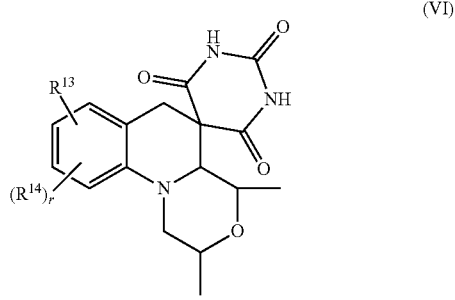

wherein, independently for each occurrence:

R$^5$ is selected from the group consisting of hydrogen, (C$_1$-C$_6$)alkyl, cycloalkyl, heterocycloalkyl, aryl, heteroaryl, aralkyl, and heteroaralkyl;

R$^{13}$ is selected from the group consisting of —CN, —NO$_2$, substituted or unsubstituted —((C$_1$-C$_6$)alkylene)N(R$^5$)$_m$, —C(O)((C$_1$-C$_6$)alkylene)N(R$^5$)$_m$, —(N(R$^5$)$_m$)((C$_1$-C$_6$)alkylene)N(R$^5$)$_m$, —C(O)(N(R$^5$)$_m$)((C$_1$-C$_6$)alkylene)N(R$^5$)$_m$, cycloalkyl, heterocycloalkyl, aryl, heteroaryl, aralkyl, and heteroaralkyl;

R$^{14}$ is selected from the group consisting of halogen, (C$_1$-C$_6$)alkyl, cycloalkyl, heterocycloalkyl, aryl, heteroaryl, aralkyl, heteroaralkyl, —OR$^5$, and —N(R$^5$)$_m$; or $R^{13}$ and $R^{14}$, taken together, form a substituted 3-10-membered cycloalkyl or aromatic ring or form a substituted 3-10-membered heterocyclic or heteroaromatic ring comprising 1-3 heteroatoms independently selected from the group consisting of O, N, and S;

m is an integer from 1-3; and r is an integer from 0-4;

provided that at least one of $R^{13}$ or $R^{14}$ comprises a terminal $-N(R^5)_m$ or a terminal $-CN$.

In some embodiments, independently for each occurrence:

$R^5$ is selected from the group consisting of hydrogen, $(C_1-C_6)$alkyl, cycloalkyl, heterocycloalkyl, aryl, heteroaryl, aralkyl, and heteroaralkyl;

$R^{13}$ is selected from the group consisting of $-CN$, $-NO_2$, substituted or unsubstituted $-((C_1-C_6)$alkylene)N$(R^5)_m$, $-C(O)((C_1-C_6)$alkylene)N$(R^5)_m$, $-(N(R^5)_m)((C_1-C_6)$alkylene)N$(R^5)_m$, and $-C(O)(N(R^5)_m)((C_1-C_6)$alkylene)N$(R^5)_m$;

$R^{14}$ is selected from the group consisting of halogen, $(C_1-C_6)$alkyl, cycloalkyl, heterocycloalkyl, aryl, heteroaryl, aralkyl, heteroaralkyl, $-OR^5$, and $-N(R^5)_m$; or m is an integer from 1-3; and r is an integer from 0-4;

provided that at least one of $R^{13}$ or $R^{14}$ comprises a terminal $-N(R^5)_m$ or a terminal $-CN$.

In some embodiments, independently for each occurrence:

$R^5$ is hydrogen or $(C_1-C_6)$alkyl;

$R^{13}$ is selected from the group consisting of $-CN$, $-NO_2$, $-((C_1-C_6)$alkylene)N$(R^5)_m$, and $-(N(R^5)_m)((C_1-C_6)$alkylene)N$(R^5)_m$;

$R^{14}$ is selected from the group consisting of halogen, $(C_1-C_6)$alkyl, $-OR^5$, and $-N(R^5)_m$;

m is an integer from 1-3; and r is 0 or 1.

In some embodiments, $R^{13}$ is selected from the group consisting of $-CN$, $-NO_2$, substituted or unsubstituted $-((C_1-C_6)$alkylene)N$(R^5)_m$, $-C(O)((C_1-C_6)$alkylene)N$(R^5)_m$, $-(N(R^5)_m)((C_1-C_6)$alkylene)N$(R^5)_m$, $-C(O)(N(R^5)_m)((C_1-C_6)$alkylene)N$(R^5)_m$, cycloalkyl, heterocycloalkyl, aryl, heteroaryl, aralkyl, and heteroaralkyl. In some embodiments, $R^{13}$ is substituted or unsubstituted cycloalkyl, heterocycloalkyl, aryl, heteroaryl, aralkyl, or heteroaralkyl. In some embodiments, $R^{13}$ is selected from the group consisting of $-CN$, $-NO_2$, substituted or unsubstituted $-((C_1-C_6)$alkylene)N$(R^5)_m$, $-C(O)((C_1-C_6)$alkylene)N$(R^5)_m$, $-(N(R^5)_m)((C_1-C_6)$alkylene)N$(R^5)_m$, and $-C(O)(N(R^5)_m)((C_1-C_6)$alkylene)N$(R^5)_m$. In some embodiments, $R^7$ comprises a terminal $-N(R^5)_m$. In some embodiments, $R^{13}$ is selected from the group consisting of substituted and unsubstituted $-((C_1-C_6)$alkylene)N$(R^5)_m$, $-C(O)((C_1-C_6)$alkylene)N$(R^5)_m$, $-(N(R^5)_m)((C_1-C_6)$alkylene)N$(R^5)_m$, and $-C(O)(N(R^5)_m)((C_1-C_6)$alkylene)N$(R^5)_m$.

In some embodiments, $R^{13}$ and $R^{14}$, taken together, form a substituted 3-10-membered cycloalkyl or aromatic ring or form a substituted 3-10-membered heterocyclic or heteroaromatic ring comprising 1-3 heteroatoms independently selected from the group consisting of O, N, and S. In some embodiments, $R^{13}$ and $R^{14}$, taken together, form a substituted 3-10-membered heterocyclic or heteroaromatic ring comprising 1-3 heteroatoms independently selected from the group consisting of O, N, and S.

In some embodiments, the compound of formula (VI) is represented by Formula (VIa) or a pharmaceutically acceptable salt thereof:

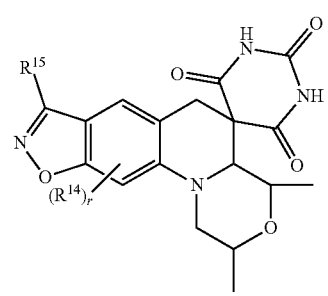

(VIa)

wherein, independently for each occurrence:

$R^5$ is selected from the group consisting of hydrogen, $(C_1-C_6)$alkyl, cycloalkyl, heterocycloalkyl, aryl, heteroaryl, aralkyl, and heteroaralkyl;

$R^6$ is selected from the group consisting of $(C_1-C_6)$alkyl, $-((C_1-C_6)$alkylene)N$(R^5)_m$, $-C(O)((C_1-C_6)$alkylene)N$(R^5)_m$, cycloalkyl, heterocycloalkyl, aryl, heteroaryl, aralkyl, heteroaralkyl, $-OR^5$, and $-N(R^5)_m$; or p is at least 2, and two $R^6$ groups taken together form an oxo;

$R^{14}$ is selected from the group consisting of halogen, $(C_1-C_6)$alkyl, cycloalkyl, heterocycloalkyl, aryl, heteroaryl, aralkyl, heteroaralkyl, $-OR^5$, and $-N(R^5)_m$; or $R^{15}$ is selected from the group consisting of $-((C_1-C_6)$alkylene)N$(R^5)_m$, $-C(O)((C_1-C_6)$alkylene)N$(R^5)_m$, and $-O((C_1-C_6)$alkylene)N$(R^5)_m$; or $R^{15}$ is represented by

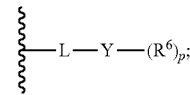

L is selected from the group consisting of a covalent bond, $-O-$, $-N(R^5)_m-$, $-C(O)-$, and $-C(O)N(R^5)_m-$;

Y is selected from the group consisting of cycloalkyl, heterocycloalkyl, aryl, and heteroaryl;

m is an integer from 1-3;

p is an integer from 0-4; and r is an integer from 0-4;

provided that at least one of $R^{14}$ or $R^{15}$ comprises a terminal $-N(R^5)_m$.

In some embodiments, $R^{14}$ is selected from the group consisting of halogen, $(C_1-C_6)$alkyl, $-OR^5$, and $-N(R^5)_m$; and $R^5$ is hydrogen or $(C_1-C_6)$alkyl. In some embodiments, $R^{14}$ comprises a terminal $-N(R^5)_m$. In some embodiments, $R^{14}$ is $-N(R^5)_m$.

In some embodiments, $R^{15}$ comprises a terminal $-N(R^5)_m$. In some embodiments, $R^{15}$ is selected from the group consisting of $-((C_1-C_6)$alkylene)N$(R^5)_m$, $-C(O)((C_1-C_6)$alkylene)N$(R^5)_m$, and $-O((C_1-C_6)$alkylene)N$(R^5)_m$. In some embodiments, $R^{15}$ is $-((C_1-C_6)$alkylene)N$(R^5)_m$ or $-O((C_1-C_6)$alkylene)N$(R^5)_m$.

In some embodiments, $R^{15}$ is represented by

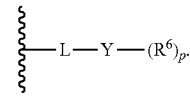

In some embodiments, L is selected from the group consisting of a covalent bond, $-(C_1-C_6)$alkylene-, $-O-$, $-N(R^5)_m-$, $-C(O)-$ and $-C(O)N(R^5)_m-$;

Y is selected from the group consisting of cycloalkyl, heterocycloalkyl, aryl, and heteroaryl;

$R^5$ is hydrogen or $(C_1-C_6)$alkyl;

$R^6$ is selected from the group consisting of —$((C_1-C_6)$alkylene$)N(R^5)_m$, —$C(O)((C_1-C_6)$alkylene$)N(R^5)_m$, —$OR^5$, and —$N(R^5)_m$; or p is at least 2, and two $R^6$ groups taken together form an oxo; and p is an integer from 1-3.

In some embodiments, Y is selected from the group consisting of cyclopropyl, cyclopentenyl, azetidinyl, oxazolindinyl, and phenyl.

In some embodiments, p is at least 2, and two $R^6$ groups taken together form an oxo.

In some embodiments, $R^{15}$ is represented by a moiety selected from the group consisting of:

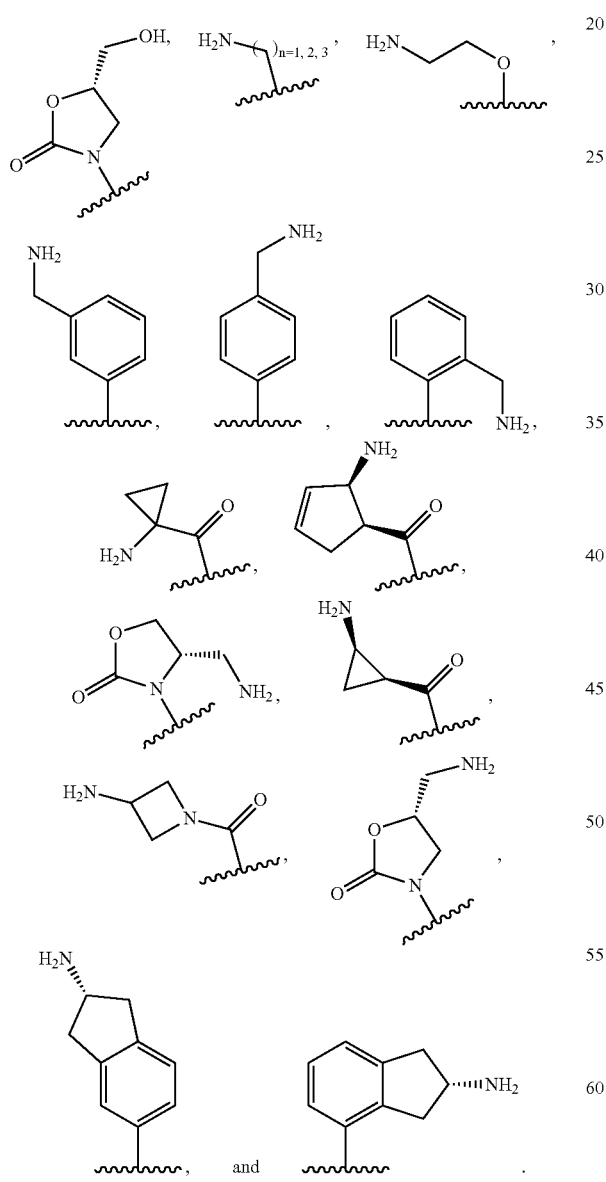

In some embodiments, m is 1. In some embodiments, m is 2. In some embodiments, m is 3.

In some embodiments, the compound of formula (VI) is selected from the group consisting of:

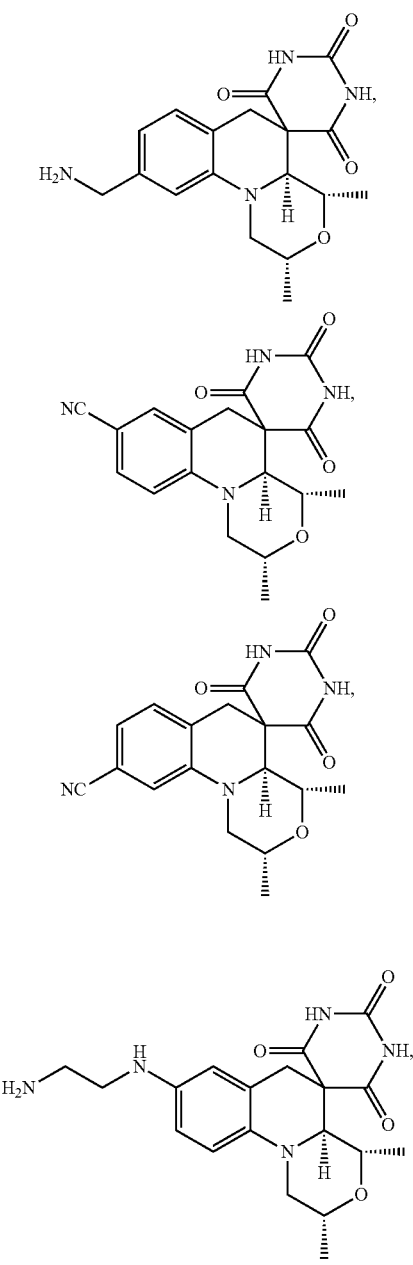

-continued
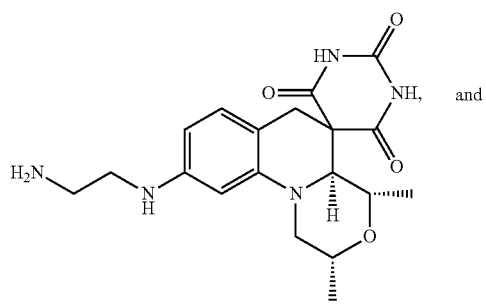
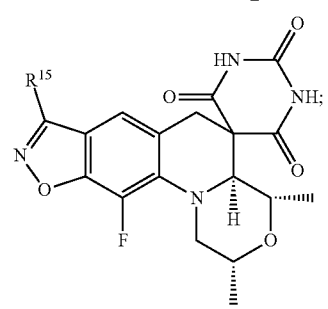
or a pharmaceutically acceptable salt thereof, wherein $R^{15}$ is represented by a moiety selected from the group consisting of:
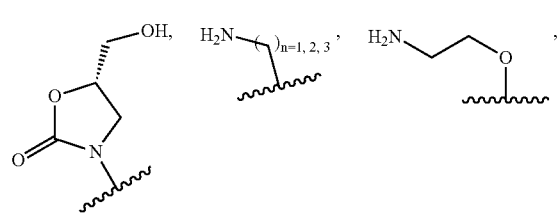
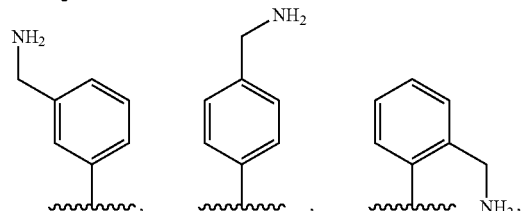
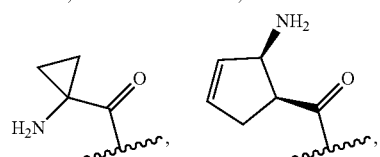
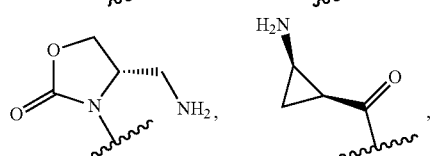
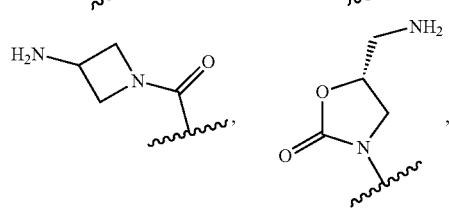
-continued
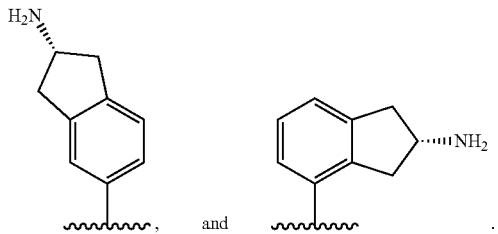
In some embodiments, the compound of formula (VI) is selected from the group consisting of:
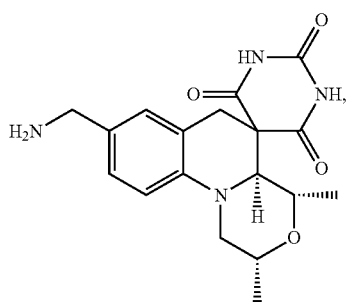
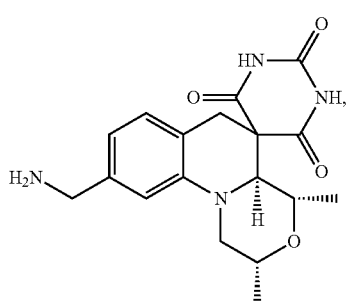
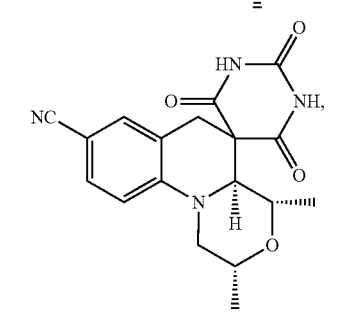
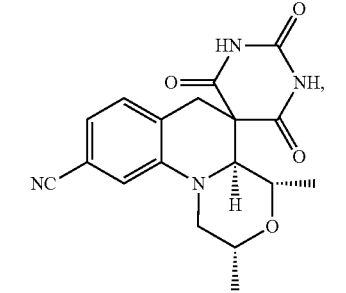

-continued

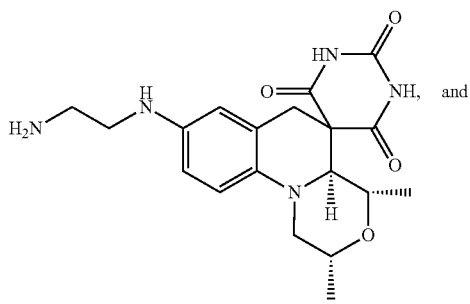 and

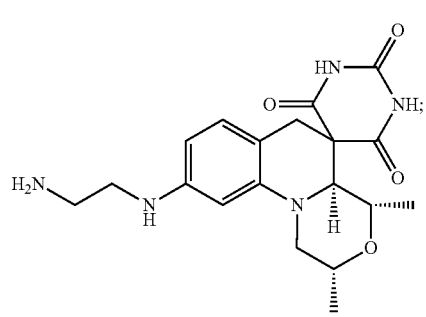

a pharmaceutically acceptable salt thereof.

In some embodiments, the compound of formula (VI) is

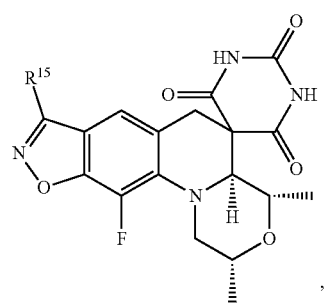

wherein $R^{15}$ is represented by a moiety selected from the group consisting of:

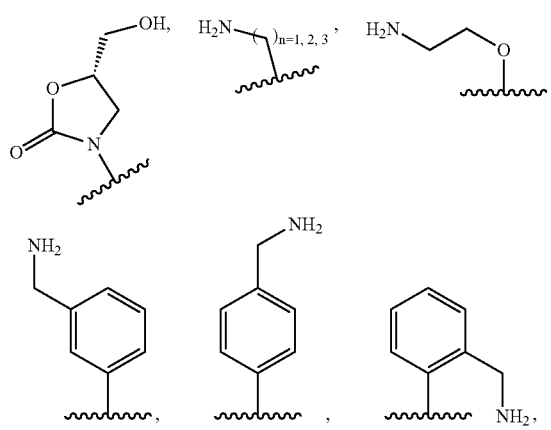

-continued

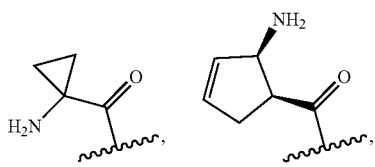

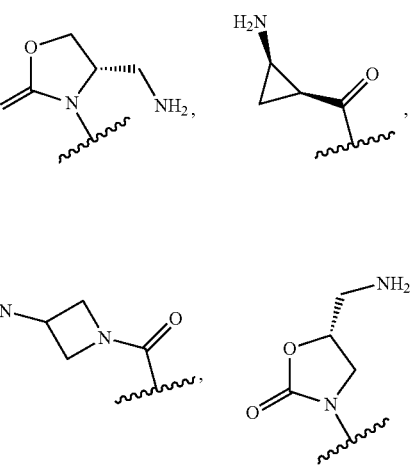

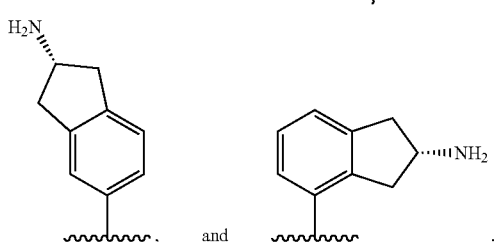

Exemplary Gepotidacin Derivatives

In some embodiments of the compounds disclosed herein, the compound is a derivative or analog of gepotidacin, wherein gepotidacin is

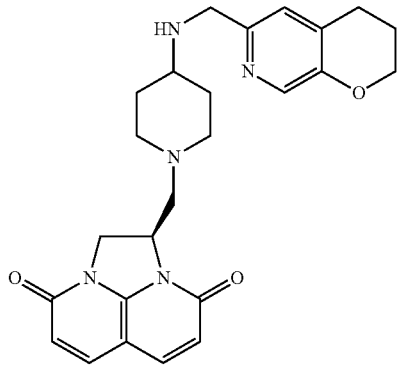

The compounds disclosed herein exclude gepotidacin.

In some embodiments, the compound has RB of 5 or less and a Glob of 0.15 or less. In some embodiments, the compound has RB of 5 or less, a Glob of 0.12 or less, PBF of about 1.1, and a PMI1/MW of about 4.4.

In some embodiments, the compound is represented by Formula (VII) or a pharmaceutically acceptable salt thereof:

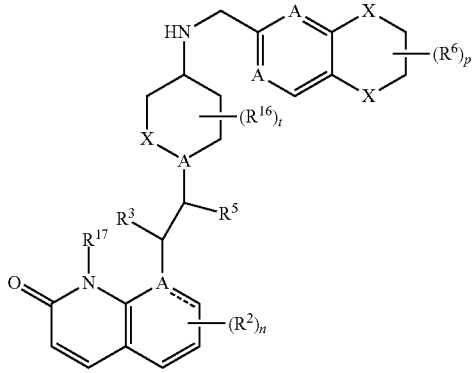
(VII)

wherein, independently for each occurrence:
--- represents a single or a double bond;
$R^3$ is selected from the group consisting of hydrogen, $(C_1-C_6)$alkyl, —$((C_1-C_6)$alkylene$)N(R^5)_m$, —$C(O)((C_1-C_6)$alkylene$)N(R^5)_m$, cycloalkyl, heterocycloalkyl, aryl, heteroaryl, aralkyl, heteroaralkyl, —$OR^5$, and —$N(R^5)_m$;
$R^{17}$ is selected from the group consisting of hydrogen, $(C_1-C_6)$alkyl, cycloalkyl, heterocycloalkyl, aryl, heteroaryl, aralkyl, and heteroaralkyl; or
$R^3$ and $R^{17}$, taken together, form a 5-10-membered heterocyclic or heteroaromatic ring comprising one N heteroatom and optionally further comprising one or two heteroatoms independently selected from the group consisting of O, N, and S;
$R^2$ is selected from the group consisting of hydrogen, halogen, $(C_1-C_6)$alkyl, cycloalkyl, heterocycloalkyl, aryl, heteroaryl, aralkyl, heteroaralkyl, —$OR^5$, and —$N(R^5)_m$; or n is at least 2, and two $R^2$ groups taken together form an oxo;
$R^5$ is selected from the group consisting of hydrogen, $(C_1-C_6)$alkyl, cycloalkyl, heterocycloalkyl, aryl, heteroaryl, aralkyl, and heteroaralkyl;
$R^6$ is selected from the group consisting of $(C_1-C_6)$alkyl, cycloalkyl, heterocycloalkyl, —$((C_1-C_6)$alkylene$)N(R^5)_m$, —$C(O)((C_1-C_6)$alkylene$)N(R^5)_m$, —$OR^5$, and —$N(R^5)_m$; or p is at least 2, and two $R^6$ groups taken together form an oxo; and
$R^{16}$ is selected from the group consisting of —$((C_1-C_6)$alkylene$)N(R^5)_m$, —$C(O)((C_1-C_6)$alkylene$)N(R^5)_m$, —$OR^5$, and —$N(R^5)_m$; or t is at least 2, and two $R^{16}$ groups taken together form a $C_1-C_5$ carbon bridge; and
A is C or N;
X is selected from the group consisting of $CH_2$, O, NH, and S;
m is 2 or 3;
n is an integer from 1-4;
p is an integer from 0-4; and
t is an integer from 0-4;
provided that at least one of $R^3$, $R^6$, or $R^{16}$ comprises a terminal —$N(R^5)_m$.

In some embodiments, independently for each occurrence if present:
$R^3$ is selected from the group consisting of hydrogen, $(C_1-C_6)$alkyl, —$((C_1-C_6)$alkylene$)N(R^5)_m$, —$C(O)((C_1-C_6)$alkylene$)N(R^5)_m$, —$OR^5$, and —$N(R^5)_m$;

$R^{17}$ is hydrogen or $(C_1-C_6)$alkyl; or
$R^3$ and $R^{17}$, taken together, form a 5-10-membered heterocyclic or heteroaromatic ring comprising one N heteroatom and optionally further comprising one or two heteroatoms independently selected from the group consisting of O, N, and S;
$R^2$ is selected from the group consisting of hydrogen, halogen, $(C_1-C_6)$alkyl, —$OR^5$, and —$N(R^5)_m$; or n is at least 2, and two $R^2$ groups taken together form an oxo;
$R^5$ is hydrogen or $(C_1-C_6)$alkyl;
$R^6$ is selected from the group consisting of $(C_1-C_6)$alkyl, —$((C_1-C_6)$alkylene$)N(R^5)_m$, —$C(O)((C_1-C_6)$alkylene$)N(R^5)_m$, —$OR^5$, and —$N(R^5)_m$; or p is at least 2, and two $R^6$ groups taken together form an oxo;
$R^{16}$ is selected from the group consisting of —$((C_1-C_6)$alkylene$)N(R^5)_m$, —$C(O)((C_1-C_6)$alkylene$)N(R^5)_m$, —$OR^5$, and —$N(R^5)_m$; or t is at least 2, and two $R^{16}$ groups taken together form a C1-C5 carbon bridge; and
A is C or N;
X is selected from the group consisting of $CH_2$, O, NH, and S;
m is 2 or 3;
n is an integer from 1-4;
p is an integer from 0-4; and
t is an integer from 0-4.

In some embodiments, $R^3$ is selected from the group consisting of hydrogen, $(C_1-C_6)$alkyl, —$((C_1-C_6)$alkylene$)N(R^5)_m$, and —$N(R^5)_m$; and $R^{17}$ is hydrogen or $(C_1-C_6)$alkyl. In some embodiments, $R^3$ is hydrogen or —$N(R^5)_m$. In some embodiments, $R^3$ comprises a terminal —$N(R^5)_m$. In some embodiments, $R^3$ is —$((C_1-C_6)$alkylene$)N(R^5)_m$, —$C(O)((C_1-C_6)$alkylene$)N(R^5)_m$, or —$N(R^5)_m$. In some embodiments $R^3$ is —$N(R^5)_m$. In some embodiments $R^3$ is hydrogen.

In some embodiments, $R^3$ and $R^{17}$, taken together, form a 5-10-membered heterocyclic or heteroaromatic ring comprising one N heteroatom and optionally further comprising one or two heteroatoms independently selected from the group consisting of O, N, and S.

In some embodiments, the compound of formula (VII) is represented by Formula (VIIa) or a pharmaceutically acceptable salt thereof:

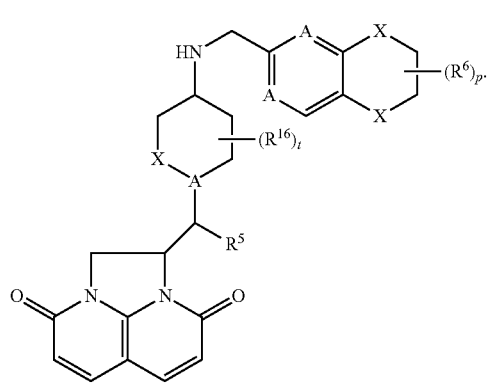
(VIIa)

In some embodiments, X is $CH_2$.
In some embodiments, the compound of formula (VII) or (VIIa) is represented by Formula (VIIb) or a pharmaceutically acceptable salt thereof:

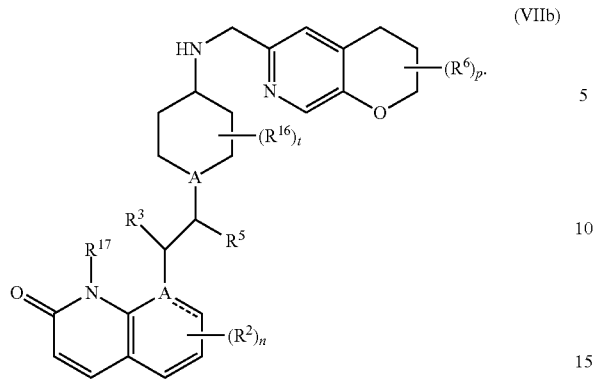

(VIIb)

In some embodiments of the compounds of formula (VII), (VIIa), or (VIIb), $R^6$ is selected from the group consisting of $(C_1-C_6)$alkyl, $-((C_1-C_6)$alkylene$)N(R^5)_m$, $-C(O)((C_1-C_6)$alkylene$)N(R^5)_m$, $-OR^5$, and $-N(R^5)_m$; or p is at least 2, and two $R^6$ groups taken together form an oxo.

In some embodiments, $R^6$ is selected from the group consisting of $(C_1-C_6)$alkyl, $-((C_1-C_6)$alkylene$)N(R^5)_m$, $-C(O)((C_1-C_6)$alkylene$)N(R^5)_m$, $-OR^5$, and $-N(R^5)_m$. In some embodiments, $R^6$ comprises a terminal $-N(R^5)_m$. In some embodiments, $R^6$ is $-((C_1-C_6)$alkylene$)N(R^5)_m$, $-C(O)((C_1-C_6)$alkyl$)N(R^5)_m$, or $-N(R^5)_m$; $R^5$ is hydrogen or $(C_1-C_6)$alkyl; and p is 0 or 1.

In some embodiments, p is at least 2, and two $R^6$ groups taken together form an oxo.

In some embodiments, p is 0.

In some embodiments of the compounds of formula (II), (IIa), or (IIb), $R^{16}$ is selected from the group consisting of $-((C_1-C_6)$alkylene$)N(R^5)_m$, $-C(O)((C_1-C_6)$alkylene$)N(R^5)_m$, $-OR^5$, and $-N(R^5)_m$. In some embodiments, $R^{16}$ comprises a terminal $-N(R^5)_m$. In some embodiments, $R^{16}$ is $-((C_1-C_6)$alkylene$)N(R^5)_m$, $-C(O)((C_1-C_6)$alkyl$)N(R^5)_m$, or $-N(R^5)_m$. In some embodiments, $R^{16}$ is $-((C_1-C_6)$alkylene$)N(R^5)_m$, $-C(O)((C_1-C_6)$alkyl$)N(R^5)_m$, or $-N(R^5)_m$. In some embodiments, $R^{16}$ is $-((C_1-C_6)$alkylene$)N(R^5)_m$ or $-N(R^5)_m$.

In some embodiments of the compounds of formula (II), (IIa), or (IIb), A is N.

In some embodiments, A is C. In some embodiments, t is at least 2, and two $R^{16}$ groups taken together form a $C_1-C_5$ carbon bridge; and A in the bridged ring is C.

In some embodiments, m is 2. In some embodiments, m is 3.

In some embodiments, the compound of formula (VII) is selected from the group consisting of:

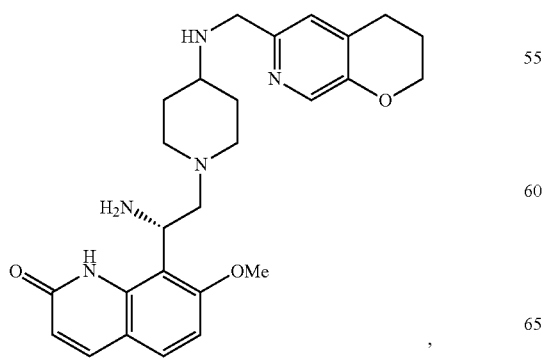

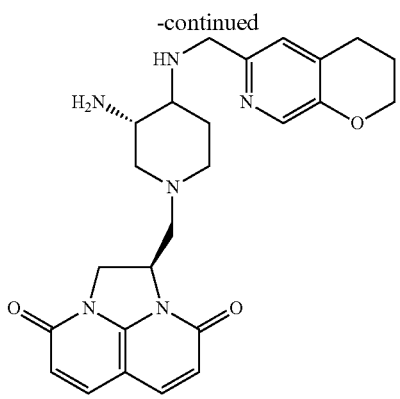

,

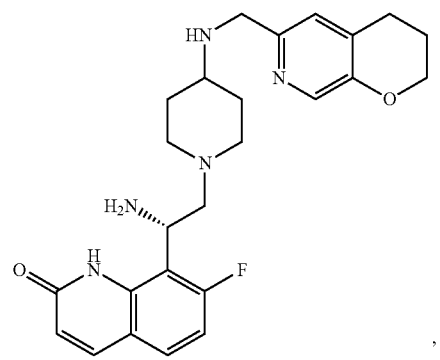

,

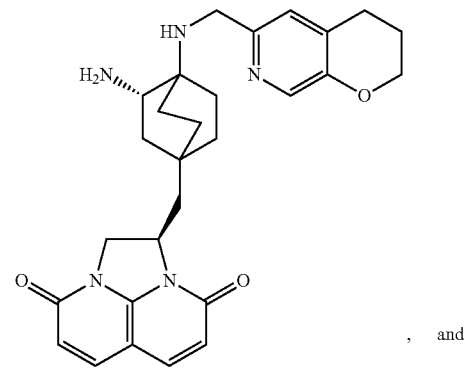

, and

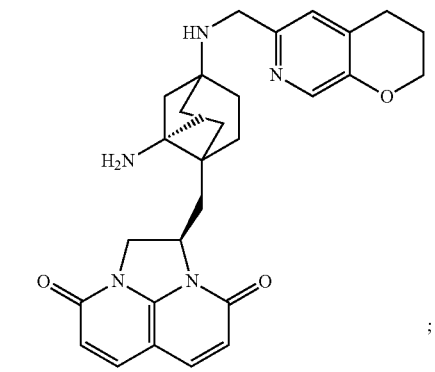

;

or a pharmaceutically acceptable salt thereof.

In some embodiments, the compound of formula (VII) is

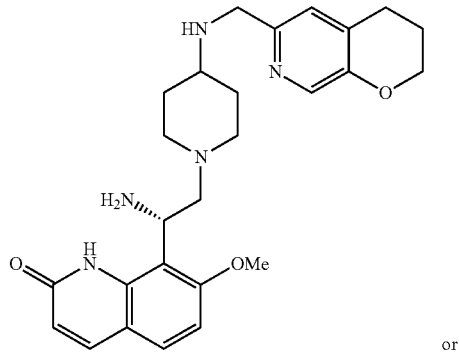

or

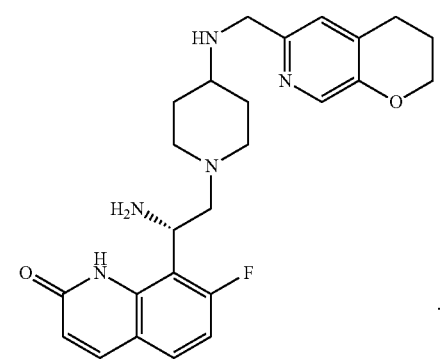

In some embodiments, the compound of formula (VII) is selected from the group consisting of:

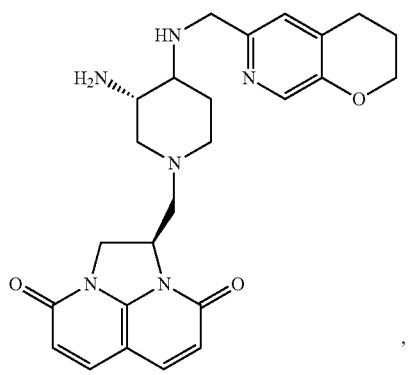 [SMILES: O=c1ccc2ccc(=O)n3c2n1C[C@H]3CN1CCC(NCc2cc3c(cn2)OCCC3)CC1]

,

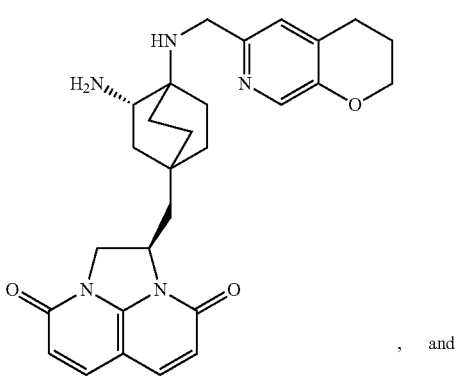

, and

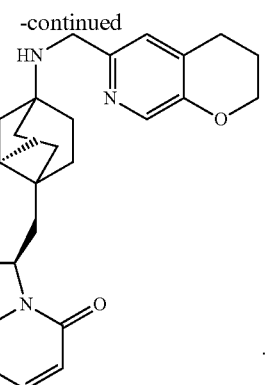

Exemplary Fusidic Acid Derivatives

In some embodiments of the compounds disclosed herein, the compound is a derivative or analog of fusidic acid, wherein fusidic acid is

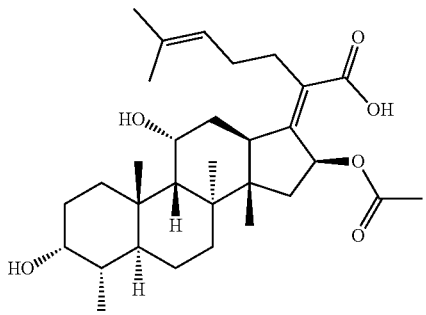

The compounds disclosed herein exclude fusidic acid.

In some embodiments, the compound has RB of 6 or less and a Glob of 0.15 or less. In some embodiments, the compound has RB of 6 or less, a Glob of 0.1 or less, PBF of about 1.05, and a PMI1/MW of about 3.17.

In some embodiments, the compound is represented by Formula (VIII) or a pharmaceutically acceptable salt thereof:

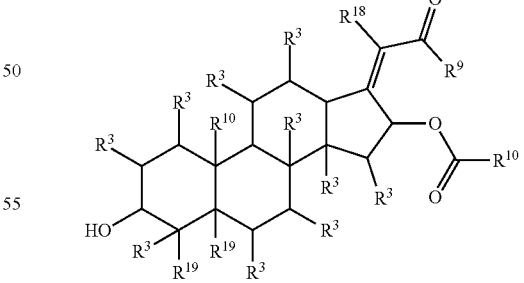

(VIII)

wherein, independently for each occurrence:

$R^3$ is selected from the group consisting of hydrogen, $(C_1-C_6)$alkyl, $-((C_1-C_6)$alkylene$)N(R^5)_m$, $-C(O)((C_1-C_6)$alkylene$)N(R^5)_m$, cycloalkyl, heterocycloalkyl, aryl, heteroaryl, aralkyl, heteroaralkyl, $-OR^5$, and $-N(R^5)_m$;

$R^5$ is selected from the group consisting of hydrogen, $(C_1-C_6)$alkyl, cycloalkyl, heterocycloalkyl, aryl, heteroaryl, aralkyl, and heteroaralkyl;

$R^9$ is selected from the group consisting of —(($C_1$-$C_6$)alkylene)N($R^5$)$_m$, —O$R^5$, and —N($R^5$)$_m$;

$R^{10}$ is selected from the group consisting of ($C_1$-$C_6$)alkyl, cycloalkyl, heterocycloalkyl, aryl, heteroaryl, aralkyl, and heteroaralkyl;

$R^{18}$ is selected from the group consisting of ($C_1$-$C_6$)alkyl, ($C_2$-$C_6$)alkenyl, ($C_2$-$C_6$)alkynyl, —(($C_1$-$C_6$)alkylene)N($R^5$)$_m$, —C(O)(($C_1$-$C_6$)alkylene)N($R^5$)$_m$, cycloalkyl, heterocycloalkyl, aryl, heteroaryl, aralkyl, and heteroaralkyl; or $R^{18}$ is represented by $$\{-L-Y-(R^{20})_u;$$

L is selected from the group consisting of a covalent bond, —(($C_1$-$C_6$)alkylene)-, —O—, —N($R^5$)$_m$—, —C(O)—, and —C(O)N($R^5$)$_m$—;

Y is selected from the group consisting of cycloalkyl, heterocycloalkyl, aryl, and heteroaryl;

$R^{19}$ is selected from the group consisting of ($C_1$-$C_6$)alkyl, —(($C_1$-$C_6$)alkylene)N($R^5$)$_m$, —C(O)(($C_1$-$C_6$)alkylene)N($R^5$)$_m$, -(cycloalkyl)(($C_1$-$C_6$)alkyl), -(heterocycloalkyl)(($C_1$-$C_6$)alkyl), -(aryl)(($C_1$-$C_6$)alkyl), -(heteroaryl)(($C_1$-$C_6$)alkyl), cycloalkyl, heterocycloalkyl, aryl, heteroaryl, aralkyl, heteroaralkyl, —O$R^5$, and —N($R^5$)$_m$;

$R^{20}$ is selected from the group consisting of ($C_1$-$C_6$)alkyl, —(($C_1$-$C_6$)alkylene)N($R^5$)$_m$, —C(O)(($C_1$-$C_6$)alkylene)N($R^5$)$_m$, —(($C_1$-$C_6$)alkene)(($C_1$-$C_6$)alkyl), —(($C_1$-$C_6$)alkene)(cycloalkyl), —(($C_1$-$C_6$)alkene)(heterocycloalkyl), —O$R^5$, and —N($R^5$)$_m$;

m is 2 or 3; and u is an integer from 0-4;

provided that at least one of $R^3$, $R^6$, $R^9$, $R^{18}$, or $R^{19}$ comprises a terminal —N($R^5$)$_m$.

In some embodiments, independently for each occurrence:

$R^3$ is selected from the group consisting of hydrogen, ($C_1$-$C_6$)alkyl, —(($C_1$-$C_6$)alkylene)N($R^5$)$_m$, —C(O)(($C_1$-$C_6$)alkylene)N($R^5$)$_m$, —O$R^5$, and —N($R^5$)$_m$;

$R^5$ is hydrogen or ($C_1$-$C_6$)alkyl;

$R^9$ is selected from the group consisting of —(($C_1$-$C_6$)alkylene)N($R^5$)$_m$, —O$R^5$, and —N($R^5$)$_m$;

$R^{10}$ is ($C_1$-$C_6$)alkyl or cycloalkyl;

$R^{18}$ is selected from the group consisting of ($C_1$-$C_6$)alkyl, ($C_2$-$C_6$)alkenyl, ($C_2$-$C_6$)alkynyl, cycloalkyl, heterocycloalkyl, aryl, heteroaryl, aralkyl, and heteroaralkyl; or $R^{18}$ is represented by $$\{-L-Y-(R^{20})_u;$$

L is a covalent bond or —(($C_1$-$C_6$)alkylene)-;

Y is selected from the group consisting of cycloalkyl, heterocycloalkyl, aryl, and heteroaryl;

$R^{19}$ is selected from the group consisting of ($C_1$-$C_6$)alkyl, —(($C_1$-$C_6$)alkylene)N($R^5$)$_m$, —C(O)(($C_1$-$C_6$)alkylene)N($R^5$)$_m$, -(cycloalkyl)(($C_1$-$C_6$)alkyl), -(heterocycloalkyl)(($C_1$-$C_6$)alkyl), -(aryl)(($C_1$-$C_6$)alkyl), -(heteroaryl)(($C_1$-$C_6$)alkyl), —O$R^5$, and —N($R^5$)$_m$;

$R^{20}$ is selected from the group consisting of ($C_1$-$C_6$)alkyl, —(($C_1$-$C_6$)alkylene)N($R^5$)$_m$, —C(O)(($C_1$-$C_6$)alkylene)N($R^5$)$_m$, —(($C_1$-$C_6$)alkene)(($C_1$-$C_6$)alkyl), —(($C_1$-$C_6$)alkene)(cycloalkyl), —(($C_1$-$C_6$)alkene)(heterocycloalkyl), —O$R^5$, and —N($R^5$)$_m$;

m is 2 or 3; and u is an integer from 0-4;

provided that at least one of $R^3$, $R^6$, $R^9$, or $R^{19}$ comprises a terminal —N($R^5$)$_m$.

In some embodiments, $R^3$ is selected from the group consisting of hydrogen, ($C_1$-$C_6$)alkyl, —(($C_1$-$C_6$)alkylene)N($R^5$)$_m$, —C(O)(($C_1$-$C_6$)alkylene)N($R^5$)$_m$, —O$R^5$, and —N($R^5$)$_m$. In some embodiments, $R^3$ is selected from the group consisting of hydrogen, ($C_1$-$C_6$)alkyl, —O$R^5$, and —N($R^5$)$_m$; and $R^5$ is hydrogen or ($C_1$-$C_6$)alkyl. In some embodiments, $R^3$ is selected from the group consisting of hydrogen, methyl, —OH, and —NH$_2$. In some embodiments, $R^3$ comprises a terminal —N($R^5$)$_m$. In some embodiments, $R^3$ is —(($C_1$-$C_6$)alkylene)N($R^5$)$_m$, —C(O)(($C_1$-$C_6$)alkylene)N($R^5$)$_m$, or —N($R^5$)$_m$. In some embodiments, $R^3$ is —(($C_1$-$C_6$)alkyene)N($R^5$)$_m$ or —N($R^5$)$_m$; and $R^5$ is hydrogen or ($C_1$-$C_6$)alkyl. In some embodiments, $R^3$ is hydrogen.

In some embodiments, $R^9$ is selected from the group consisting of —(($C_1$-$C_6$)alkylene)N($R^5$)$_m$, —O$R^5$, and —N($R^5$)$_m$; and $R^5$ is hydrogen or ($C_1$-$C_6$)alkyl. In some embodiments, $R^9$ is —O$R^5$ or —N($R^5$)$_m$; and $R^5$ is hydrogen or ($C_1$-$C_6$)alkyl. In some embodiments, $R^9$ comprises a terminal —N($R^5$)$_m$. In some embodiments, $R^9$ is —(($C_1$-$C_6$)alkylene)N($R^5$)$_m$ or —N($R^5$)$_m$. In some embodiments, $R^9$ is —OH.

In some embodiments, $R^{10}$ is ($C_1$-$C_6$)alkyl or cycloalkyl. In some embodiments, $R^{10}$ is ($C_1$-$C_6$)alkyl. In some embodiments, $R^{10}$ is methyl.

In some embodiments, $R^{18}$ is selected from the group consisting of ($C_1$-$C_6$)alkyl, ($C_2$-$C_6$)alkenyl, ($C_2$-$C_6$)alkynyl, —(($C_1$-$C_6$)alkylene)N($R^5$)$_m$, —C(O)(($C_1$-$C_6$)alkylene)N($R^5$)$_m$, cycloalkyl, heterocycloalkyl, aryl, heteroaryl, aralkyl, and heteroaralkyl. In some embodiments, $R^{18}$ is selected from the group consisting of ($C_1$-$C_6$)alkyl, ($C_2$-$C_6$)alkenyl, ($C_2$-$C_6$)alkynyl, cycloalkyl, heterocycloalkyl, aryl, heteroaryl, aralkyl, and heteroaralkyl. In some embodiments, $R^{18}$ is selected from the group consisting of ($C_1$-$C_6$)alkyl, ($C_2$-$C_6$)alkenyl, aryl, heteroaryl, aralkyl, and heteroaralkyl.

In some embodiments, $R^{18}$ comprises a terminal —N($R^5$)$_m$.

In some embodiments, $R^{18}$ is represented by $$\{-L-Y-(R^{20})_u;$$

L is a covalent bond or —(($C_1$-$C_6$)alkylene)-;

Y is selected from the group consisting of cycloalkyl, heterocycloalkyl, aryl, and heteroaryl;

$R^{20}$ is selected from the group consisting of ($C_1$-$C_6$)alkyl, —(($C_1$-$C_6$)alkylene)N($R^5$)$_m$, —C(O)(($C_1$-$C_6$)alkylene)N($R^5$)$_m$, —(($C_1$-$C_6$)alkene)(($C_1$-$C_6$)alkyl), —(($C_1$-$C_6$)alkene)(cycloalkyl), —(($C_1$-$C_6$)alkene)(heterocycloalkyl), —O$R^5$, and —N($R^5$)$_m$; and u is an integer from 0-4.

In some embodiments, $R^{20}$ is —(($C_1$-$C_6$)alkene)(($C_1$-$C_6$)alkyl) or —(($C_1$-$C_6$)alkene)(cycloalkyl). In some embodiments, $R^{20}$ comprises a terminal —N($R^5$)$_m$. In some embodiments, $R^{20}$ is —(($C_1$-$C_6$)alkylene)N($R^5$)$_m$, —C(O)(($C_1$-$C_6$)alkylene)N($R^5$)$_m$, or —N($R^5$)$_m$.

In some embodiments, $R^{19}$ is selected from the group consisting of ($C_1$-$C_6$)alkyl, —(($C_1$-$C_6$)alkylene)N($R^5$)$_m$, —C(O)((C$_1$-C$_6$)alkylene)N(R$^5$)$_m$, -(cycloalkyl)((C$_1$-C$_6$)alkyl), -(heterocycloalkyl)((C$_1$-C$_6$)alkyl), -(aryl)((C$_1$-C$_6$)alkyl), -(heteroaryl)((C$_1$-C$_6$)alkyl), —OR$^5$, and —N(R$^5$)$_m$. In some embodiments, R$^{19}$ is selected from the group consisting of (C$_1$-C$_6$)alkyl, —((C$_1$-C$_6$)alkylene)N(R$^5$)$_m$, -(heterocycloalkyl)((C$_1$-C$_6$)alkyl), -(heteroaryl)((C$_1$-C$_6$)alkyl), and —N(R$^5$)$_m$.

In some embodiments, R$^{19}$ comprises a terminal —N(R$^5$)$_m$. In some embodiments, R$^{19}$ is —((C$_1$-C$_6$)alkylene)N(R$^5$)$_m$, —C(O)((C$_1$-C$_6$)alkylene)N(R$^5$)$_m$, or —N(R$^5$)$_m$.

In some embodiments, m is 2. In some embodiments, m is 3.

In some embodiments, the compound of formula (VIII) is selected from the group consisting of:

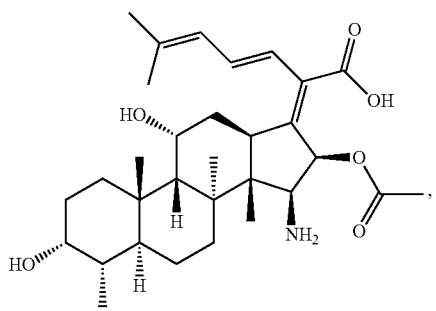

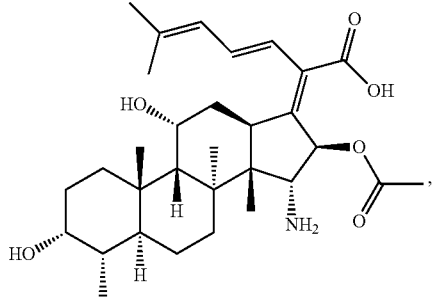

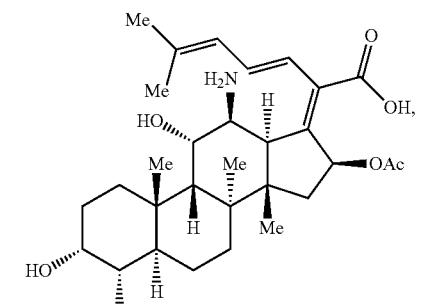

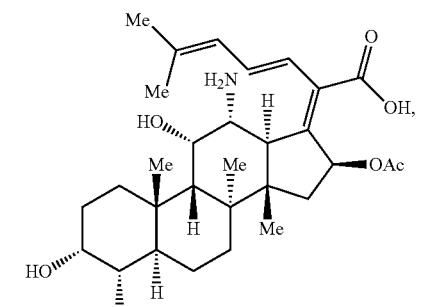

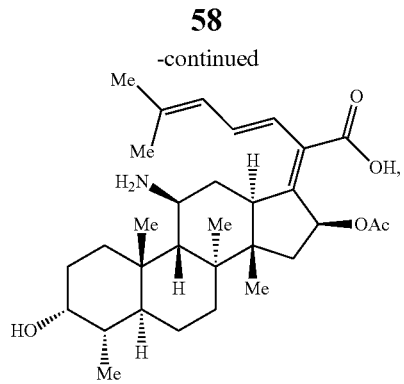

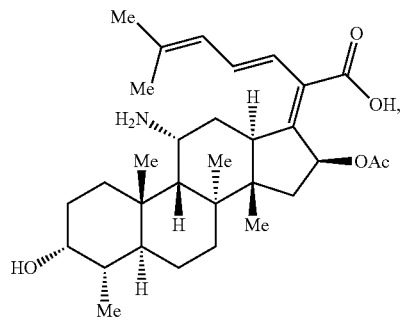

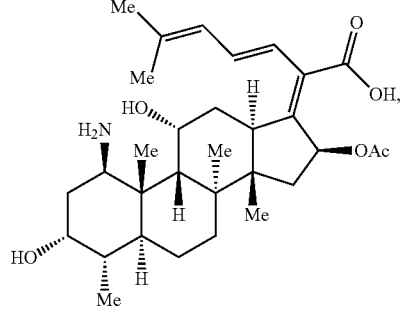

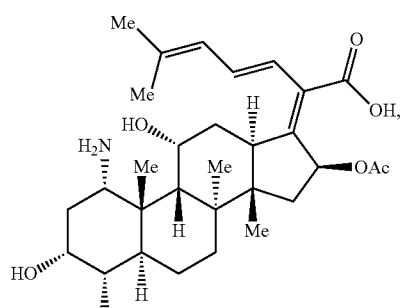

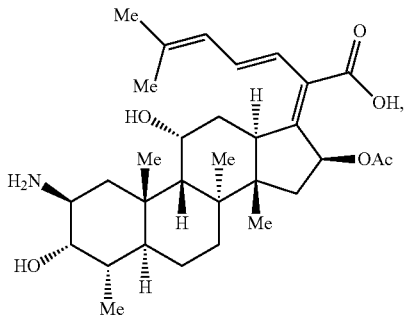

-continued
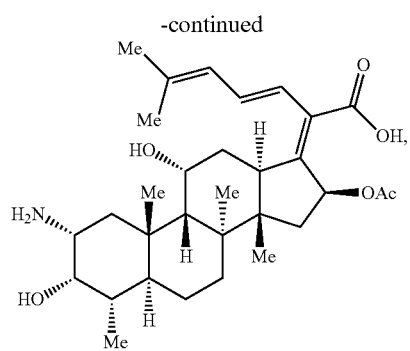
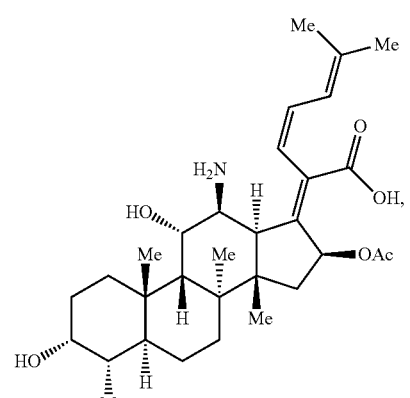
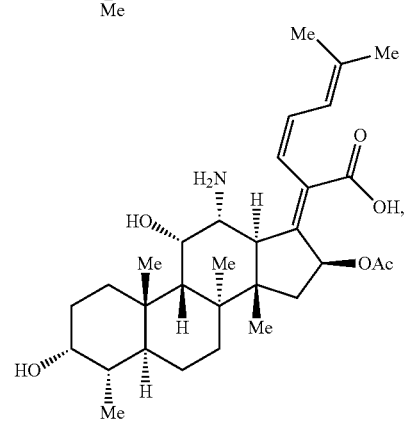
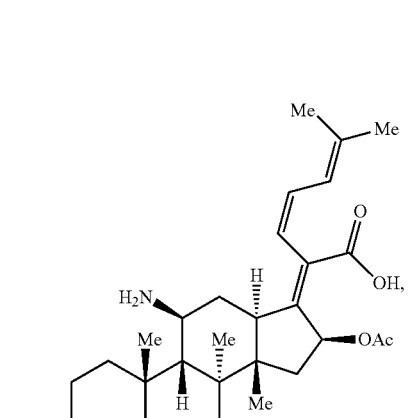
-continued
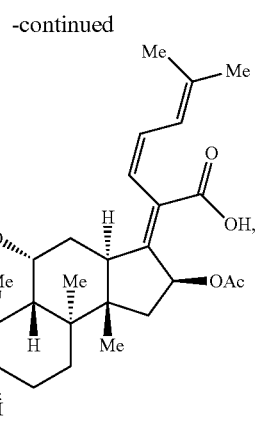
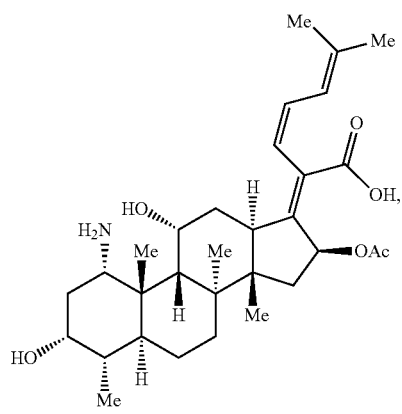
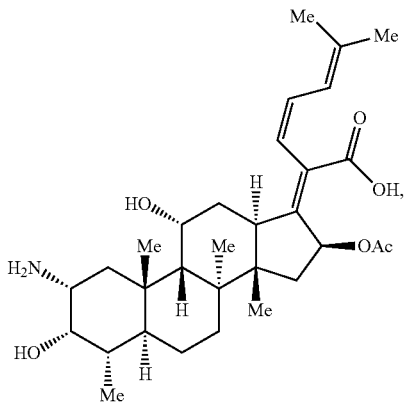
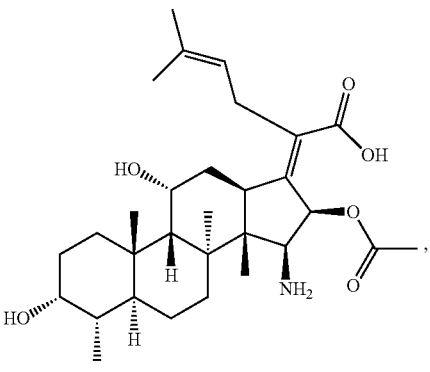
RB:5
PBF:1.14

-continued
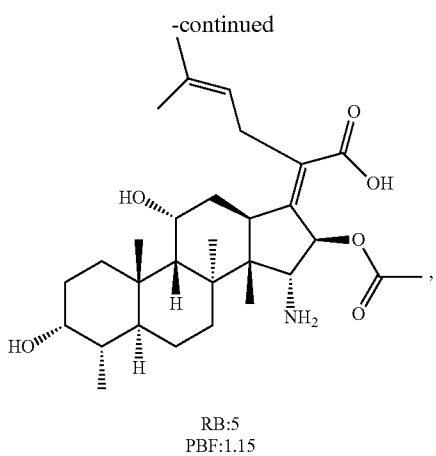
RB:5
PBF:1.15
-continued
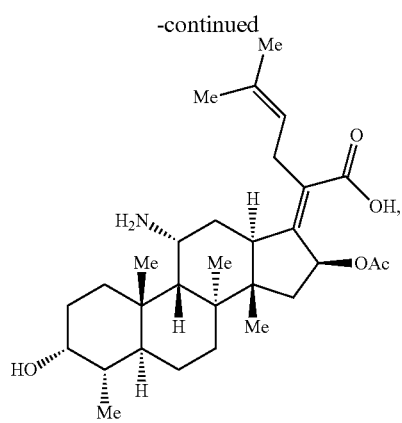
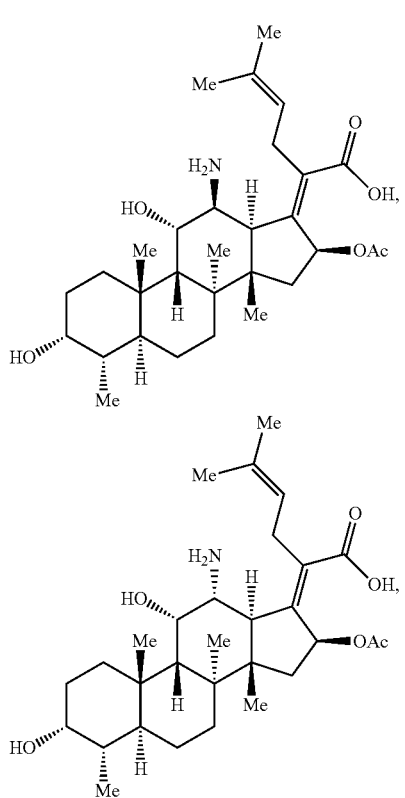
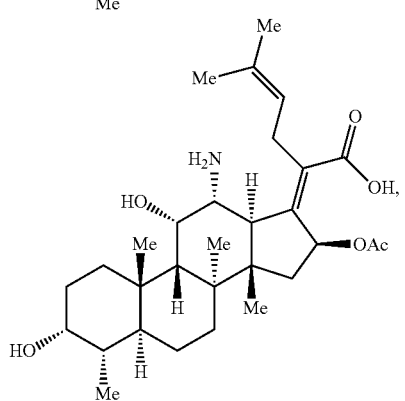
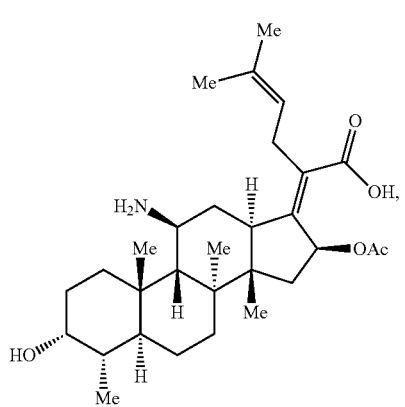
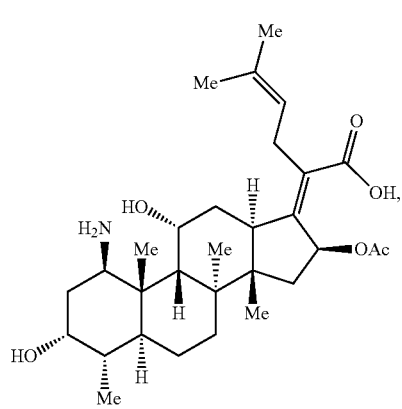
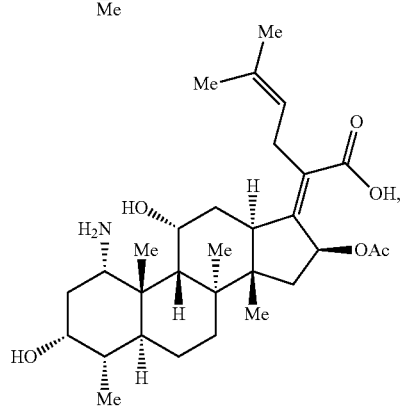
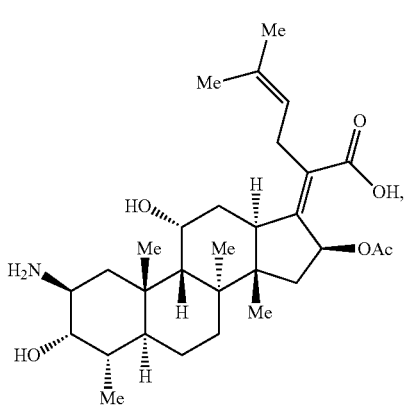

63
-continued
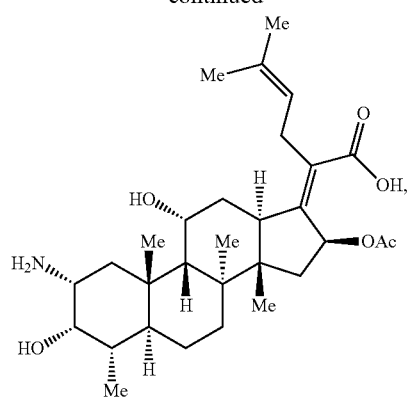
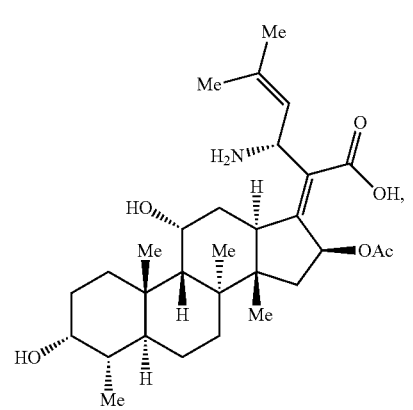
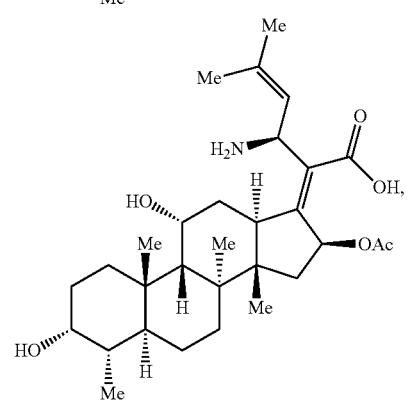
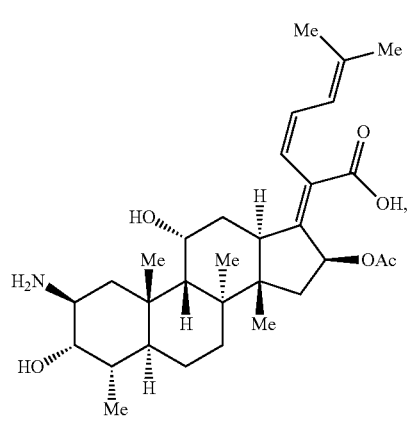
64
-continued
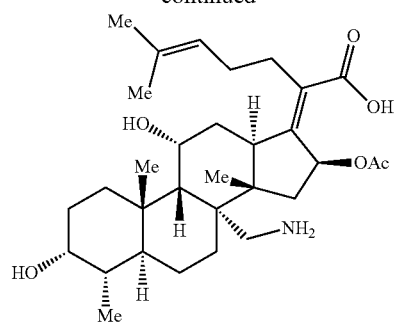
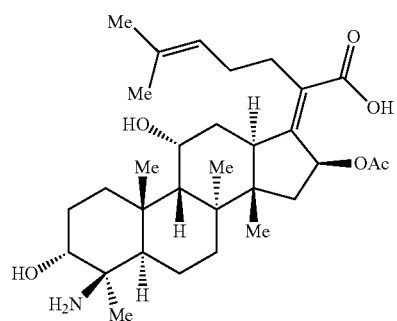
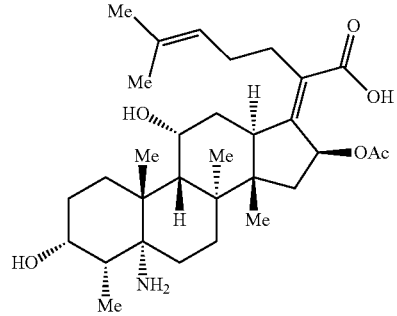
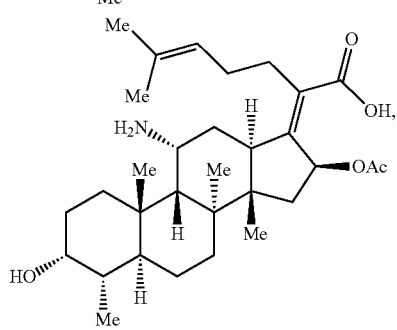
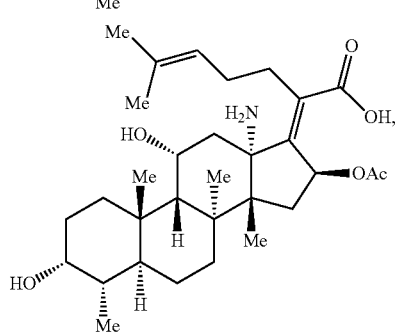

65
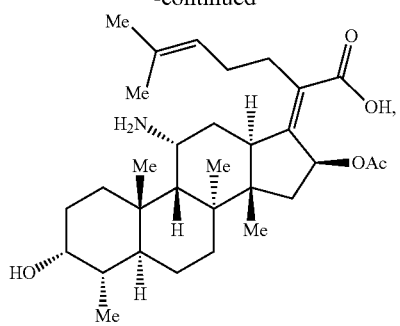
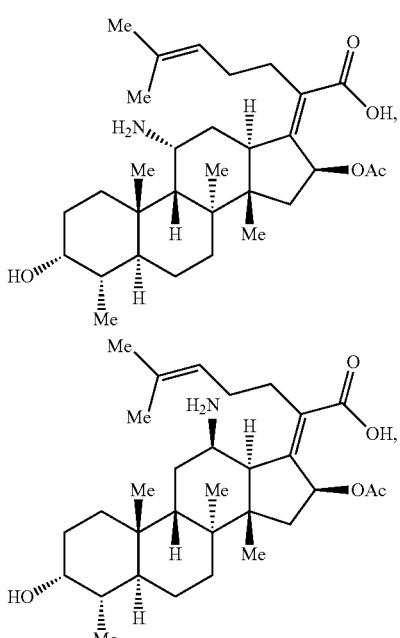
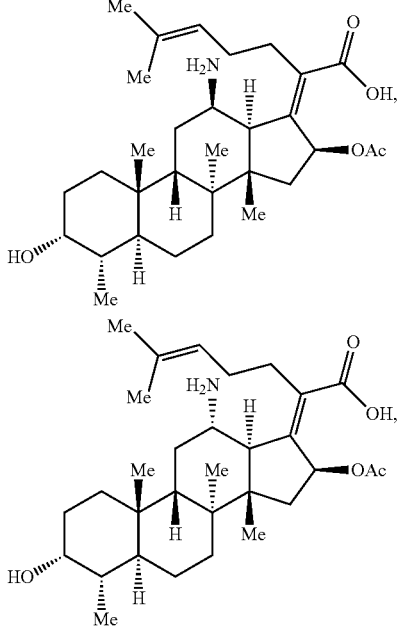
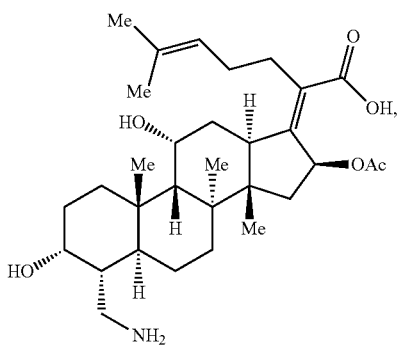
66
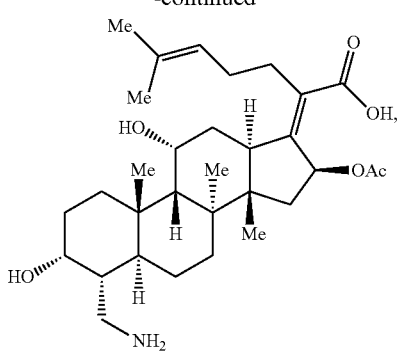
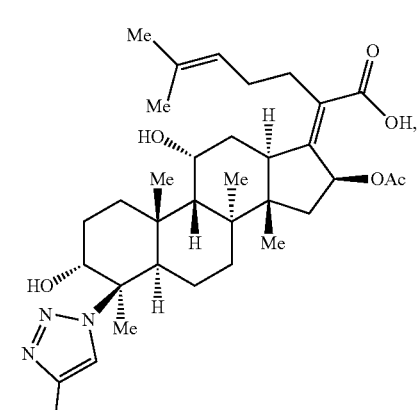
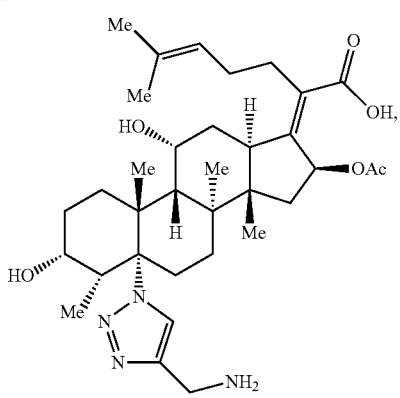
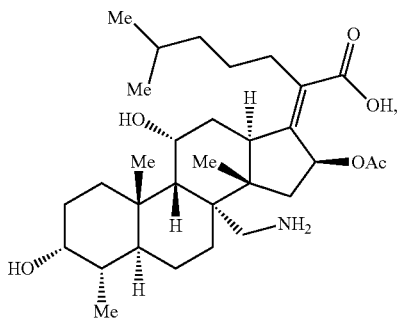

| 67 | 68 |
|---|---|
| -continued | -continued |
| 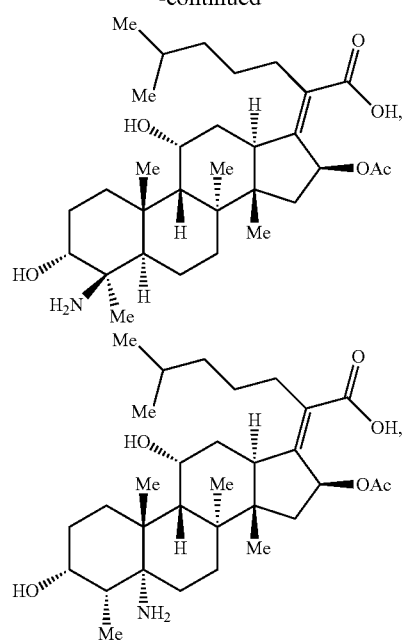 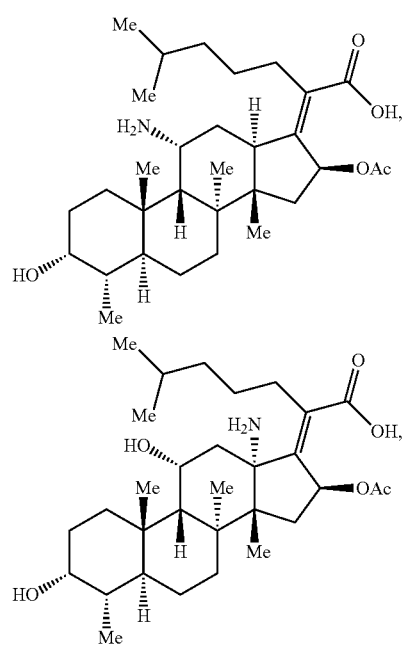 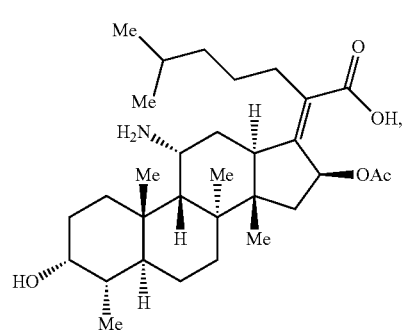 | 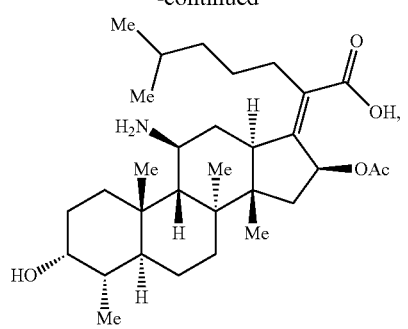 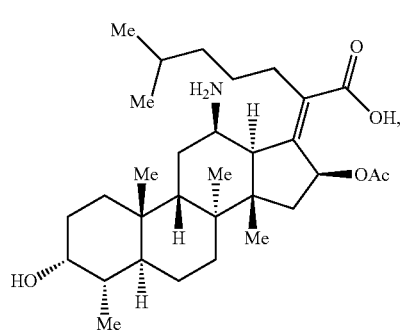 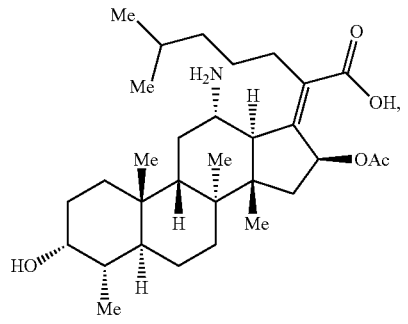 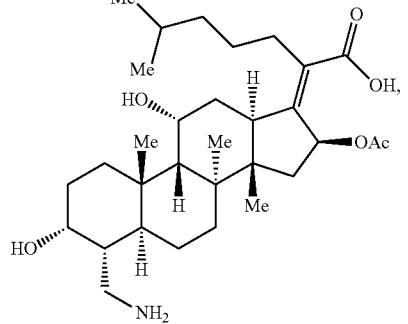 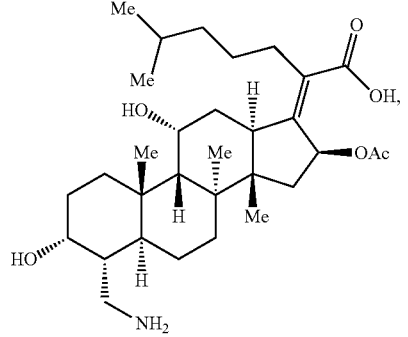 |

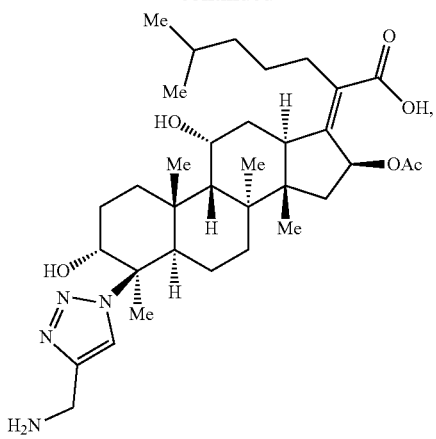
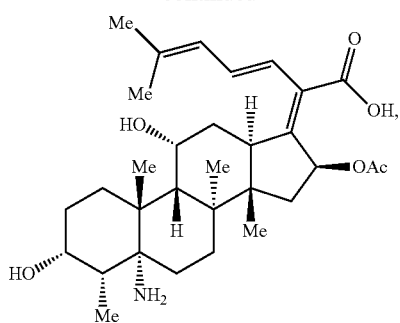

71
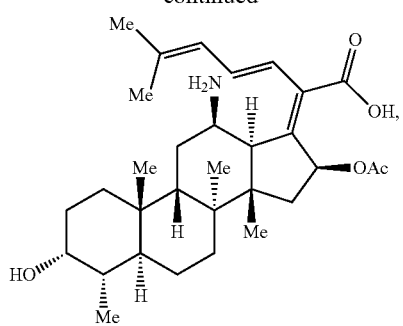
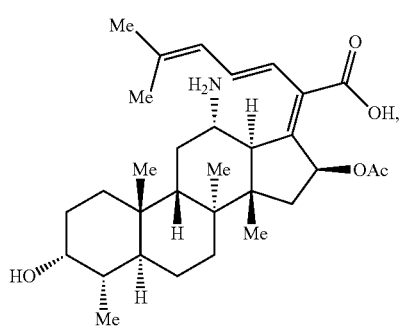
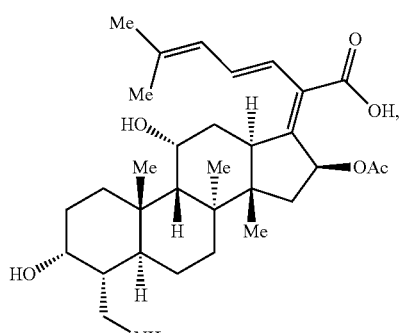
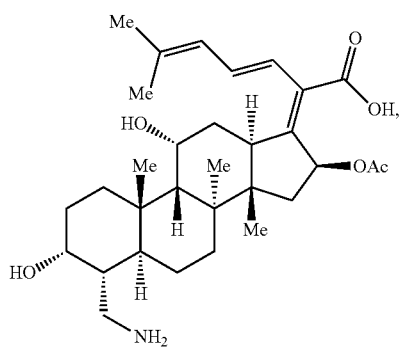
72
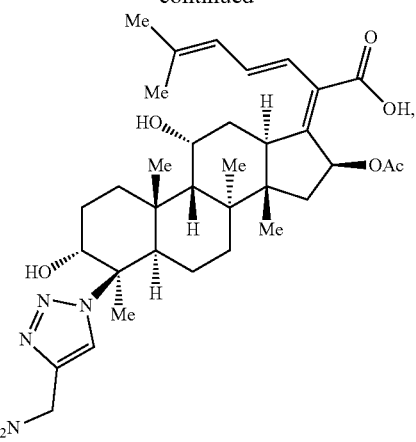
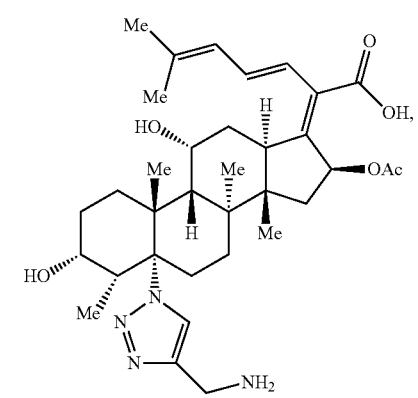
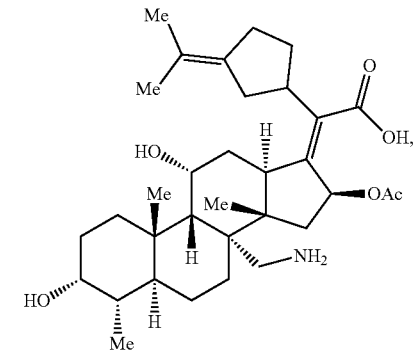
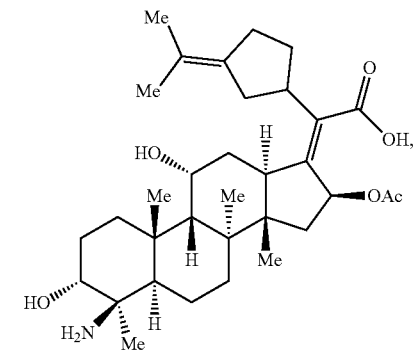

73
-continued
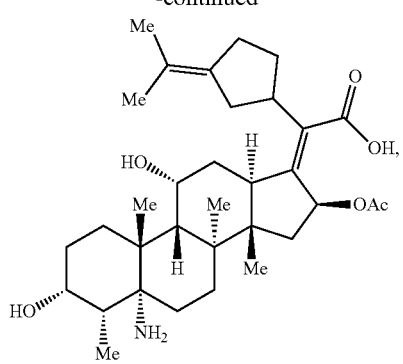
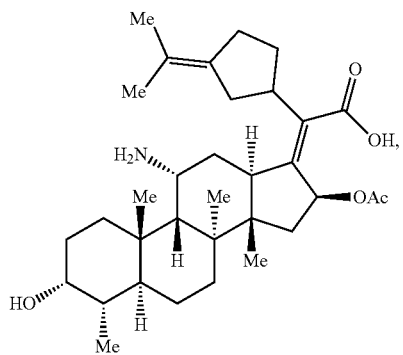
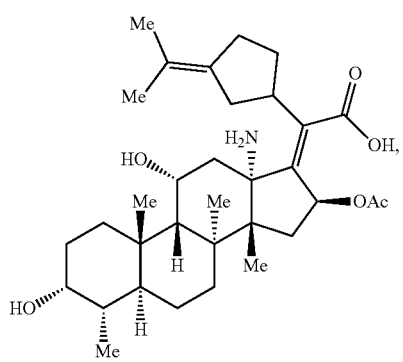
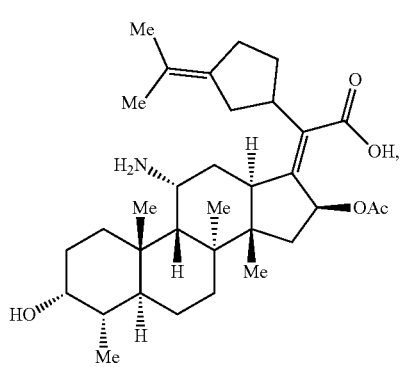
74
-continued
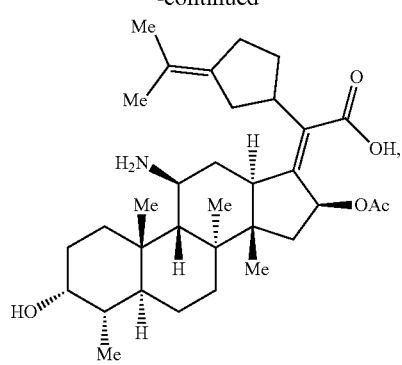
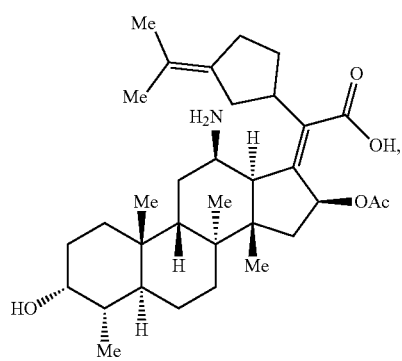
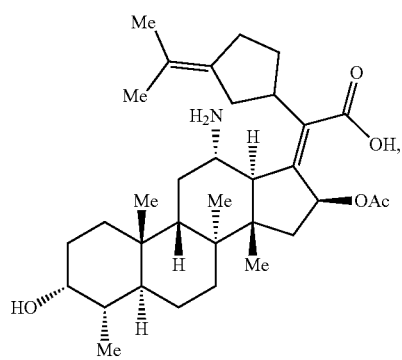
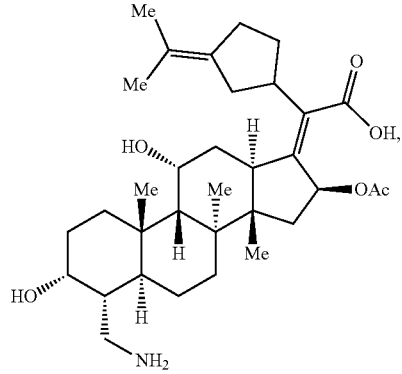

75
-continued
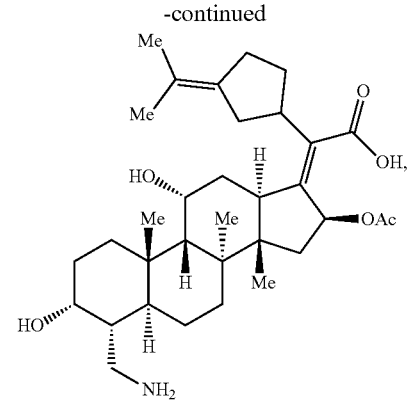
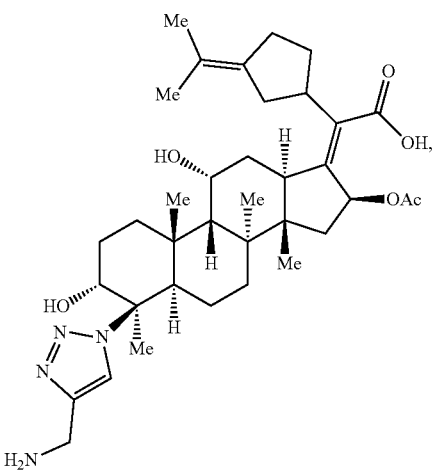
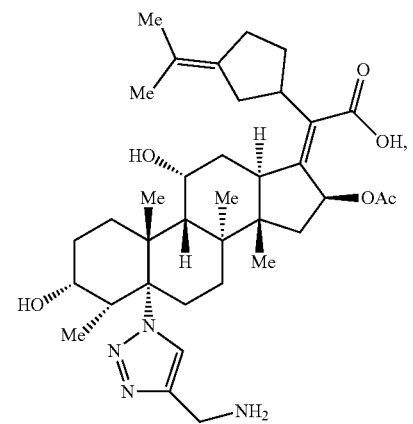
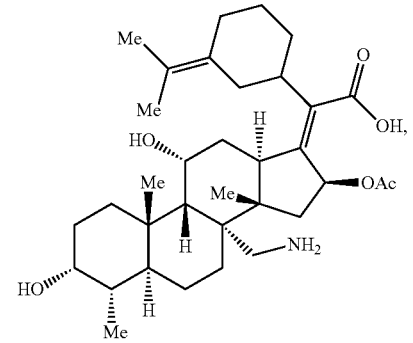
76
-continued
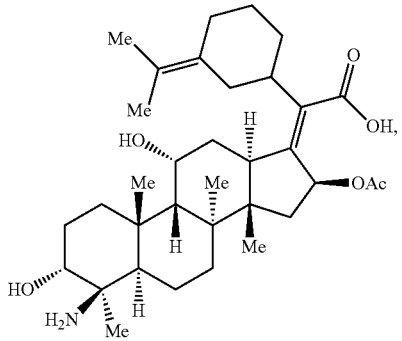
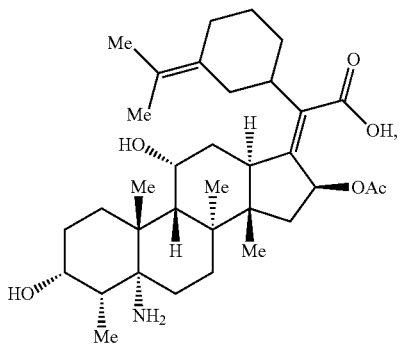
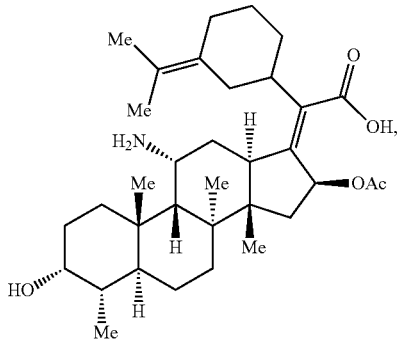
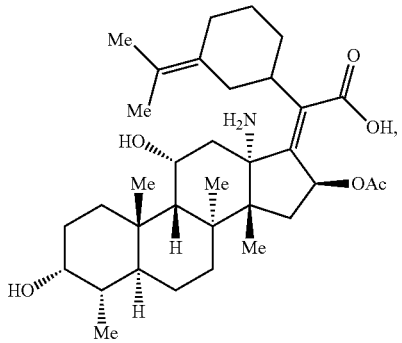
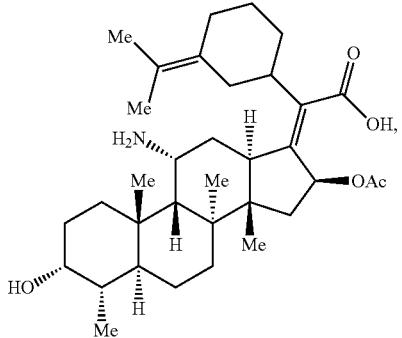

77
-continued
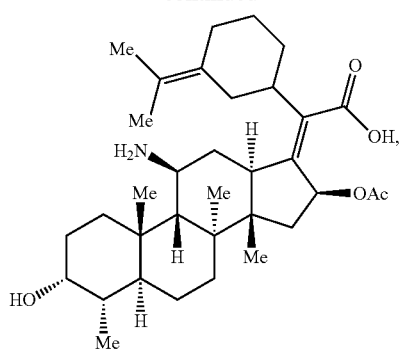
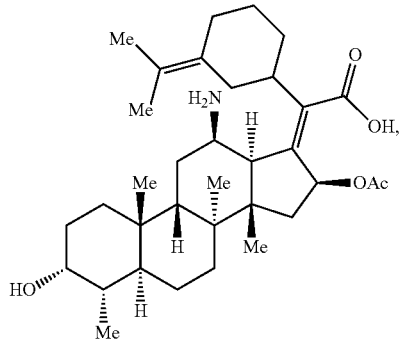
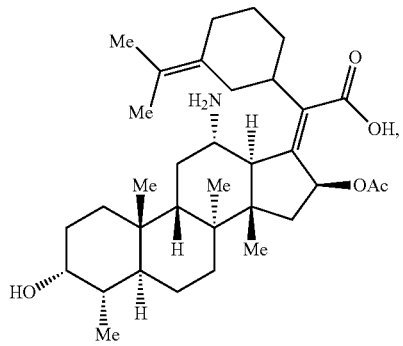
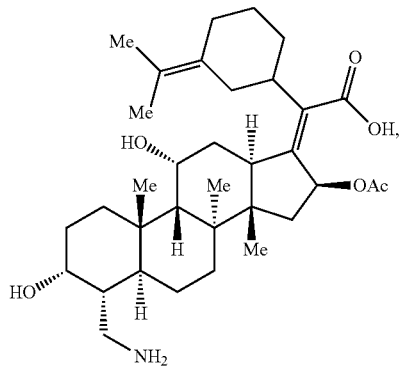
78
-continued
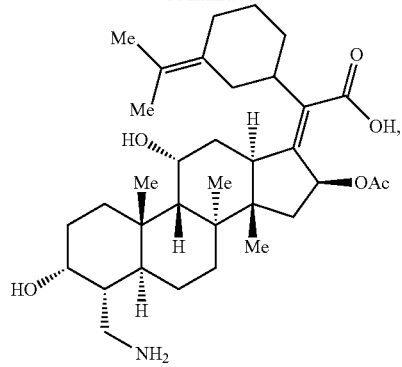
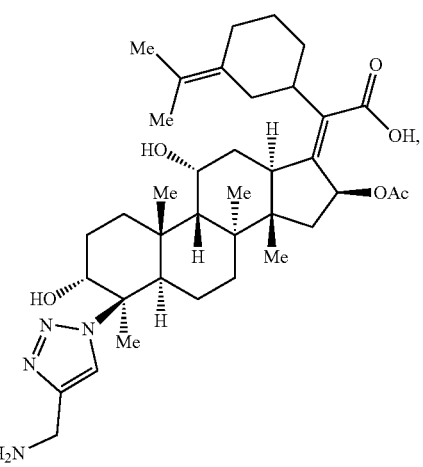
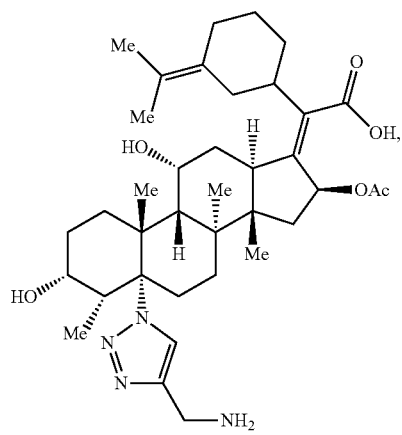
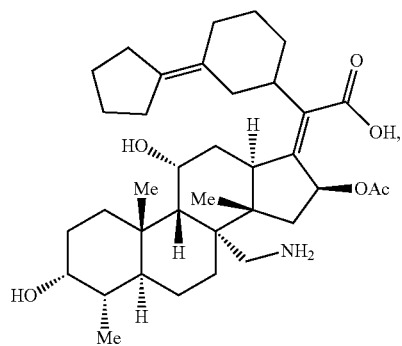

79
-continued
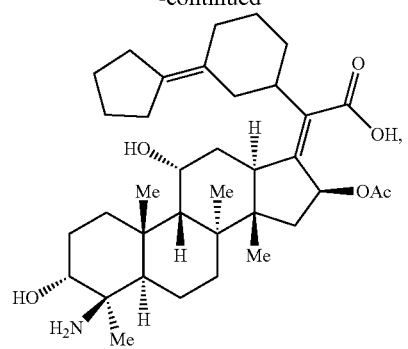
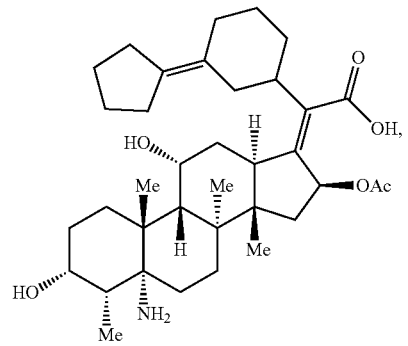
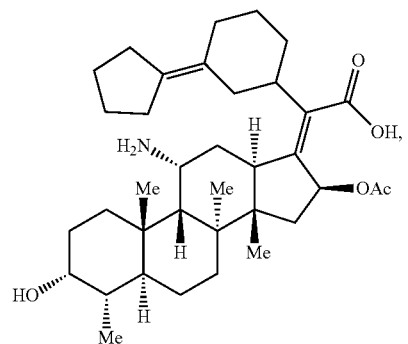
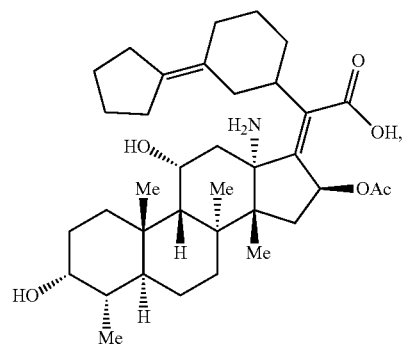
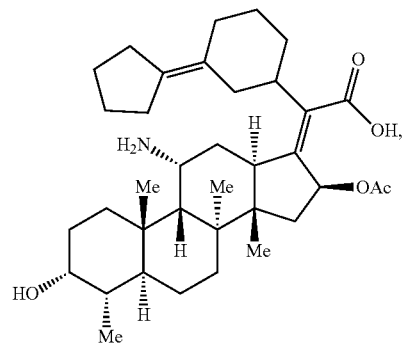
80
-continued
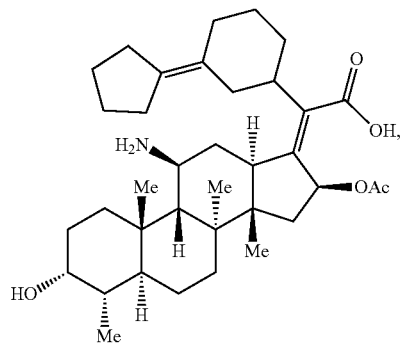
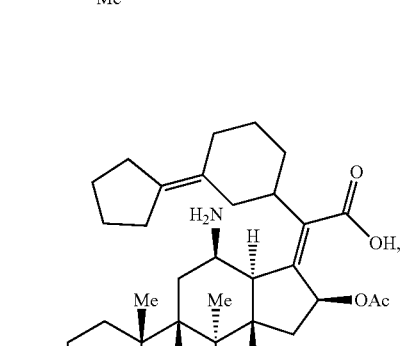
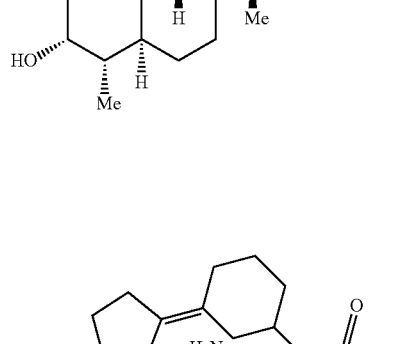
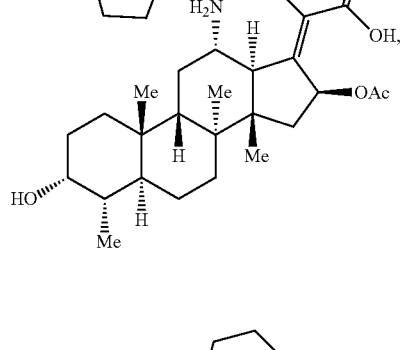
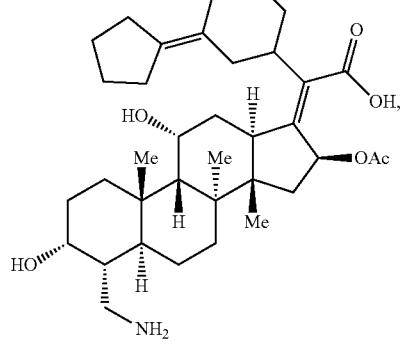

81
-continued
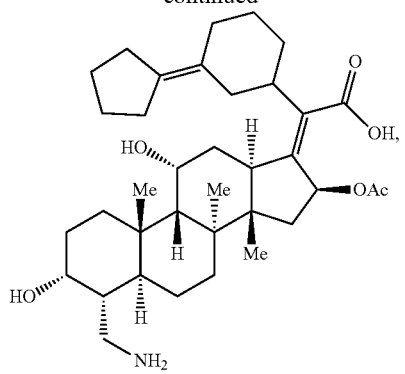
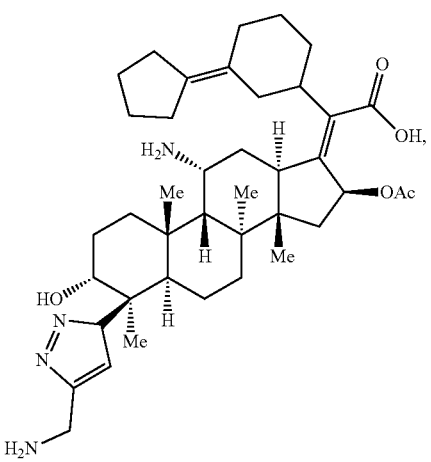
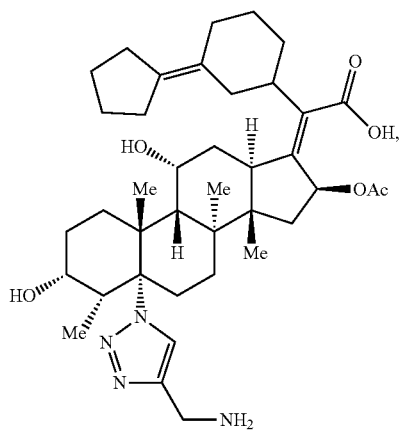
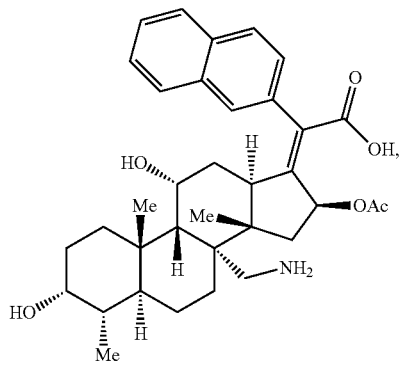
82
-continued
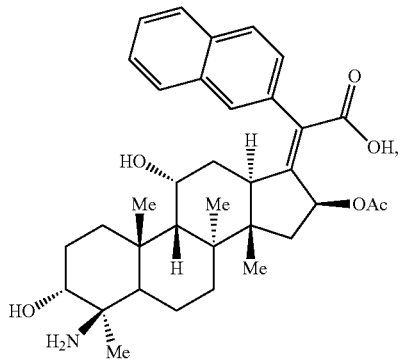
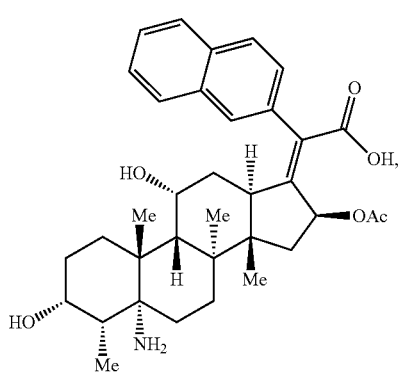
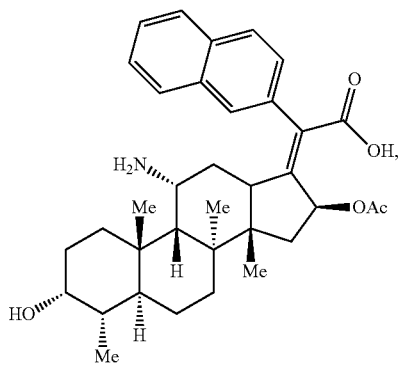
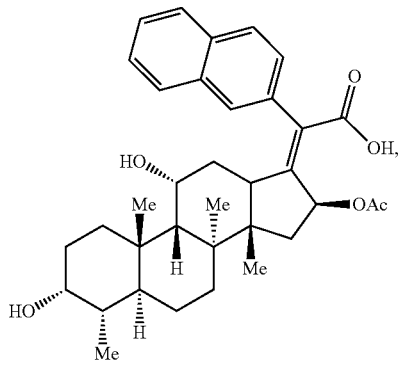

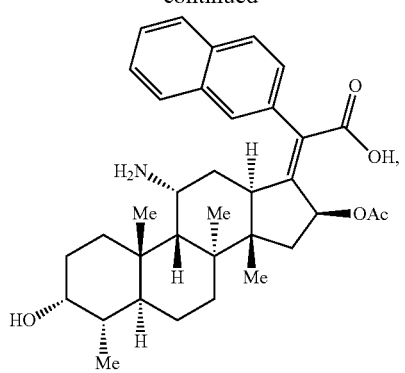
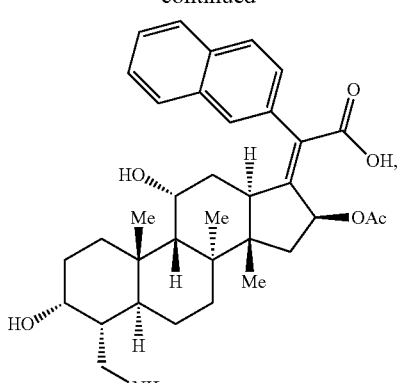
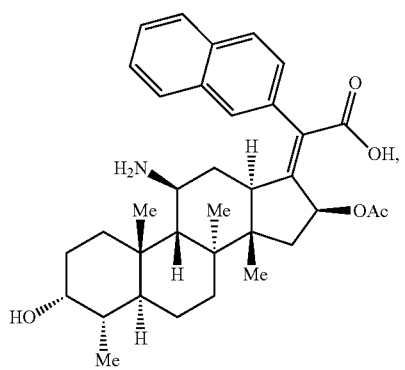
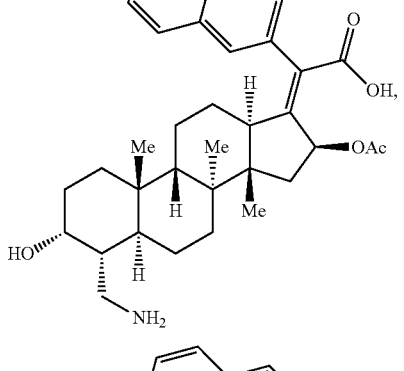
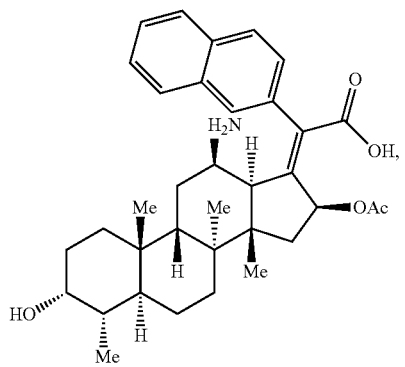
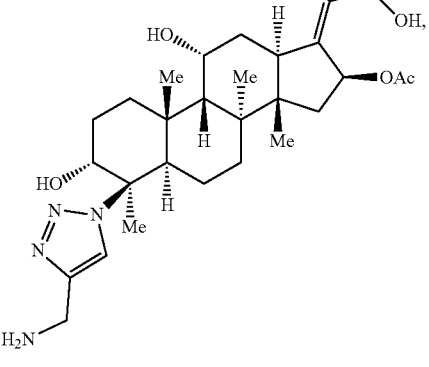
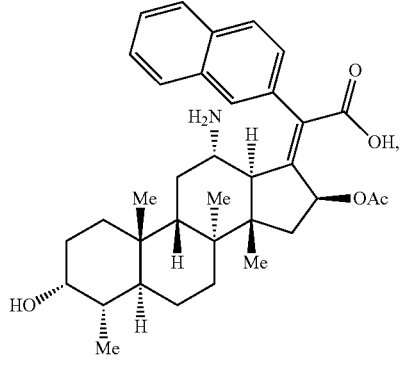
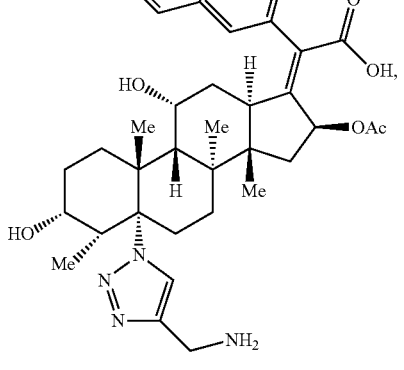

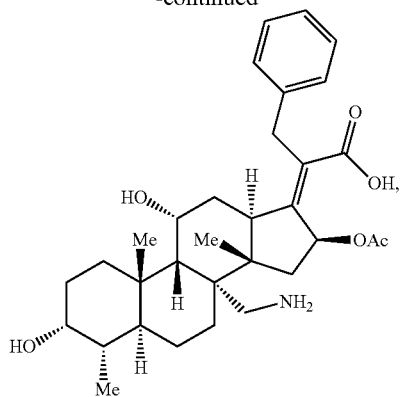
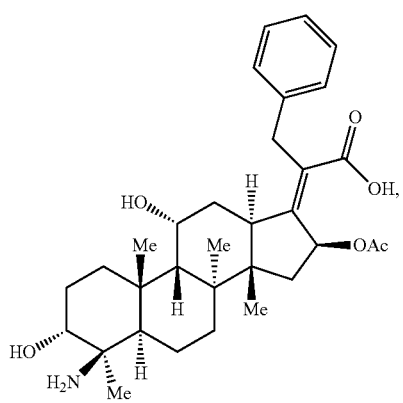
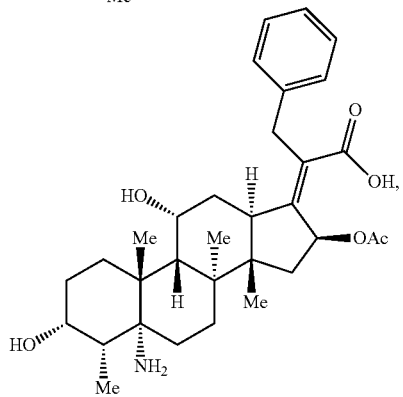
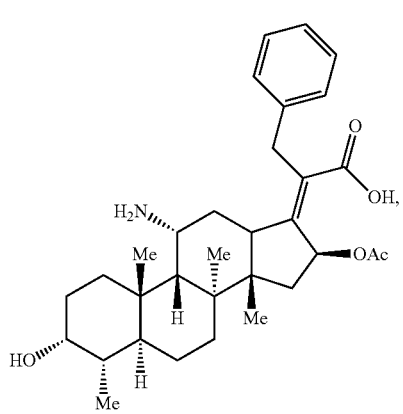
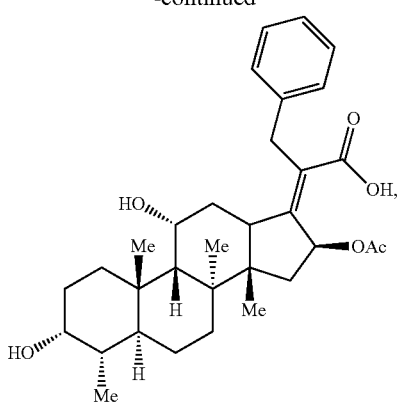
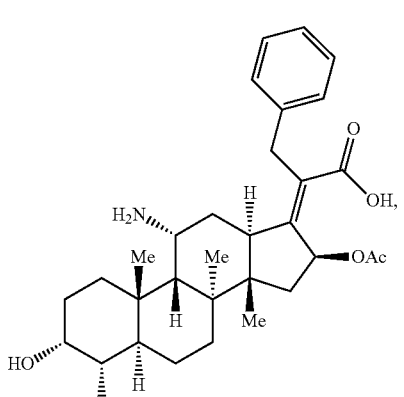
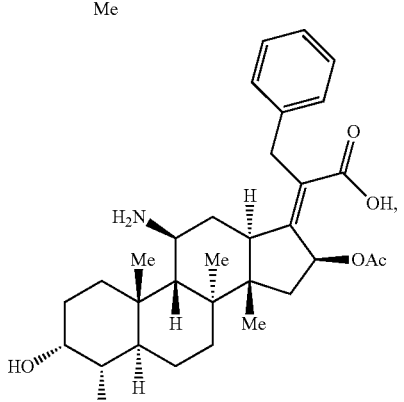
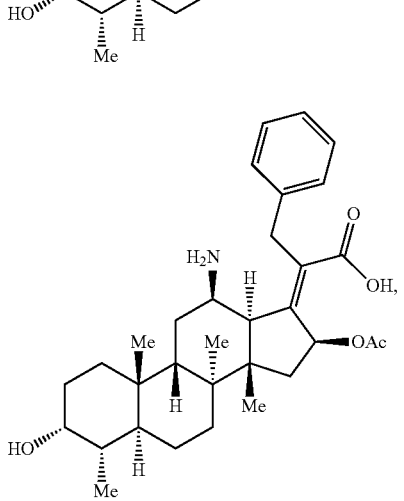

87
-continued
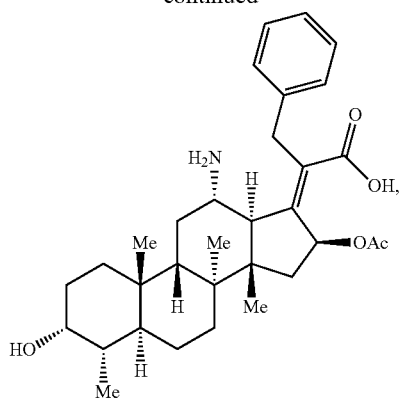
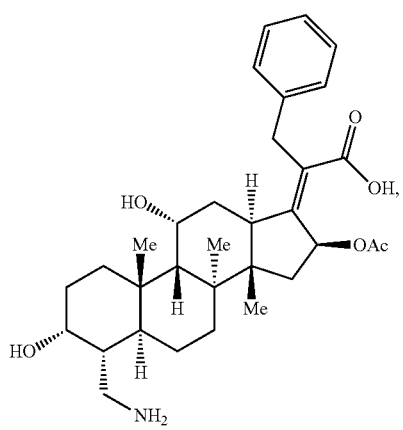
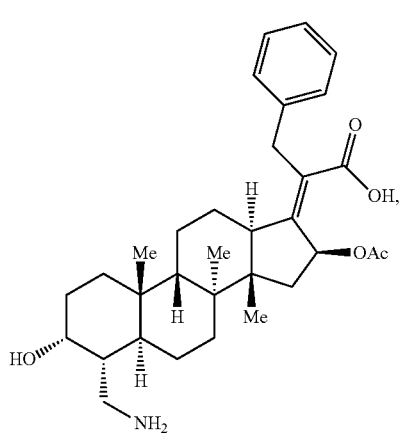
88
-continued
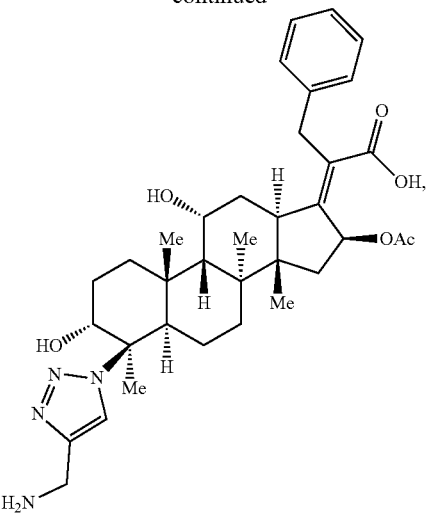
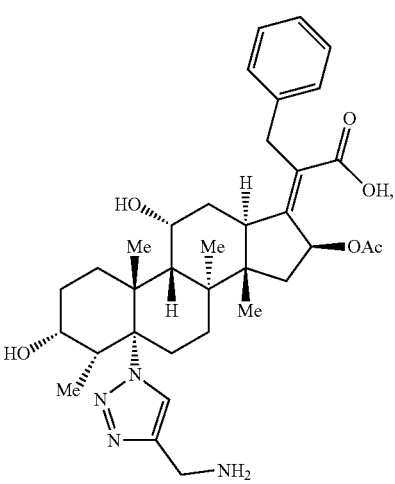
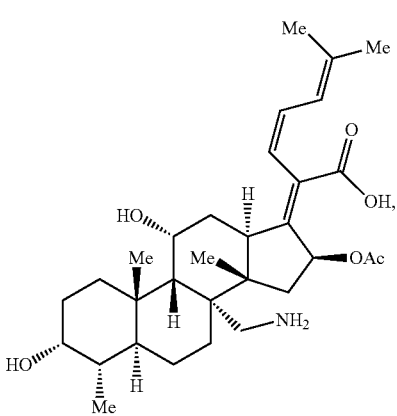

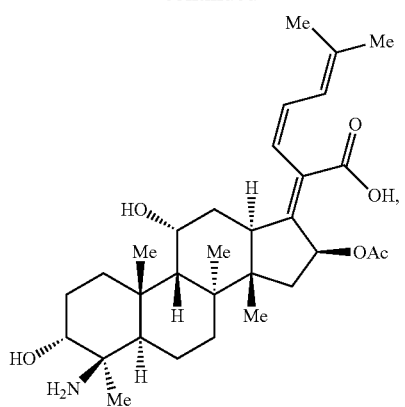
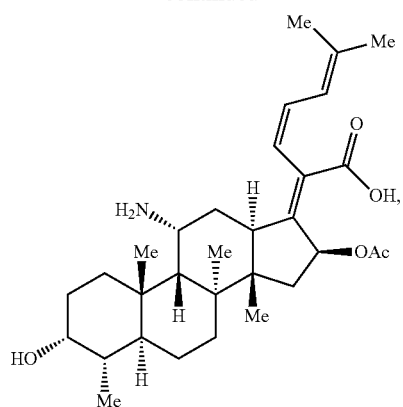
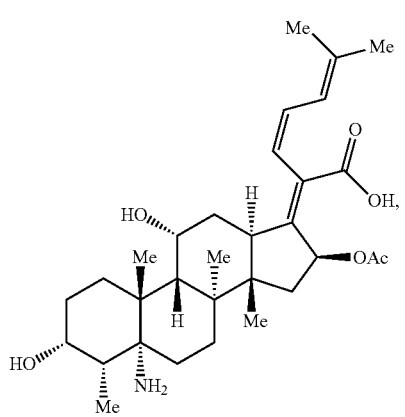
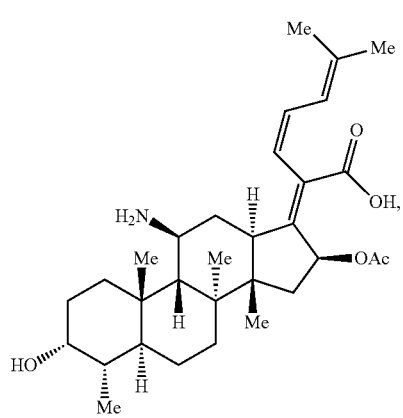
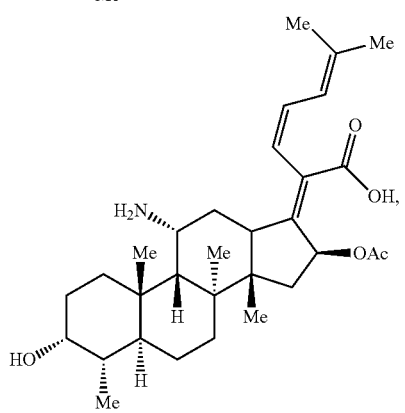
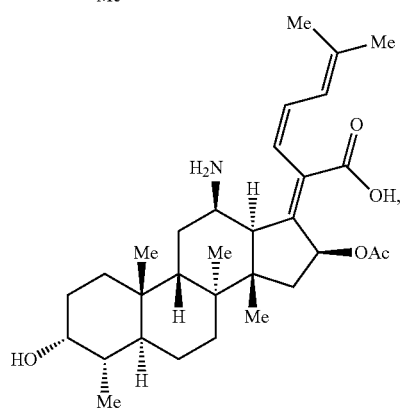
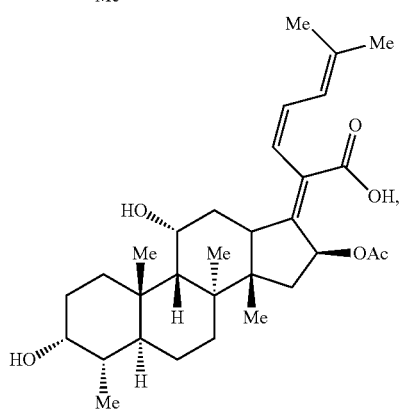
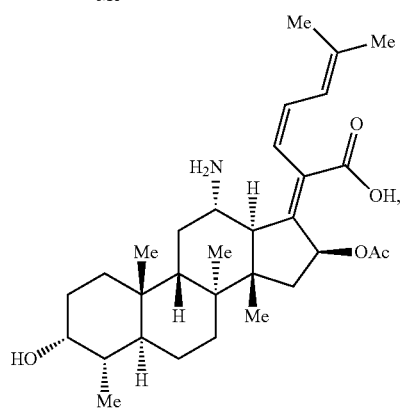

91
-continued

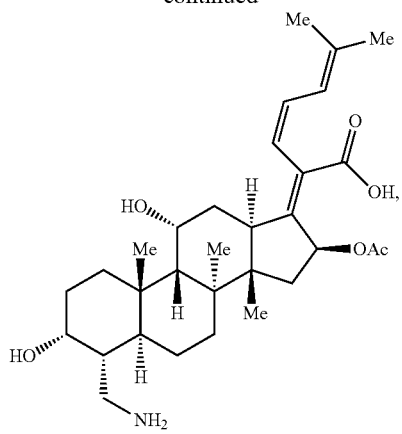

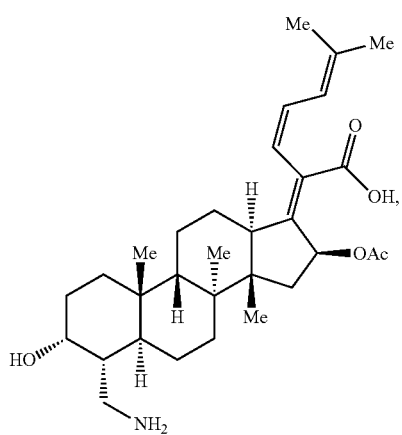

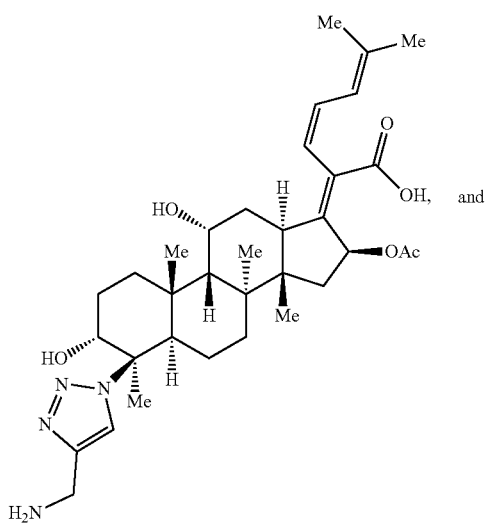

92
-continued

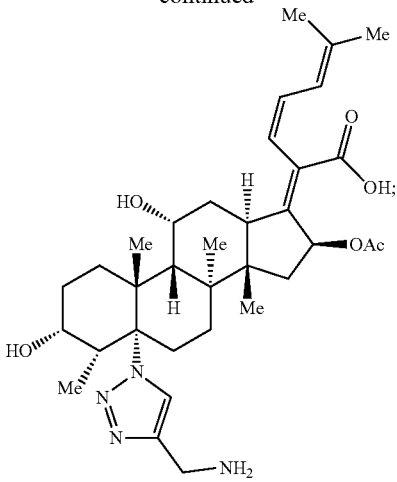

or a pharmaceutically acceptable salt thereof.

Exemplary Deoxynybomycin Derivatives

In some embodiments of the compounds disclosed herein, the compound is a derivative or analog of deoxynybomycin, wherein deoxynybomycin is

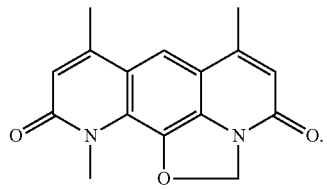 [SMILES: Cc1cc(=O)n(C)c2c3c4c(cc12)c(C)cc(=O)n4CO3]

The compounds disclosed herein exclude deoxynybomycin.

In some embodiments, the compound has RB of 2 or less and a Glob of 0.12 or less. In some embodiments, the compound has RB of 2 or less and a Glob of 0.1 or less. In some embodiments, the compound has RB of 1 and a Glob of about 0.09.

In some embodiments, the compound is represented by Formula (IX) or a pharmaceutically acceptable salt thereof:

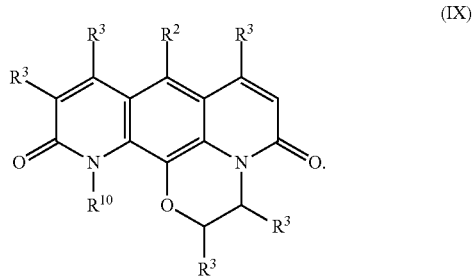

wherein, independently for each occurrence:

$R^2$ is selected from the group consisting of hydrogen, halogen, —CN, $(C_1-C_6)$alkyl optionally substituted with 1, 2, or 3 halogen atoms, cycloalkyl, heterocycloalkyl, aryl, heteroaryl, aralkyl, heteroaralkyl, —C(O)OR$^5$, —OR$^5$, SR$^5$, —S(O)R$^5$, —SO$_2$R$^5$, —SO$_2$NR$^5$, —NO$_2$, —N$_3$, and —N(R$^5$)$_m$;

$R^3$ is selected from the group consisting of hydrogen, halogen, —CN, $(C_1-C_6)$alkyl optionally substituted with 1, 2, or 3 halogen atoms, —((C$_1$-C$_6$)alkylene)N(R$^5$)$_m$, —C(O)((C$_1$-C$_6$)alkylene)N(R$^5$)$_m$, cycloalkyl, heterocycloalkyl, aryl, heteroaryl, aralkyl, heteroaralkyl, —C(O)OR$^5$, —OR$^5$, —O((C$_1$-C$_6$)alkylene)N(R$^5$)$_m$, —SR$^5$, —S(O)R$^5$, —SO$_2$R$^5$, —SO$_2$NR$^5$, —NO$_2$, —N$_3$, and —N(R$^5$)$_m$;

R$^5$ is selected from the group consisting of hydrogen, (C$_1$-C$_6$)alkyl optionally substituted with 1, 2, or 3 halogen atoms, cycloalkyl, heterocycloalkyl, aryl, heteroaryl, aralkyl, and heteroaralkyl;

R$^{10}$ is selected from the group consisting of (C$_1$-C$_6$)alkyl, cycloalkyl, heterocycloalkyl, aryl, heteroaryl, aralkyl, and heteroaralkyl; and m is 2 or 3; and provided that at least one of R$^2$ or R$^3$ comprises a terminal —N(R$^5$)$_m$.

In some embodiments, independently for each occurrence:

R$^2$ is selected from the group consisting of hydrogen, halogen, (C$_1$-C$_6$)alkyl, —OR$^5$, and —N(R$^5$)$_m$;

R$^3$ is selected from the group consisting of hydrogen, (C$_1$-C$_6$)alkyl, —((C$_1$-C$_6$)alkylene)N(R$^5$)$_m$, —C(O)((C$_1$-C$_6$)alkylene)N(R$^5$)$_m$, —OR$^5$, and —N(R$^5$)$_m$;

R$^5$ is hydrogen or (C$_1$-C$_6$)alkyl;

R$^{10}$ is (C$_1$-C$_6$)alkyl or cycloalkyl; and m is 2 or 3.

In some embodiments, R$^2$ is selected from the group consisting of hydrogen, halogen, —CN, (C$_1$-C$_6$)alkyl optionally substituted with 1, 2, or 3 halogen atoms, cycloalkyl, heterocycloalkyl, aryl, heteroaryl, aralkyl, heteroaralkyl, —C(O)OR$^5$, —OR$^5$, SR$^5$, —S(O)R$^5$, —SO$_2$R$^5$, —SO$_2$NR$^5$, —NO$_2$, —N$_3$, and —N(R$^5$)$_m$; and R$^5$ is hydrogen or (C$_1$-C$_6$)alkyl. In some embodiments, R$^2$ is selected from the group consisting of hydrogen, halogen, (C$_1$-C$_6$)alkyl, —OR$^5$, and —N(R$^5$)$_m$; and R$^5$ is hydrogen or (C$_1$-C$_6$)alkyl. In some embodiments, R$^2$ comprises a terminal —N(R$^5$)$_m$. In some embodiments, R$^2$ is —N(R$^5$)$_m$. In some embodiments, R$^2$ is hydrogen.

In some embodiments, R$^3$ is selected from the group consisting of hydrogen, halogen, —CN, (C$_1$-C$_6$)alkyl optionally substituted with 1, 2, or 3 halogen atoms, —((C$_1$-C$_6$)alkylene)N(R$^5$)$_m$, —C(O)((C$_1$-C$_6$)alkylene)N(R$^5$)$_m$, cycloalkyl, heterocycloalkyl, aryl, heteroaryl, aralkyl, heteroaralkyl, —C(O)OR$^5$, —OR$^5$, —O((C$_1$-C$_6$)alkylene)N(R$^5$)$_m$, —SR$^5$, —S(O)R$^5$, —SO$_2$R$^5$, —SO$_2$NR$^5$, —NO$_2$, —N$_3$, and —N(R$^5$)$_m$; and R$^5$ is hydrogen or (C$_1$-C$_6$)alkyl. In some embodiments, R$^3$ is selected from the group consisting of hydrogen, (C$_1$-C$_6$)alkyl, —((C$_1$-C$_6$)alkylene)N(R$^5$)$_m$, and —N(R$^5$)$_m$; and R$^5$ is hydrogen or (C$_1$-C$_6$)alkyl. In some embodiments, R$^3$ is selected from the group consisting of hydrogen, methyl, ethyl, —CH$_2$—NH$_2$, or —CH$_2$(NH)CH$_3$. In some embodiments, R$^3$ comprises a terminal —N(R$^5$)$_m$. In some embodiments, R$^3$ is —((C$_1$-C$_6$)alkylene)N(R$^5$)$_m$, —C(O)((C$_1$-C$_6$)alkylene)N(R$^5$)$_m$, or —N(R$^5$)$_m$. In some embodiments, R$^3$ is —((C$_1$-C$_6$)alkyene)N(R$^5$)$_m$.

In some embodiments, R$^5$ is hydrogen or (C$_1$-C$_6$)alkyl optionally substituted with 1, 2, or 3 halogen atoms.

In some embodiments, the compound of formula (IX) is represented by Formula (IXa) or a pharmaceutically acceptable salt thereof:

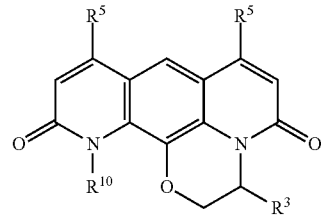

(IXa)

wherein, independently for each occurrence:

R$^3$ is —((C$_1$-C$_6$)alkylene)N(R$^5$)$_m$ or —N(R$^5$)$_m$;

R$^5$ is hydrogen or (C$_1$-C$_6$)alkyl;

R$^{10}$ is (C$_1$-C$_6$)alkyl or cycloalkyl; and m is 2 or 3.

In some embodiments, m is 2. In some embodiments, m is 3.

In some embodiments, the compound of formula (IX) is selected from the group consisting of:

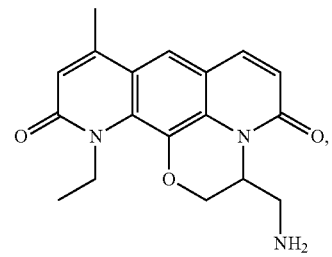

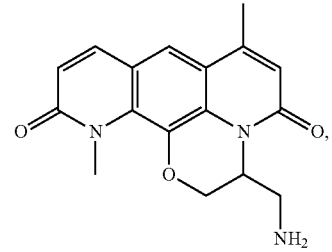

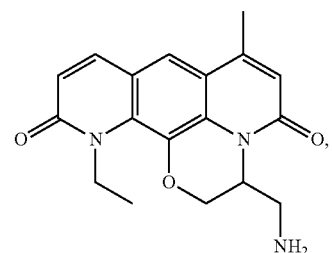

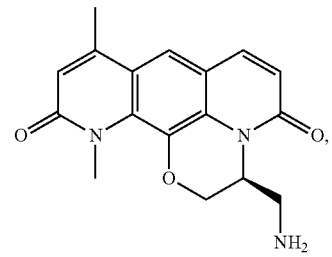

95
-continued
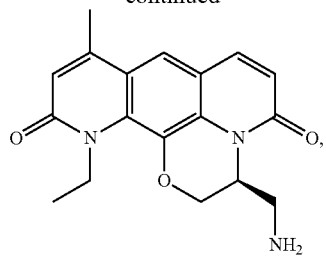
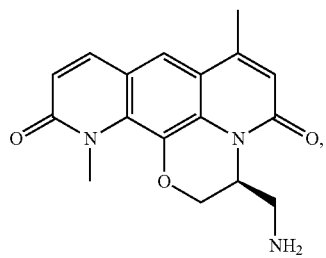
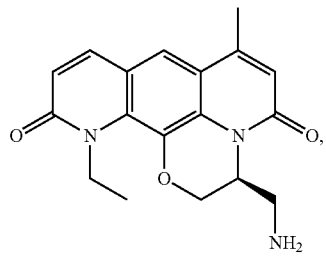
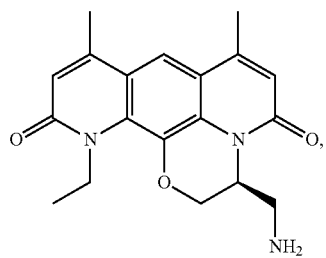
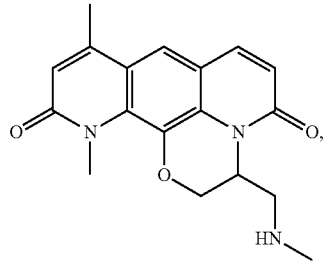
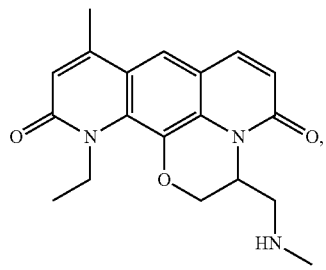
96
-continued
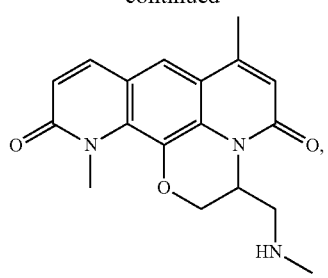
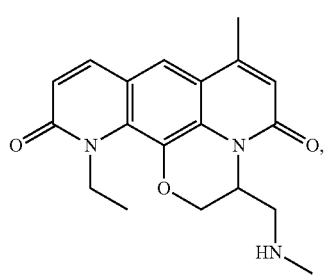
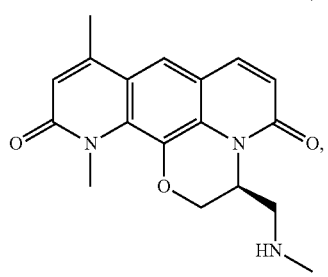
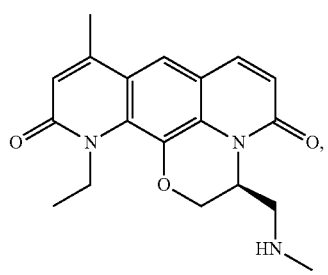
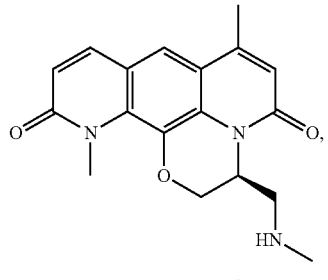
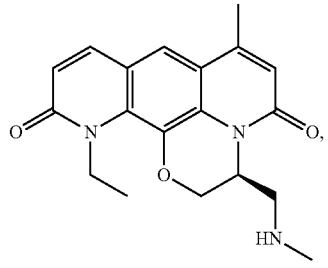

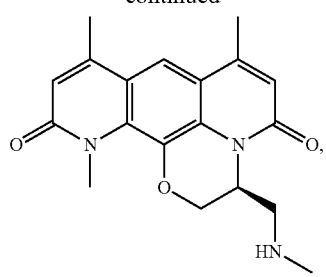
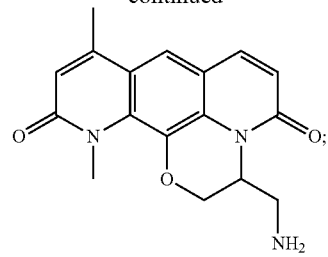
or a pharmaceutically acceptable salt thereof.
In some embodiments, the compound of formula (IX) is selected from the group consisting of:
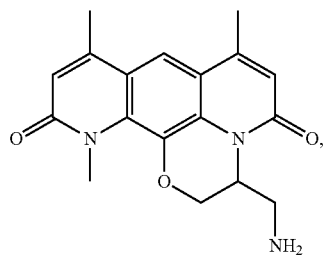
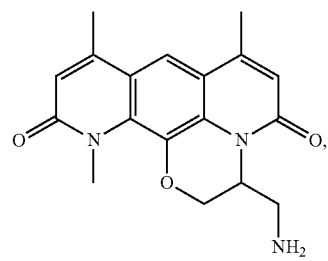
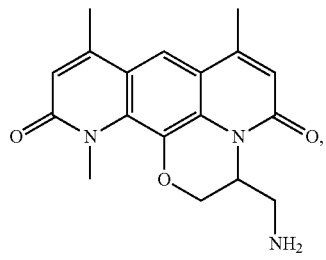
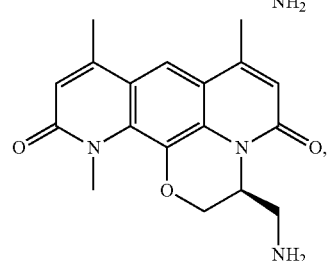
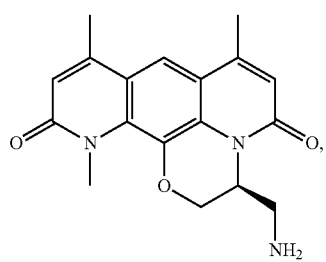
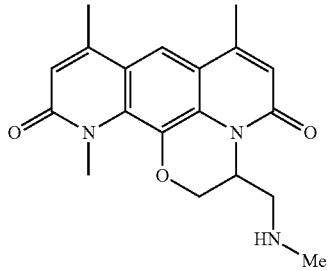
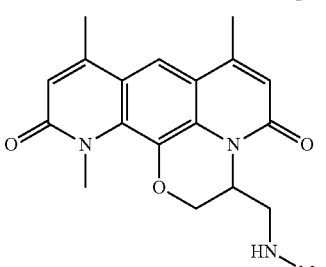
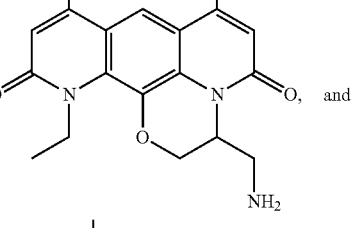
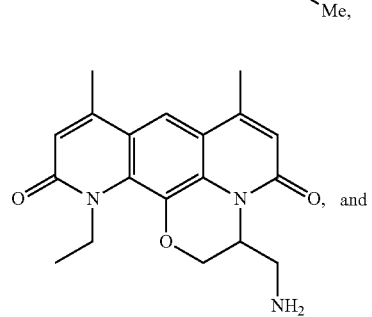
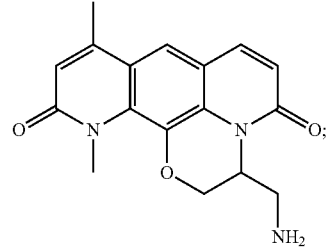

or a pharmaceutically acceptable salt thereof.

Exemplary Methods

In some embodiments, the compounds disclosed herein accumulate in Gram-negative bacteria.

In some embodiments, the compounds disclosed herein traverse a porin.

In some embodiments, provided herein is a method of antimicrobial treatment, comprising, administering to a subject in need thereof a therapeutically effective amount of a compound disclosed herein, or a pharmaceutically acceptable salt thereof, thereby killing or inhibiting the growth of at least a portion of a plurality of microorganisms in the subject.

In some embodiments, the compound is a compound of any one of formulas (I), (II), (III), (IV), (V), (VI), (VII), (VIII), or (IX).

In some embodiments, provided herein is a method of antimicrobial treatment, comprising:

providing a sample comprising a plurality of microorganisms;

contacting the sample with a compound disclosed herein;

thereby killing or inhibiting the growth of at least a portion of the plurality of microorganisms in the sample.

In some embodiments of the methods of antimicrobial treatment disclosed herein, at least a portion of the plurality of microorganisms is killed.

In some embodiments of the methods of antimicrobial treatment disclosed herein, the growth of at least a portion of the plurality of microorganisms is inhibited.

In some embodiments, the microorganism is a bacterium, a virus, a fungus, or a parasite. In some embodiments, the microorganism is drug resistant, such as antibiotic resistant. In some embodiments, the microorganism is multi-drug resistant.

In some embodiments, the microorganism is a bacterium. In some embodiments, the microorganism is a Gram-negative bacterium. In some embodiments, the microorganism is a Gram-positive bacterium. In some embodiments, for example, the microorganism is at least one bacterium selected from the group consisting of *Acinetobacter*, anthrax-causing bacteria, Bacilli, *Bordetella, Borrelia*, botulism, *Brucella, Burkholderia, Canpylobacter, Chlamydia*, cholera-causing bacteria, *Clostridium, Conococcus, Corynebacterium*, diptheria-causing bacteria, *Enterobacter, Enterococcus, Erwinia, Escherichia, Francisella, Haemophilus, Heliobacter, Klebsiella, Legionella, Leptospira*, leptospirosis-causing bacteria, *Listeria*, Lyme's disease-causing bacteria, meningococcus, *Mycobacterium, Mvcoplasma, Neisseria, Pasteurella, Pelobacter*, plague-causing bacteria, *Pneunonococcus, Proteus, Pseudiomonas, Rickettsia, Salmonella, Serratia, Shigella, Staphylococcus, Streptococcus*, tetanus-causing bacteria, *Treponema, Vibrio, Yersinia* and *Xanthomonas*. In some embodiments, the microorganism is at least one bacterium selected from the group consisting of *Acinetobacter baumannii, Escherichia coli, Enterobacter cloacae, Klebsiella pneumoniae, Pseudomonas aeruginosa*, and *Staphylococcus aureus*. In some embodiments, the microorganism is methicillin-resistant *Staphylococcus aureus* (MRSA). In some embodiments, the microorganism is *Pseudomonas aeruginosa*.

In some embodiments, for example, the microorganism is at least one virus selected from Adenoviridae, Papillomaviridae, Polyomaviridae, Herpesviridae, Poxviridae, Hepadnaviridae, Parvoviridae, Astroviridae, Caliciviridae, Picornaviridae, Coronoviridae, Flaviviridae, Retroviridae, Togaviridae, Arenaviridae, Bunyaviridae, Filoviridae, Orthonyxoviridae, Paramyxoviridae, Rhabdoiviridae, and Reoviridae. In certain embodiments, the virus may be arboviral encephalitis virus, adenovirus, herpes simplex type 1, herpes simplex type 2, Varicella-zoster virus, Epstein-barr virus, cytomegalovirus, herpesvirus type 8, papillomavirus, B3K virus, coronavirus, echovirus, JC virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus, orbivirus, coltivirus, vaccinia virus, and Banna virus.

In some embodiments, for example, the microorganism is at least one fungus selected from *Aspergillus (fumigatus, niger*, etc.), *Basidiobolus (ranarum*, etc.), *Blastomyces dermatitidis, Candida (albicans, krusei, glabrata, tropicalis*, etc.), *Coccidioides immitis, Cryptococcus (neoformans*, etc.), *eumycetoma, Epidermophylon (floccosum*, etc.), *Histoplasma capsulatum, Hortaea werneckii, Lacazia loboi, Microsproum (audouinii, nanum* etc.), *Mucorales (mucor, absidia, rhizophus), Paracoccidioides brasiliensis, Rhinosporidiun seeberi, Sporothrix schenkii*, and *Trichophyton* (schoeleinii, *mentagrophytes, rubrum, verrucosum*, etc.).

In some embodiments, for example, the microorganism is at least one parasite selected from *Acanthamoeba, Babesia microti, Balantidium coli, Eniamoeba hystolytica, Giardia lamblia, Cryptospordiun muris, Trypanosonatida gambiense, Trypanosonatida rhodesiense, Trypanosoma brucei, Trypanosoma cruzi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Pneumocystis carinii, Trichomonas vaginalis, Histomonoas meleagridis, Secementea, Trichuris trichiura, Ascaris lumbricoides, Enterobius vermicularis, Ancylostoma duodenale, Naegleria fowleri, Necator americanus, Nippostrongylus brasiliensis, Strongyloides stereoralis, Wuchereria bancrofti, Dracunculus medinensis*, blood flukes, liver flukes, intestinal flukes, lung flukes, *Schistosoma mansoni, Schistosoma haematobium, Schistosoma japonicum, Fasciola hepatica, Fasciola gigantica, Heterophves heterophyes*, and *Paragonimus westermani*.

For purposes of this disclosure, the chemical elements are identified in accordance with the Periodic Table of the Elements, CAS version, Handbook of Chemistry and Physics, 67th Ed., 1986-87, inside cover.

Definitions

For convenience, before further description of the present disclosure, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. For example, ($C_1$-$C_6$)alkyl. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths but with at least two carbon atoms. Preferred alkyl groups are lower alkyls. In preferred embodiments, a substituent designated herein as alkyl is a lower alkyl.

The term "aralkyl", as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "carboxy" as used herein, means a —$CO_2$H group.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "amido" as used herein, means —NHC(=O)—, wherein the amido group is bound to the parent molecular moiety through the nitrogen. Examples of amido include alkylamido such as $CH_3$C(=O)N(H)— and $CH_3CH_2$C(=O)N(H)—.

The term "aryl" as used herein includes 5-, 6- and 7-membered aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. Also, "DCM" stands for dichloromethane; "rt" stands for room temperature, and may mean about 20° C., about 21° C., about 22° C., about 23° C., about 24° C., about 25° C., or about 26° C.; "THF" stands for tetrahydrofuran; "BINAP" stands for 2,2'-bis(diphenylphosphino)-1,1'-binaphthyl; "dppf" stands for 1,1'-bis(diphenylphosphino)ferrocene; "dppb" stands for 1,4-bis(diphenylphosphino)butane; "dppp" stands for 1,3-bis(diphenylphosphino)propane; "dppe" stands for 1,2-bis(diphenylphosphino)ethane. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl", "heterocycloalkyl", or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroatom" as used herein means an atom of any element other than carbon or hydrogen. Preferred heteroatoms are nitrogen, oxygen, sulfur and phosphorous.

As used herein, the term "nitro" means —NO$_2$; the term "halogen" or "halo" designates —F, —Cl, —Br or —I; the term "sulfhydryl" means —SH; the term "hydroxyl" means —OH; the term "sulfonyl" means —SO$_2$—; and the term "cyano" as used herein, means a —CN group.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The terms "amine" and "amino" are art recognized and refer to both unsubstituted and substituted amines, e.g., a moiety that can be represented by the general formula:

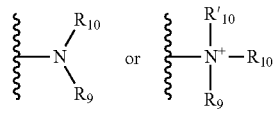

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$^8$. Thus, the term "alkylamine" as used herein means an amine group, as defined above, having a substituted or unsubstituted alkyl attached thereto, i.e., at least one of R$_9$ and R$_{10}$ is an alkyl group.

The definition of each expression, e.g., alkyl, m, n, and the like, when it occurs more than once in any structure, is intended to be independent of its definition elsewhere in the same structure.

The terms triflyl (-Tf), tosyl (-Ts), mesyl (-Ms), and nonaflyl are art-recognized and refer to trifluoromethanesulfonyl, p-toluenesulfonyl, methanesulfonyl, and nonafluorobutanesulfonyl groups, respectively. The terms triflate (-OTf), tosylate (-OTs), mesylate (-OMs), and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The phrase "protecting group" as used herein means temporary modifications of a potentially reactive functional group which protect it from undesired chemical transformations. Examples of such protecting groups include silyl ethers of alcohols, and acetals and ketals of aldehydes and ketones, respectively. In embodiments of the disclosure, a carboxylate protecting group masks a carboxylic acid as an ester. In certain other embodiments, an amide is protected by an amide protecting group, masking the —NH$_2$ of the amide as, for example, —NH(alkyl), or —N(alkyl)$_2$. The field of protecting group chemistry has been reviewed (Greene, T. W.; Wuts, P. G. M. *Protective Groups in Organic Synthesis*, 2$^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this disclosure, the heteroatoms, such as nitrogen, may have hydrogen substituents and/or any permissible substituents of organic compounds described herein which satisfy the valencies of the heteroatoms.

As used herein, the term "rotatable bonds" as used herein is a count of single bonds, not in a ring, bound to a nonterminal heavy atom. Excluded from the count are C—N amide bonds because of their high rotational energy barrier. Rotatable bonds are abbreviated as "RB" herein.

The term "ClogD$_{7.4}$" as used herein means the predicted octanol/water distribution coefficient at pH 7.4.

The term "globularity" as used herein means the inverse condition number of the covariance matrix of atomic coordinates (a value of 1 indicates a perfect sphere while a value of 0 indicates a two- or one-dimensional object). Globularity is abbreviated as "Glob" herein.

The phrase "plane of best fit" (PBF) as used herein means the average distance in angstroms of each heavy atom in the molecule to the plane that best fits atomic coordinates.

The phrase "principal moment of inertia" (PMI1) as used herein means the first diagonal element of diagonalized moment of inertia tensor. See Sauer, W. H. & Schwarz, M. K. Molecular shape diversity of combinatorial libraries: a prerequisite for broad bioactivity. J J. *Chem. Inf Comput. Sci.* 43, 987-1003, (2003).

The phrase "PMI1/MW" as used herein represents the ratio of PMI 1 and molecular weight. This represents the normalized principal moment of inertia.

The term "vsurf_A" as used herein means a vector pointing from the center of the hydrophobic domain to the center of the hydrophilic domain. The vector length is proportional to the strength of the amphiphilic moment. See Thanassi, D. G., Suh, G. S. & Nikaido, H. Role of outer membrane barrier in efflux-mediated tetracycline resistance of *Escherichia coli. J. Bacteriol.* 177, 998-1007, (1995).

EXEMPLIFICATION

The disclosure may be understood with reference to the following examples, which are presented for illustrative purposes only and which are non-limiting. The substrates utilized in these examples were either commercially available, or were prepared from commercially available reagents.

Example 1—Accumulation Assay

Figure 2:
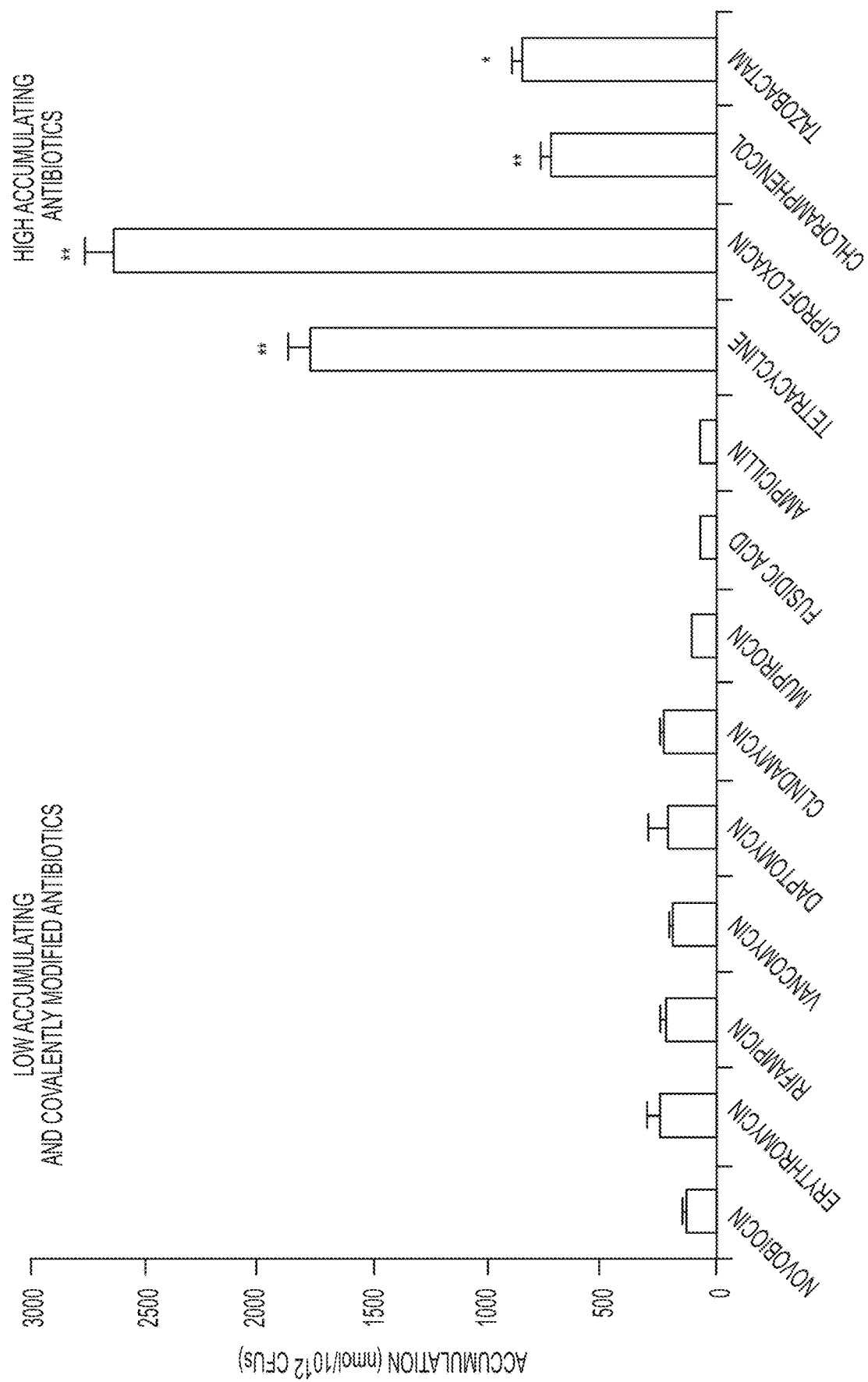
FIG. 2 depicts accumulation in Gram-negative bacteria of exemplary compounds with high activity or low activity against Gram-negative bacteria.

The method for assessment of accumulation was adapted from Bazile, S., Moreau, N., Bouzard, D. & Essiz, M. Relationships among antibacterial activity, inhibition of DNA gyrase, and intracellular accumulation of 11-fluoroquinolones. *Antimicrob. Agents Chemother.* 36, 2622-2627, (1992); Davis, T. D., Gerry, C. J. & Tan, D. S. General platform for systematic quantitative evaluation of small-molecule permeability in bacteria. *ACS Chem. Biol.* 9, 2535-2544, (2014); and Cai, H., Rose, K., Liang, L. H., Dunham, S. & Stover, C. Development of a liquid chromatography/mass spectrometry-based drug accumulation assay in *Pseudomonas aeruginosa*. *Anal. Biochem.* 385, 321-325, (2009); with LC-MS/MS used to quantify the accumulation of each compound. *E. coli* MG1655 was utilized for these experiments as this strain has been only minimally altered from its K-12 progenitor. To ensure the assay was reporting on compound accumulation, as opposed to non-specific affinity for the outer membrane, several control experiments were conducted. The assay method was evaluated with antibiotics that have known high or low levels of accumulation, based on published accumulation data and antibacterial activity against *E. coli*. Known high accumulating antibacterials (tetracycline, ciprofloxacin, chloramphenicol) and tazobactam (a β-lactamase inhibitor active in Gram-negative bacteria), and low accumulating antibacterials (novobiocin, erythromycin, rifampicin, vancomycin, daptomycin, clindamycin, mupirocin, and fusidic acid) were assessed. Ampicillin was also used as a "low-accumulation" control as it is rapidly covalently appended to the reactive serine residue in the active site of penicillin-binding proteins, preventing measurement by LC-MS/MS. To account for the possibility of non-specific binding to the outer membrane, Gram-negative active antibiotics with various charged states at physiological pH were chosen: tetracycline (positively charged), tazobactam (negatively charged), ciprofloxacin (zwitterionic), and chloramphenicol (neutral). The results show a significantly higher level of accumulation in *E. coli* for the Gram-negative-active compounds as compared to compounds with low Gram-negative antibacterial activity and ampicillin, consistent with measuring accumulation as opposed to non-specific binding (FIG. 2). To further ensure that variations in observed accumulation levels were not due to differences in non-specific affinity of the controls for the membrane, penetrance was perturbed by co-treating *E. coli* with the membrane permeabilizing agent colistin. Colistin is known to potentiate the activity of low-accumulating antibiotics by aiding the diffusion of lipophilic compounds across the membrane. For an assay measuring accumulation as opposed to non-specific binding, low-accumulating antibiotics in *E. coli* would show an increased level of accumulation in this experiment. Indeed, in the assay an increase in accumulation for low-accumulating antibiotics (novobiocin, erythromycin, rifampicin, and fusidic acid) was observed upon co-treatment with colistin (data not shown).

Figure 3:
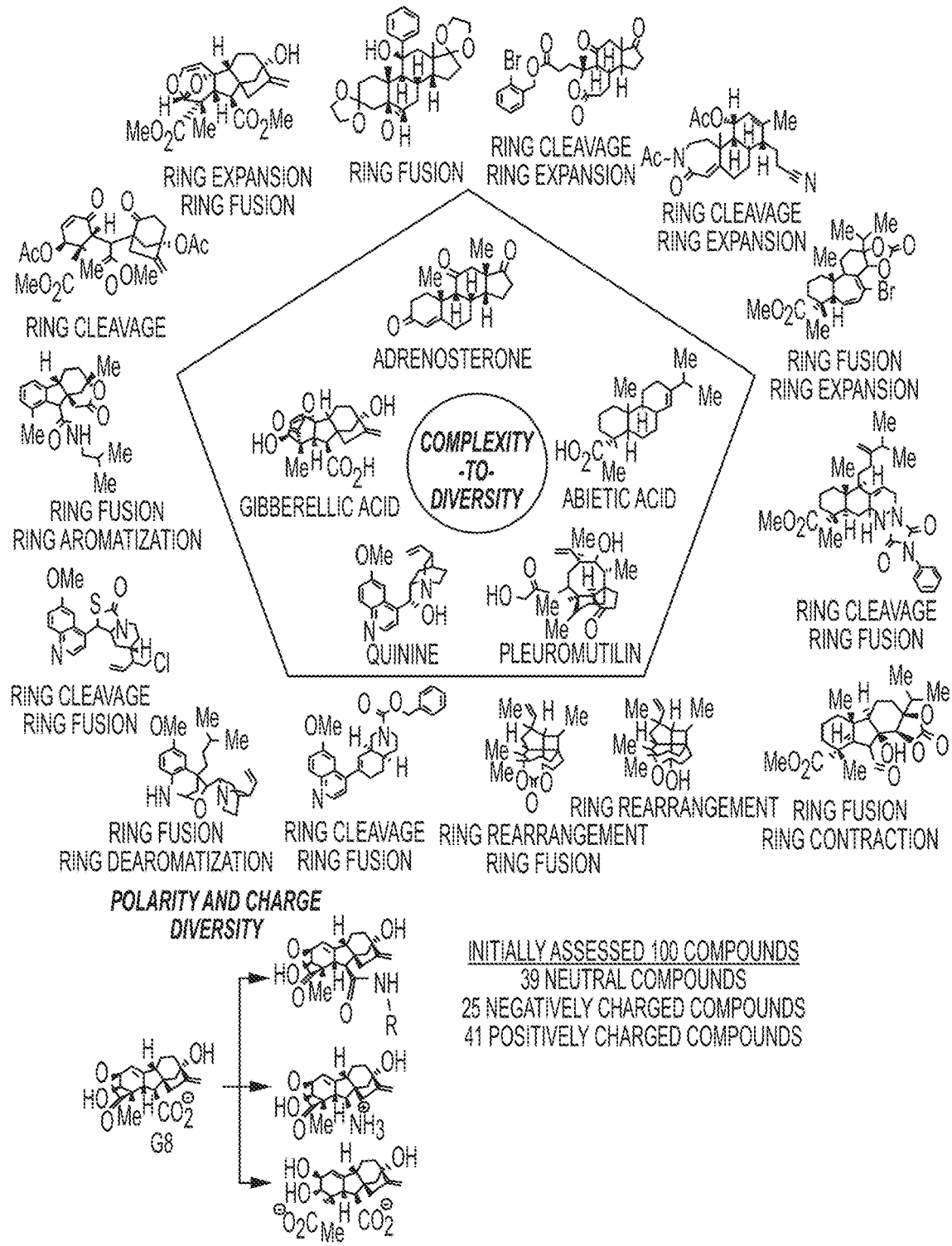
FIG. 3 depicts a schematic representation of complexity-to-diversity synthesis.
Figure 4:
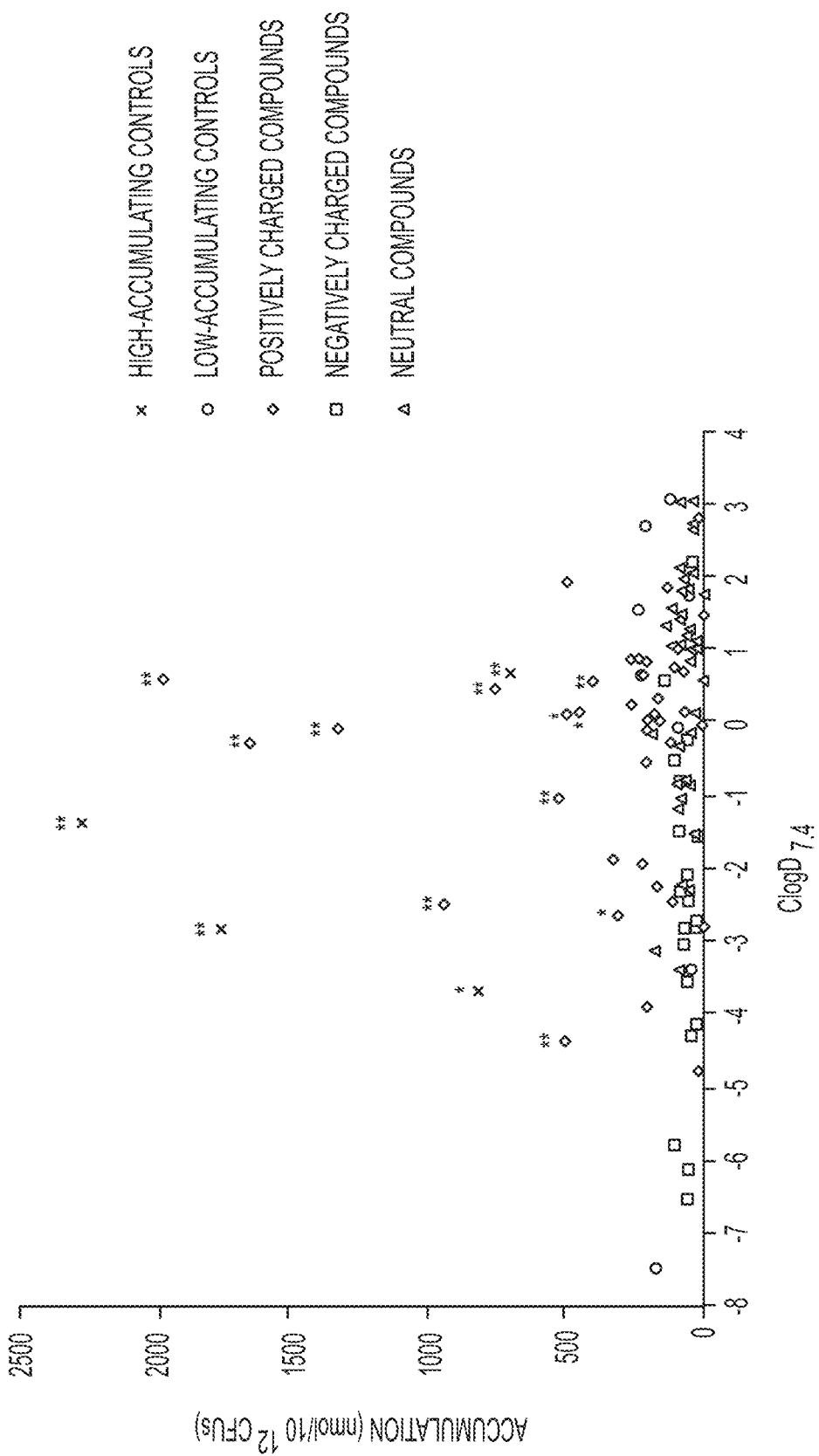
FIG. 4 depicts a scatter plot of accumulation in Gram-negative bacteria of a library of compounds as a function of ionic state.

Towards understanding the physicochemical properties that influence small molecule accumulation in *E. coli*, a collection of diverse compounds was required. Given that the majority of antibacterial drugs are natural products or their derivatives, critical to this effort would be access to a collection of compounds whose members possess natural-product-like properties, but also are synthetically accessible so that various physicochemical traits are tunable, enabling SAR studies on accumulators. Thus, these compounds were produced using the "complexity-to-diversity" (CtD) strategy (FIG. 3), whereby diverse compounds are constructed from readily available natural products. To begin the analysis, a set of 100 compounds, including positively charged, negatively charged, and neutral compounds (including two zwitterions) were synthesized and tested. As retrospective studies suggest that compound accumulation is related to $ClogD_{7.4}$, after assessing accumulation in *E. coli* for all 100 compounds, the accumulation data were plotted vs $ClogD_{7.4}$. This data is shown in FIG. 4, with ionic state of the compounds indicated by the shape of the data points (diamonds=positive, triangles=neutral, squares=negative). These results strikingly differ from the conclusions gleaned from retrospective studies. Within this set of 100 compounds, charge is the primary factor dictating accumulation in *E. coli*. The positively-charged compounds are the most likely to accumulate, with 12 of 41 positively-charged compounds showing a significant level of accumulation compared to the low accumulating controls. In contrast, 0 of 39 neutral compounds and 0 of 20 negatively-charged compounds show a level of accumulation higher than the negative controls. Notably, even carboxylic acids with strongly negative $ClogD_{7.4}$ values (<-5) do not accumulate, whereas certain amines with relatively high $ClogD_{7.4}$ values (>0) do accumulate.

Figure 5:
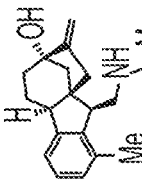
FIG. 5 depicts a series of compounds with modified primary amines and accumulation data in Gram-negative bacteria.
Figure 6:
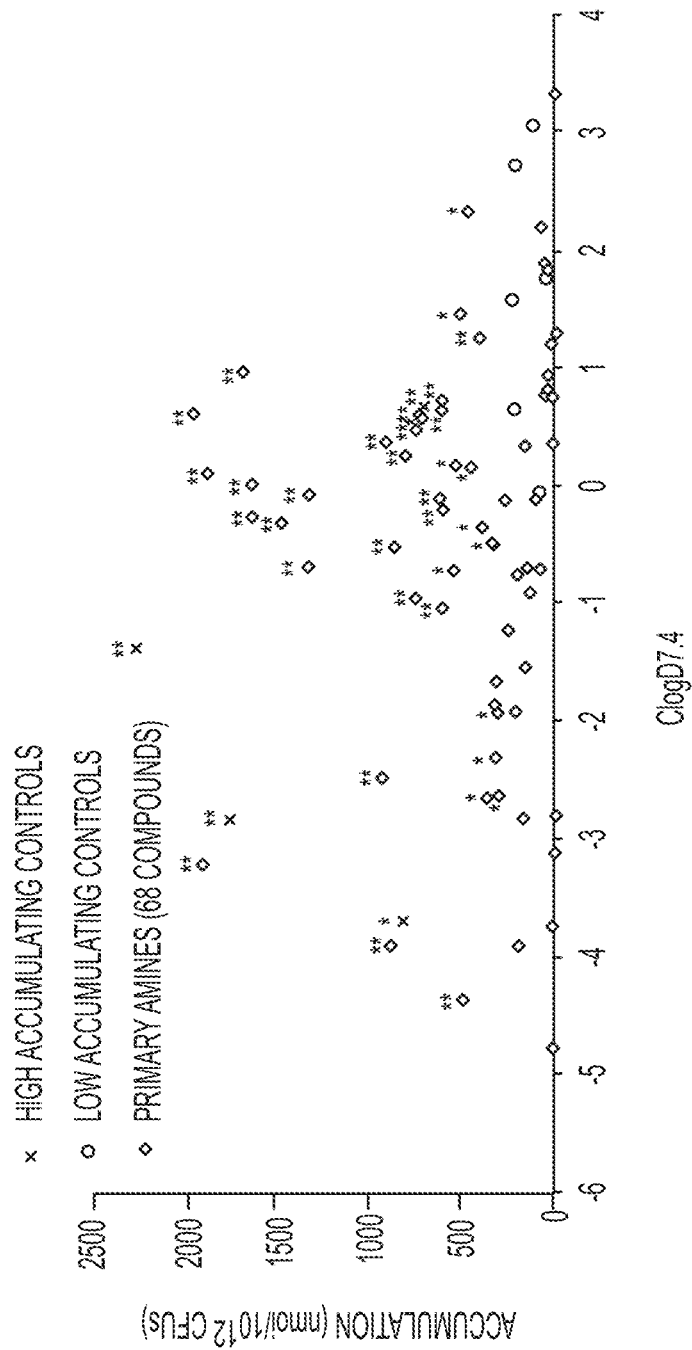
FIG. 6 depicts a scatter plot of accumulation in Gram-negative bacteria of exemplary primary amine compounds as a function of $ClogD_{7.4}$.
Figure 7:
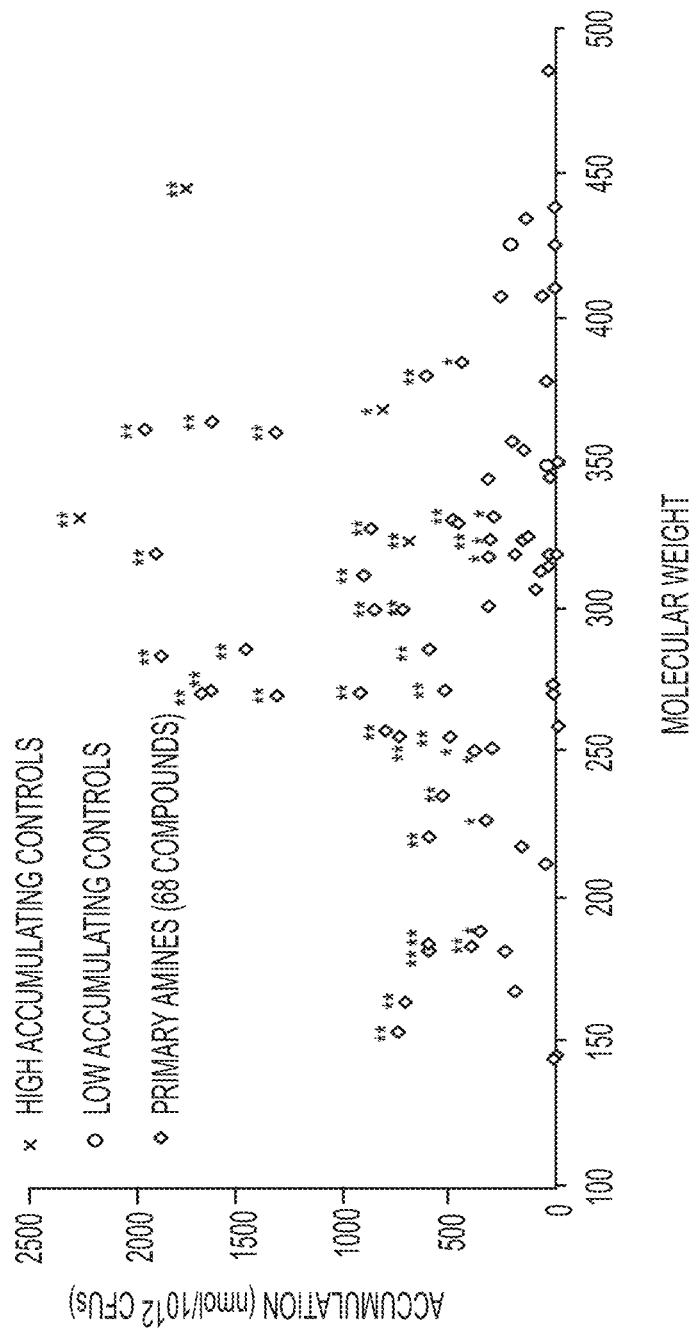
FIG. 7 depicts a scatter plot of accumulation in Gram-negative bacteria of exemplary primary amine compounds as a function of molecular weight.

All 12 accumulating compounds contain amines, and the majority of these compounds (8 out of 12) are primary amines. To further examine the importance of the primary amine, a SAR analysis was performed for multiple different classes of accumulating compounds. Replacement of the amine with a carboxylic acid, an amide, an ester, a nitrile, an azide, or an alcohol on multiple different scaffolds dramatically reduces accumulation. Even conversion of the primary amine to a more substituted amine has a deleterious effect on accumulation. Shown in FIG. 5 are three primary amines (1-3) alongside their methylated (4-6), di-methylated (7-9), tri-methylated (10-12), and acetylated derivatives (13-15). In all cases, the primary amine shows the highest level of accumulation, with only one of the derivatives (6) showing significant accumulation. An additional 54 primary amine-containing compounds were then obtained and their accumulation in *E. coli* was assessed; these compounds are both CtD compounds and commercially available primary amines that more closely mimic the types of compounds found in commercial screening libraries. A graph of accumulation versus $ClogD_{7.4}$ for all 68 primary amines (8 accumulators from initial test set, 6 non-accumulators from initial test set, and 54 additional amines) is provided in FIG. 6. Again, for this set of amines accumulation does not increase with lower $ClogD_{7.4}$, and when MW is plotted versus accumulation for the 68 primary amines, there is also no correlation (FIG. 7). SAR analysis on several of these compounds also showed the importance of the amine to accumulation (data not shown).

Figure 8A:
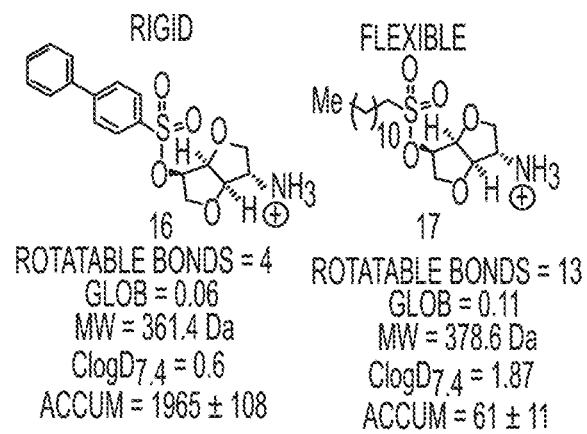
FIG. 8A depicts exemplary rigid and flexible molecules based on the number of rotatable bonds for the primary amines.
Figure 8B:
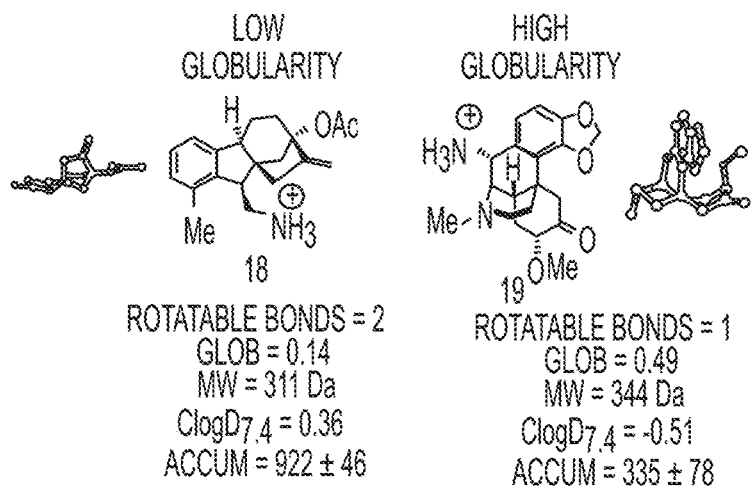
FIG. 8B depicts exemplary globularity of molecules based on the 3-dimensional structure of the primary amines.

While the presence of a primary amine is clearly important for accumulation in *E. coli*, it is not sufficient: although 36 of the primary amines within the test set do accumulate, 32 of them do not. Therefore, a chemoinformatic approach was implemented to understand which factors contribute to amine accumulation. For this expanded set of 68 primary amines, 297 molecular descriptors were calculated for conformer ensembles of each compound (e.g., MW, $ClogD_{7.4}$, rotatable bonds, globularity, PBF, and PMI1/MW). For example, this set of primary amines included dihydrofolate reductase inhibitors (e.g., iclaprim), fluoroquinolone (e.g., ciprofloxacin and lomefloxacin), sulfa (e.g., sulfadiazine and sulfameter), tetracycline (e.g., doxycycline and tigecycline), macrolide (e.g., clarithromycin and erythromycin), oxazolidinone (e.g., ranbezolid), glycopeptide (e.g., dalbavancin and vancomycin), lincosamide (e.g., lincomycin), lipopeptide (e.g., daptomycin), ansamycin (e.g., rifampicin), and steptogramin (e.g., dalfopristin) antibiotics. The molecular descriptors were used to train a random forest classification model that predicts amine accumulation (data not shown). The random forest model offers many advantages for this application including resistance to over-fitting and the ability to measure descriptor importance. Through this analysis it was revealed that the flexibility and shape of a compound are important factors that govern accumulation. Flexibility was best captured by measuring the number of rotatable bonds (RB), whereas shape was best described by the term globularity (ratio of smallest eigenvalue and largest eigenvalue following principal component analysis of atomic coordinates). This globularity analysis (Glob), is routinely used to provide information on the three-dimensionality of compounds, where a completely flat compound (e.g. benzene) has a Glob of 0 and a spherical compound (e.g. adamantane) has a Glob of 1. Molecular Operating Environment (MOE), 2015.10 (1010 Sherbooke St. West, Suite #910, Montreal, QC, 381 Canada, H3 A 2R7, 2016). Case studies demonstrate the importance of the flexibility and globularity parameters for accumulation of the primary amines: as shown in FIG. 8A, amine 16 with four RBs accumulates at a high level (1965 nmol/$10^{12}$ CFUs); however, amine 17, a compound of similar molecular weight and Glob but with 13 RBs, shows virtually no accumulation. Analogous results are observed in FIG. 8B when comparing a compound with low globularity (18, Glob=0.14, accumulation=922 nmol/$10^{12}$ CFUs) to a compound with similar functional groups, MW, and RBs but with high globularity (19, Glob=0.49, accumulation=335 nmol/$10^{12}$ CFUs); compound globularity is most easily observed in their three-dimensional models, FIG. 8B.

Figure 9:
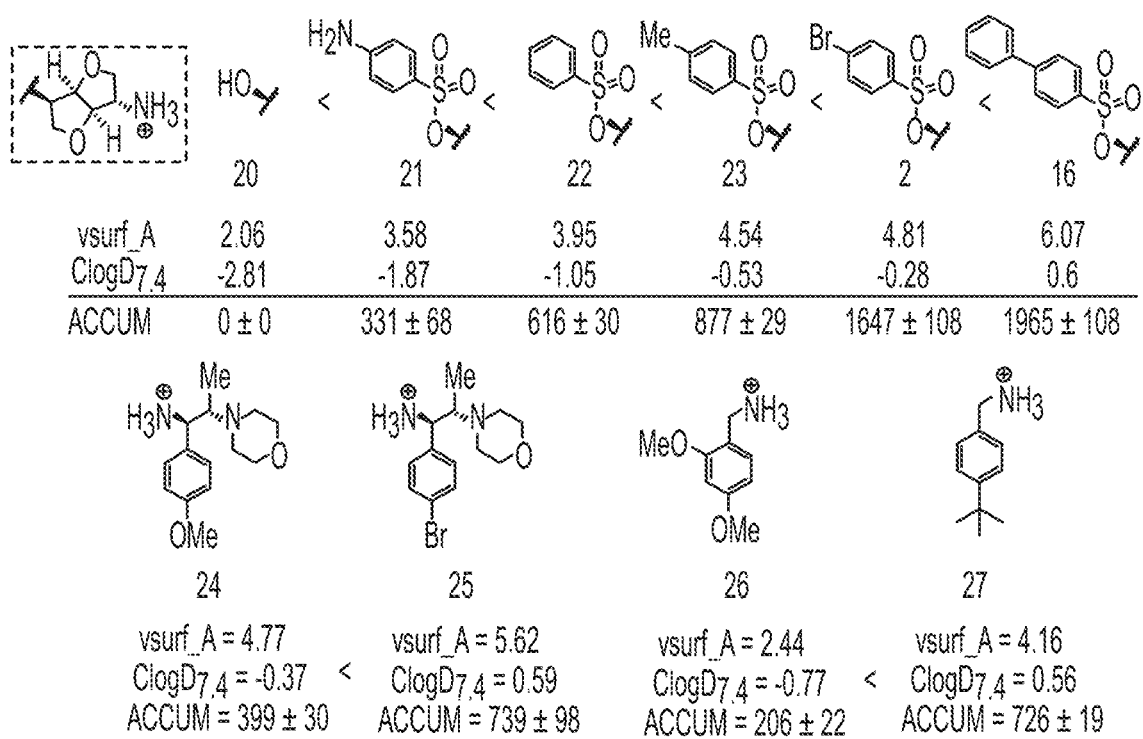
FIG. 9 depicts an exemplary derivative set demonstrating the correlation between accumulation and amphiphilic moment within a structural class of compounds.
Figure 10A:
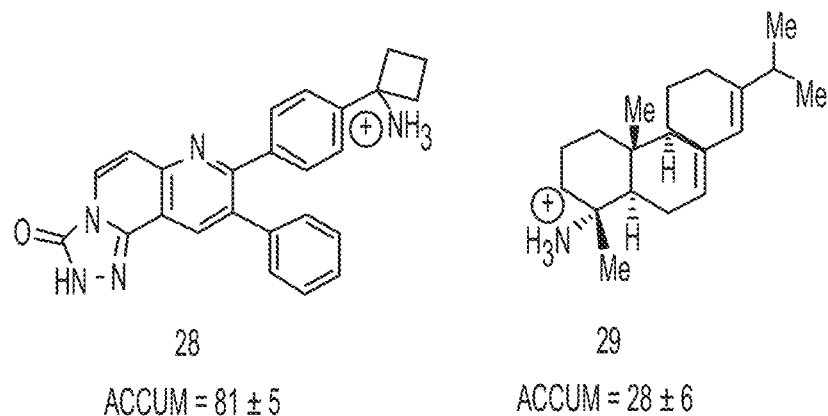
FIG. 10A depicts exemplary molecules with primary amines bonded to a tertiary center.
Figure 10B:
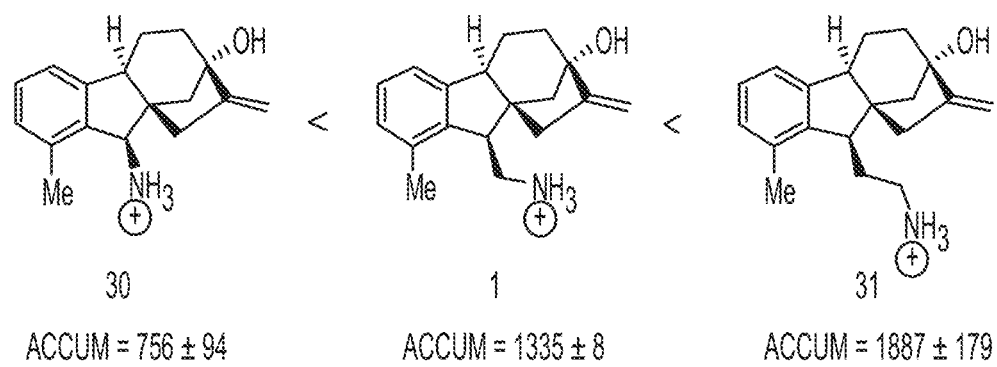
FIG. 10B depicts the correlation between accumulation and distance from a sterically-congested ring system.

While in general primary amines with five or fewer RBs and a globularity of 0.25 or less have a markedly higher likelihood of accumulation, two additional factors related to the placement of the primary amine are important. First, the random forest model identified increased amphiphilic moment (vsurf_A), which measures the distance between hydrophobic and hydrophilic portions of a compound, as favoring accumulation. Strikingly, while mono-amine isomannide (20) does not accumulate, derivatives with increased vsurf_A do accumulate (21-23, 2 and 16) (FIG. 9), and similar trends are observed for other compound classes (24-27) (FIG. 9). Accordingly, some degree of hydrophobicity appears necessary for accumulation, although in practice most organic compounds possess this feature. Secondly, compounds with sterically encumbered primary amines are not high accumulators, for example 28 and 29 (FIG. 10A), which both have low flexibility and globularity but contain a primary amine on a tetra-substituted carbon, do not show significant accumulation. This result is in accord with the superior accumulation of primary amines versus substituted amines (FIG. 5), and is also consistent with the increased accumulation of compounds where the primary amine is systematically extended from a sterically congested ring system (30<1<31), as shown in FIG. 10B.

Figure 11:
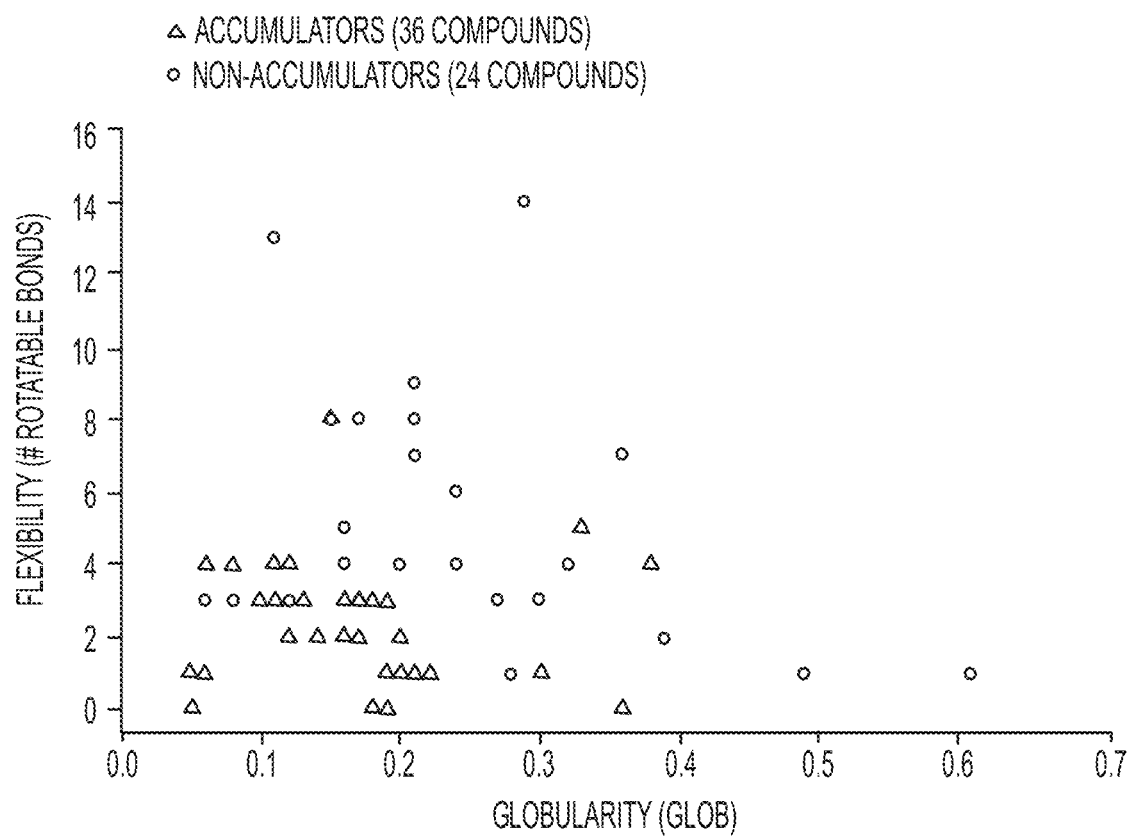
FIG. 11 depicts the correlation between accumulation, flexibility, and globularity data for exemplary compounds.
Figure 12A:
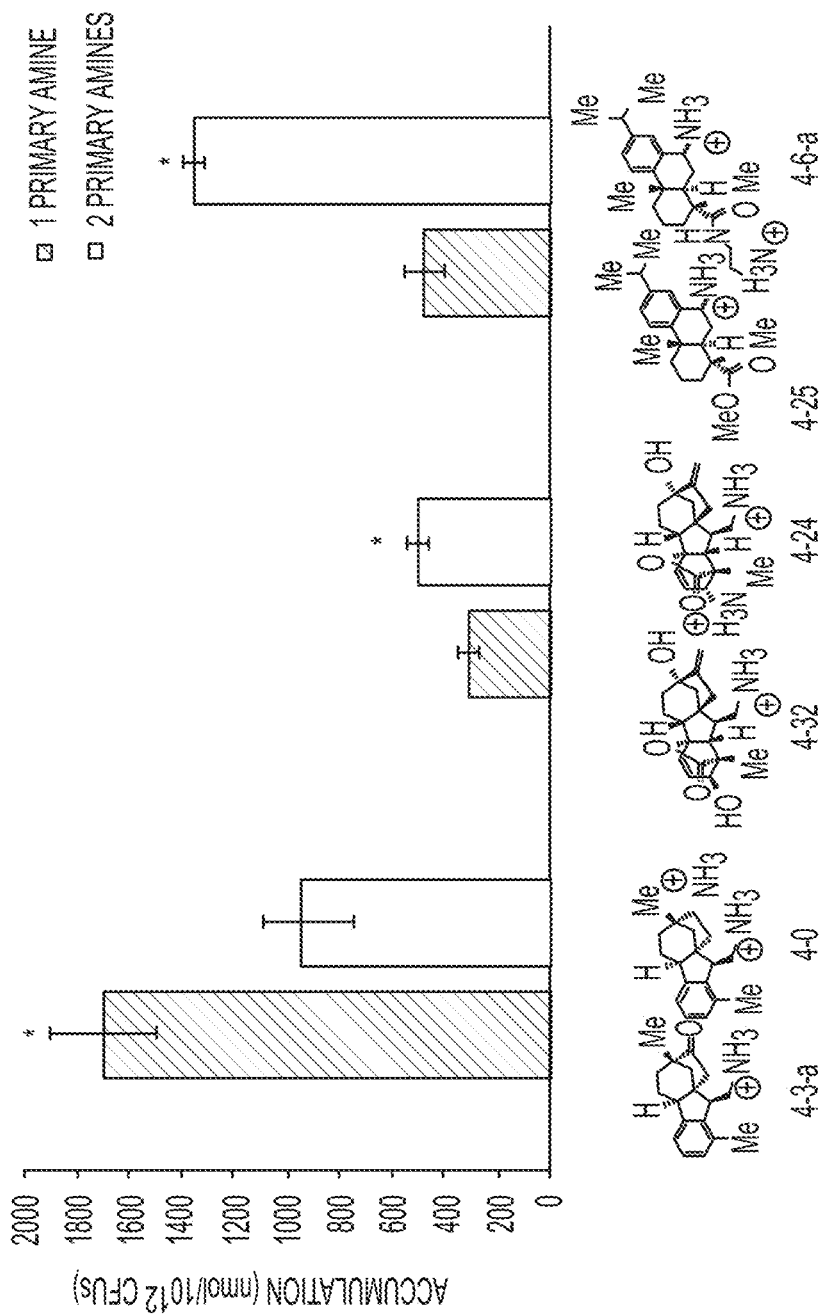
FIG. 12A depicts the correlation between accumulation and the number of primary amines for exemplary compounds.
Figure 12B:
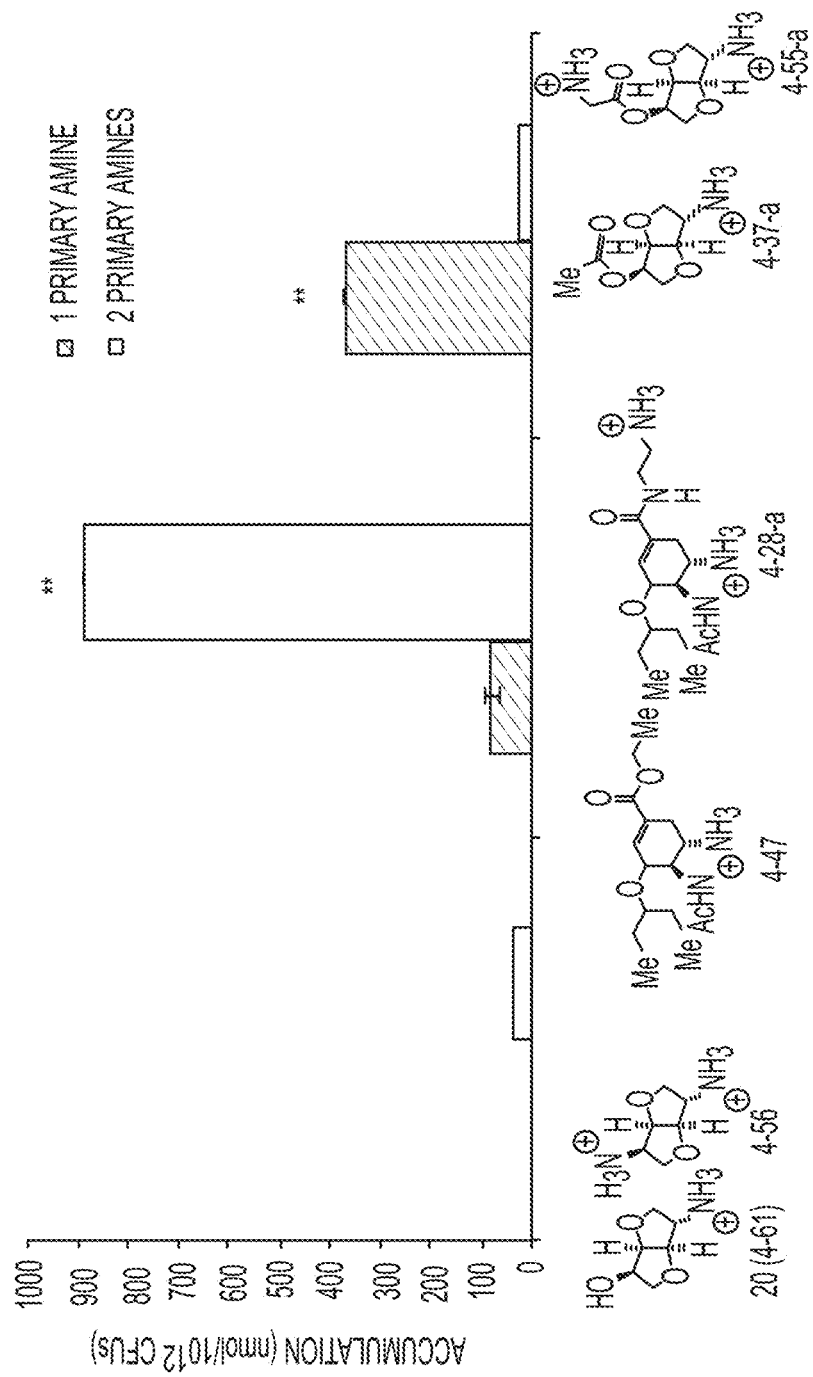
FIG. 12B depicts the correlation between accumulation and the number of primary amines for exemplary compounds.

Based on these analyses the following guiding principles for compound accumulation in *E. coli* were developed: compounds are most likely to accumulate if they contain a non-sterically encumbered primary amine, some non-polar functionality, are rigid, and have low globularity. As shown in FIG. 11, the vast majority of compounds that meet these criteria in the test set accumulate in *E. coli*. It should be noted that side-by-side comparisons of compounds containing two primary amines to analogues with one amine, (6 paired sets of compounds), largely follow the same rules for accumulation with no clear impact of the second primary amine (FIGS. 12A and 12B).

Figure 13:
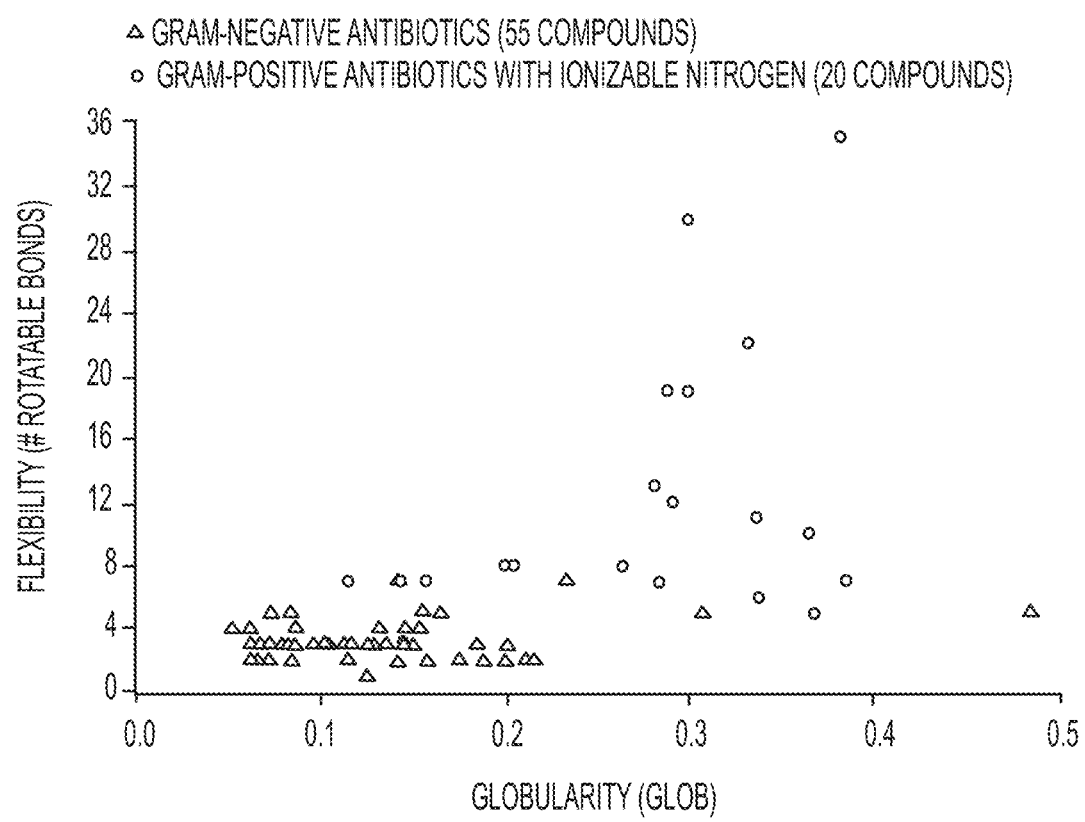
FIG. 13 depicts for antibiotics active against Gram-negative or Gram-positive bacteria a scatter plot of rotatable bond count of exemplary primary amine compounds compared to the globularity.
Figure 14A:
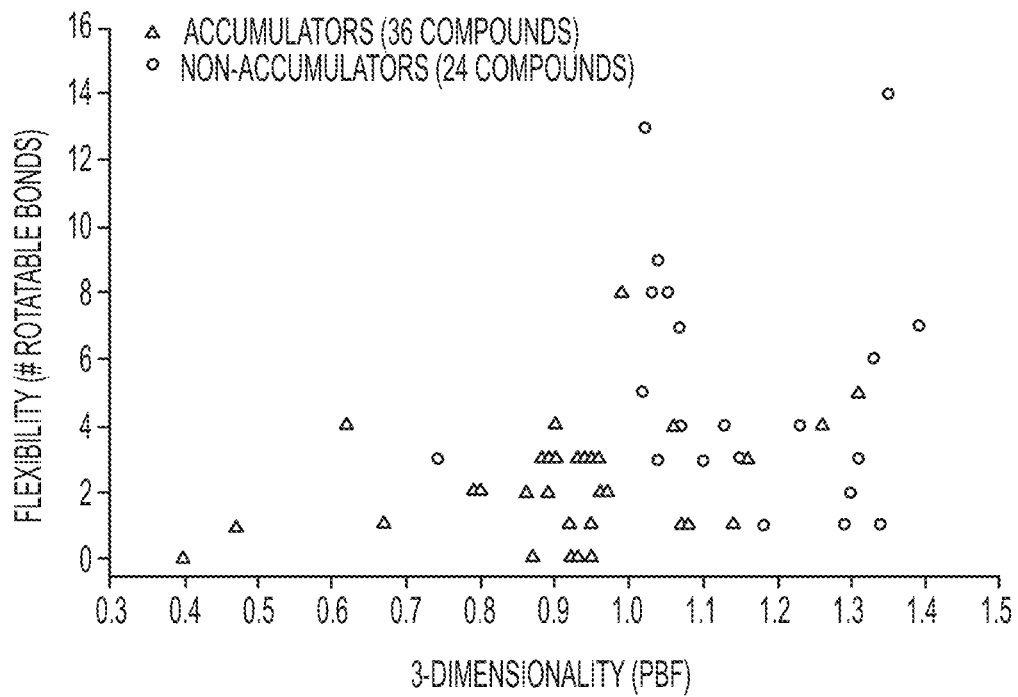
FIG. 14A depicts for antibiotics that accumulate in Gram-negative bacteria or do not a scatter plot of rotatable bond count of exemplary primary amine compounds compared to the plane-of-best-fit.
Figure 14B:
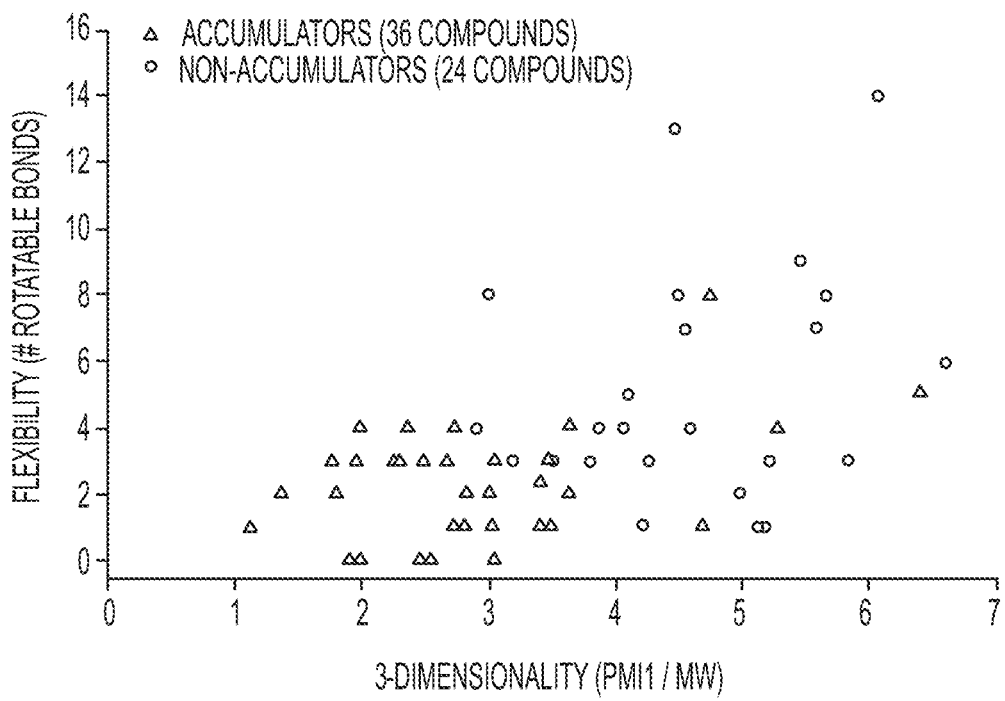
FIG. 14B depicts for antibiotics that accumulate in Gram-negative bacteria or do not a scatter plot of rotatable bond count of exemplary primary amine compounds compared to the normalized principle moment of inertia.
Figure 15A:
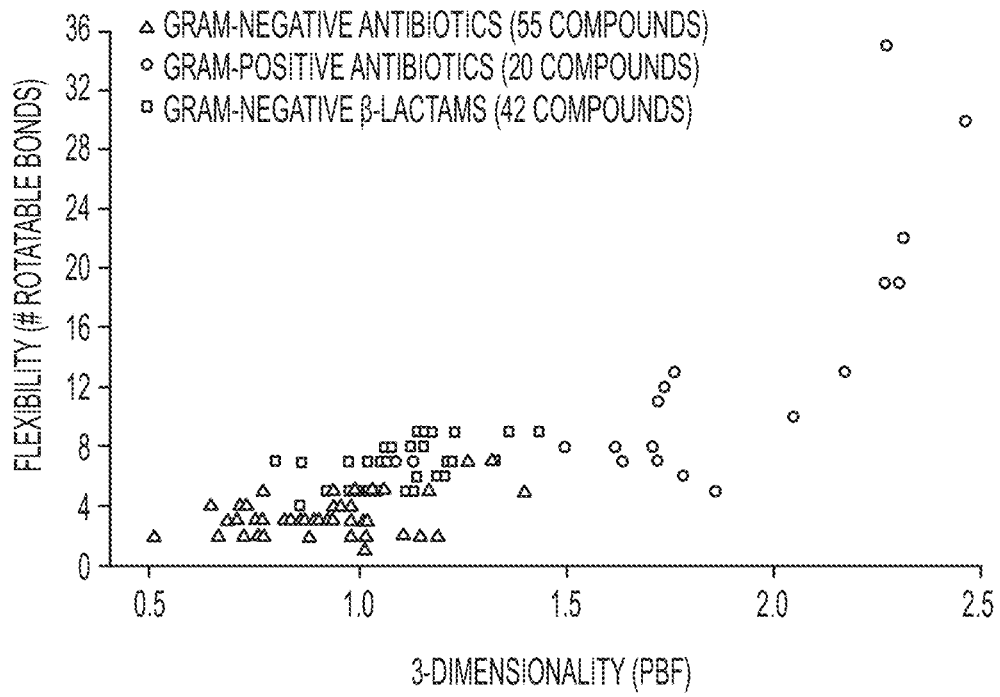
FIG. 15A depicts a scatter plot of rotatable bond count of exemplary antibiotics compared to the plane-of-best-fit.
Figure 15B:
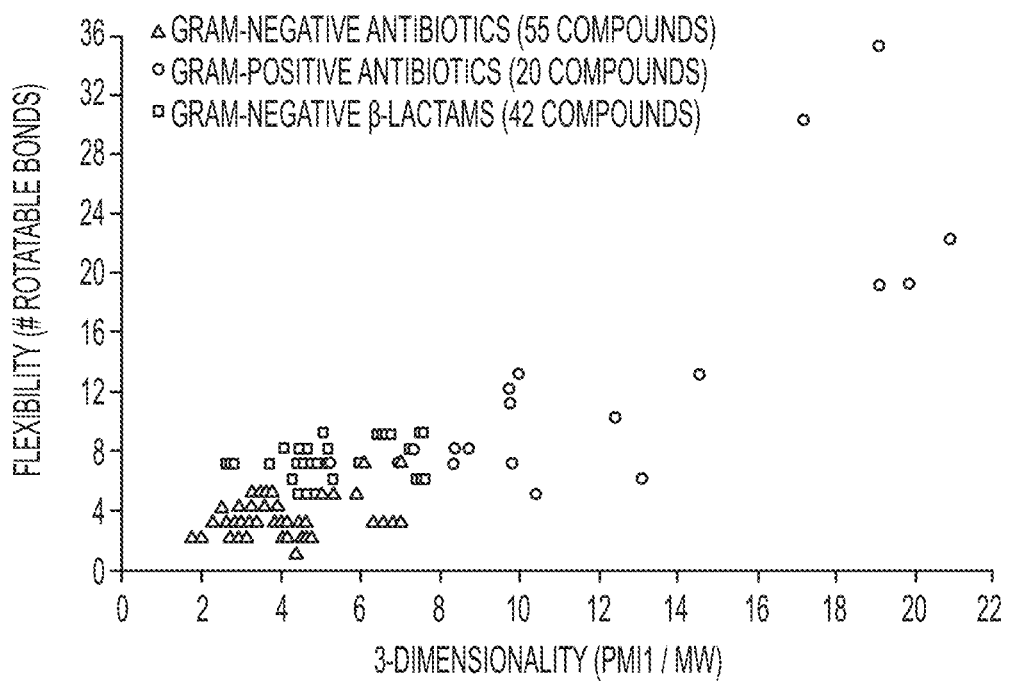
FIG. 15B depicts a scatter plot of rotatable bond count of exemplary antibiotics compared to the normalized principle moment of inertia.

To further test the validity of these guidelines, the set of antibacterials assessed by O'Shea and Moser was evaluated for charge, flexibility, and globularity. For the charge analysis, antibacterial drugs containing an ionizable nitrogen were accepted. For Gram-negative antibacterials, only those predicted to enter through porins were included, and due to the sheer number of β-lactams they have been left off the graph in FIG. 13. As is shown in FIG. 13, for these drugs with ionizable nitrogens, compounds active against Gram-negative bacteria cleanly separate from those with Gram-positive-only activity based on these two physicochemical parameters. As is also apparent from FIG. 13, no Gram-positive-only antibacterial with an ionizable nitrogen has the correct rigidity and globularity for accumulation in *E. coli*. Although globularity was found to best predict accumulators and non-accumulators in combination with flexibility, other measures of three-dimensionality also exhibit the same trend (FIGS. 14A-15B).

The accumulation assay was performed in triplicate in batches of ten samples, with each batch containing either tetracycline or ciprofloxacin as a positive control. For each replicate, 2.5 mL of an overnight culture of *E. coli* was diluted into 250 mL of fresh Luria Bertani (LB) broth (Lennox) and grown at 37° C. with shaking to an $OD_{600}$=0.55. The bacteria were pelleted at 3,220 rcf for 10 minutes at 4° C. and the supernatant was discarded. The pellets were re-suspended in 40 mL of phosphate buffered saline (PBS) and pelleted as before, and the supernatant was discarded. The pellets were re-suspended in 8.8 mL of fresh PBS and aliquoted into ten 1.5 mL eppendorf tubes (875 µL each). The number of colony forming units (CFUs) was determined via a calibration curve. The samples were equilibrated at 37° C. with shaking for 5 minutes, compound was added ([final]=50 µM), and then samples were incubated at 37° C. with shaking for 10 minutes. A 10-minute time point was chosen because it is longer than the predicted amount of time required to reach a steady-state concentration, but short enough to minimize metabolic and growth changes (no changes in $OD_{600}$ observed; CFUs were reduced by a factor of five after ciprofloxacin treatment for 10 minutes, but no other antibiotics had an effect). After incubation, 800 µL of the cultures were carefully layered on 700 µL of silicone oil (9:1 AR20/Sigma High Temperature, cooled to −78° C.). Bacteria were pelleted through the oil by centrifuging at 13,000 rcf for 2 minutes at room temperature (supernatant remains above the oil); the supernatant and oil were then removed by pipetting. To lyse the samples, each pellet was dissolved in 200 µL of water, and then they were subjected to three freeze-thaw cycle of three minutes in liquid nitrogen followed by three minutes in a water bath at 65° C. The lysates were pelleted at 13,000 rcf for 2 minutes at room temperature and the supernatant was collected (180 µL). The debris was re-suspended in 100 µL of methanol and pelleted as before. The supernatants were removed and combined with the previous supernatants collected. Finally, remaining debris was removed by centrifuging at 20,000 rcf for 10 minutes at room temperature. Supernatants were analyzed by LC-MS/MS.

Samples were analyzed with the 5500 QTRAP LC/MS/MS system (AB Sciex, Foster City, CA) with a 1200 series HPLC system (Agilent Technologies, Santa Clara, CA) including a degasser, an autosampler, and a binary pump. The LC separation was performed on an Agilent SB-Aq column (4.6×50 mm, 5 µm) (Agilent Technologies, Santa Clara, CA) with mobile phase A (0.1% formic acid in water) and mobile phase B (0.1% formic acid in acetonitrile). The flow rate was 0.3 mL/min. The linear gradient was as follows: 0-3 min, 100% A; 10-15 min, 2% A; 15.5-21 min, 100% A. The autosampler was set at 5° C. The injection volume was 15 µL. Mass spectra were acquired with both positive electrospray ionization (ESI) at the ion spray voltage of 5500 V and negative ESI at the ion spray voltage of −4500 V. The source temperature was 450° C. The curtain gas, ion source gas 1, and ion source gas 2 were 33, 50, and 65, respectively. Multiple reaction monitoring (MRM) was used to quantify metabolites.

Power analysis was performed using G*Power 3.1 to determine appropriate sample size. Based on data collected from control compounds (FIG. 2), three replicates would be necessary in order to detect accumulation above 500 nmol/$10^{12}$ CFUs at 0.96 percent power. Error bars represent the standard error of the mean of three biological replicates. All compounds evaluated in biological assays were ≥95% pure.

Assays measuring permeabilization by colistin were performed as above, with the addition of 6.0 µM colistin sulfate immediately before the compound of interest was added.

Example 2—Calculation of Physiochemical Properties

Figure 16:
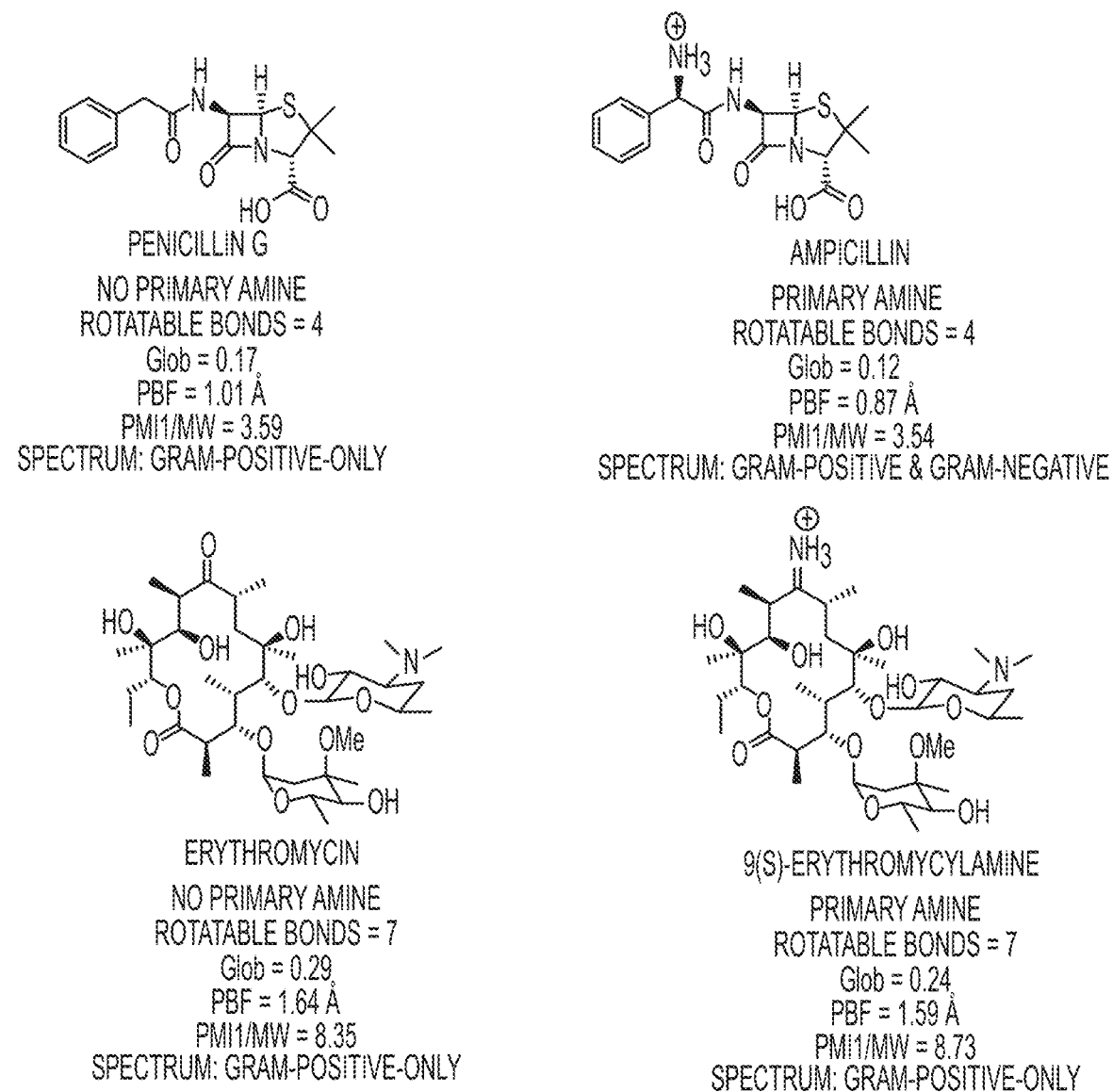
FIG. 16 depicts parameters (e.g., rotatable bonds (RB) and globularity (Glob)) and structures of exemplary antibiotics.

The findings presented here are congruent with what is known about β-lactams and explain why their spectrum could be broadened (e.g. penicillin G to ampicillin) where other classes could not. In both liposome swelling assays and whole cell studies, positive charge greatly accelerates penetration of β-lactams through porins, while negative charge and bulky substituents impede penetration. Indeed, early generation β-lactams lacking an amine, such as penicillin G, are inactive against Gram-negative bacteria. Our analysis shows penicillin G has flexibility/shape parameters (RB=4, Glob=0.17) that make it an outstanding candidate for conversion, and addition of an amine results in ampicillin (RB=4, Glob=0.12), which now meets all criteria for accumulation (structures in FIG. 16). Although there are third and fourth generation β-lactams with Gram-negative activity that do not meet the guidelines outlined here, these β-lactams have greatly reduced accumulation in Gram-negative bacteria compared to their positively-charged analogues that meet the flexibility/shape parameters. However, the third and fourth generation β-lactams are significantly more stable to β-lactamases than the early generation β-lactams, thus requiring lower levels of accumulation for antibacterial activity. As delineated herein, to favor Gram-negative accumulation, a primary amine should be embedded on a compound with proper flexibility and shape parameters; these results explain why simple addition of an amine has not been a generalizable strategy to increase Gram-negative accumulation and activity for other antibiotic classes. As one example from the macrolide class, there are no differences in the spectrum of activity observed for erythromycin versus 9(S)-erythromycylamine; as shown in FIG. 16 these compounds do not possess the appropriate RB and/or Glob parameters for accumulation.

Datasets of chemical structures were created and managed using Canvas (Version 2.6, Schrödinger, LLC, New York, NY, 2015.). Initial structure preparation and 3D minimization was performed with LigPrep (Version 3.6, Schrödinger, LLC, New York, NY, 2015.) using OPLS_2005 force fields. Tautomeric and protonation states were determined using Epik (Version 3.4, Schrödinger, LLC, New York, NY, 2015) at pH 7.4. Generation of ensembles of conformations was performed using Conformational Search in MOE 2015.10 using the LowModeMD method with default settings. Physiochemical descriptors (297, both 2D- and 3D-based) were calculated using MOE for each conformation. Descriptors were averaged (unweighted mean) across all conformations for each molecule. Data with descriptors were used to train a random forest classification prediction model using the R package caret. Preprocessing of data removed descriptors with near zero variance or high co-correlation with other descriptors.

An additional approximation of three-dimensionality, average distance to the plane of best fit (PBF), was calculated using a custom Python program. The PBF algorithm was implemented in Python with SDfile I/O and structure representation being handled by libraries from Schrodinger. For each compound, the PBF algorithm determines the plane that best fits a set of 3D coordinates that represent the positions of all heavy atoms in the molecule using single value decomposition. The distance of each heavy atom to this plane is measured in angstroms and averaged. This Python program was incorporated into the Maestro GUI for convenient use. $ClogD_{7.4}$ were calculated using the online compound property calculation software FAFdrugs.

Example 3—Outer Membrane Protein Profiles

Figure 17A:
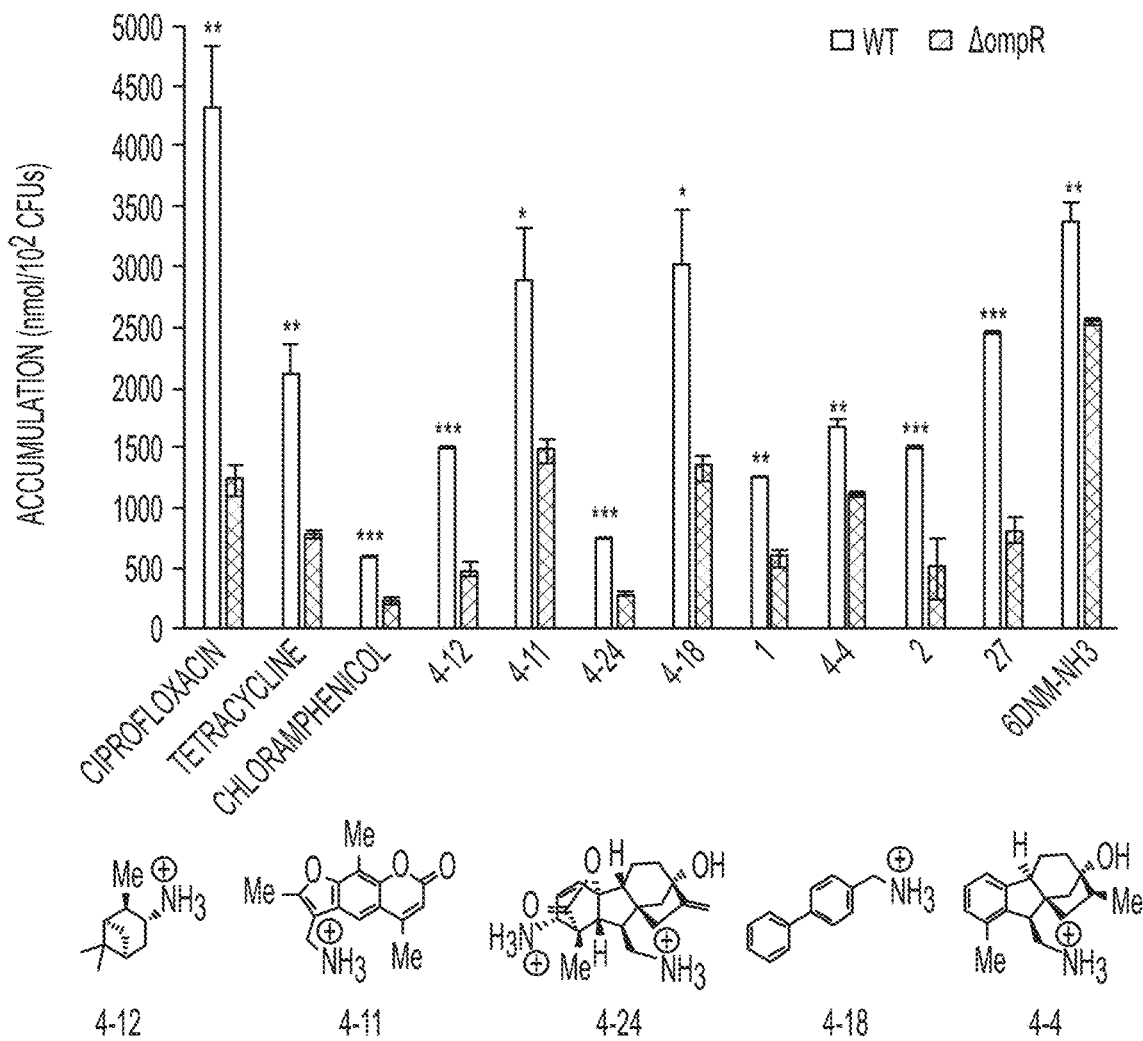
FIG. 17A depicts accumulation of exemplary antibiotics in wild type versus porin knock out bacteria.

As small molecules that traverse the outer membrane of Gram-negative bacteria predominately cross via porins, knocking out the major porins of E. coli would be expected to decrease compound accumulation. While there are many porins present in E. coli, the two major non-specific porins are OmpF and OmpC, which are differentially expressed (based on the extracellular osmolarity) by the EnvZ/OmpR two component regulatory system. A ΔompR strain of E. coli from the KEIO knockout collection was therefore chosen to effectively knockout both OmpF and OmpC (knockout was validated by analyzing the outer membrane proteins of the ΔompR strain compared to the parental strain, data not shown). For control high accumulators ciprofloxacin, tetracycline, and chloramphenicol, a significant decrease in accumulation is observed in the ΔompR strain of E. coli compared to the parental strain E. coli BW25113 (FIG. 17A), consistent with previous data demonstrating that these antibiotics enter through the OmpF and OmpC porins. Eight high accumulating compounds from the test set were also evaluated, and accumulation decreased in the ΔompR strain (FIG. 17B), suggesting these porins are a major gateway to small molecule accumulation for the compounds tested.

The accumulation of 6DNM-NH3 in the ΔompR strain was compared to accumulation in the WT strain of E. coli. A decrease in accumulation is observed, suggesting that OmpF and/or OmpC contribute to 6DNM-NH3 accumulation (Extended Data FIG. 17A).

The method used to compare the outer membrane proteins of E. coli BW25113 to outer membrane of the ΔompR E. coli from the KEIO collection was adapted from Adler, M., Anjum, M., Andersson, D. I. & Sandegren, L. Influence of acquired beta-lactamases on the evolution of spontaneous carbapenem resistance in Escherichia coli. J. Antimicrob. Chemother. 68, 51-59, (2013). Briefly, bacteria were grown to $OD_{600}$=1.0 at 37° C. in LB broth. 4 mL were centrifuged for 10 min at 2,350 g at 4° C., washed with 1 mL of 100 mM Tris-HCl, pH 8.0, with 20% sucrose and incubated on ice for 10 min. Cells were pelleted as before and taken up in 1 mL of 100 mM Tris-HCl, pH 8.0, 20% sucrose containing 10 mM sodium ethylenediaminetetraacetate (EDTA). Lysozyme was added to a final concentration of 100 mg/mL and incubated on ice for 10 min. $MgSO_4$ was added to 20 mM final concentration and RNAseA and DNAseI were added to a final concentration of 10 mg/mL. Cells were disrupted with five freeze-thaw cycles in dry ice/ethanol and room temperature/water bath. A sixth freezing sample was left to thaw on ice for 2 hours. Membranes were pelleted for 25 min at 16,100 g at 4° C. The supernatants were discarded, and the pellet was washed and pelleted three times in 1 mL of 20 mM NaPO$_4$, pH 7 and 0.5% sarkosyl. The protein extracts were taken up in 60 mL of Laemmli sample buffer (80 mM Tris-HCl, pH 6.8, 3% SDS, 10% glycerol, 5% β-mercaptoethanol, 0.02% bromophenol blue), boiled for 5 min and subjected to SDS-PAGE (12% polyacrylamide). Proteins were visualized via staining with Coomassie Blue-G.

Example 4—Accumulation Analysis in Protoplasts

Figure 17B:
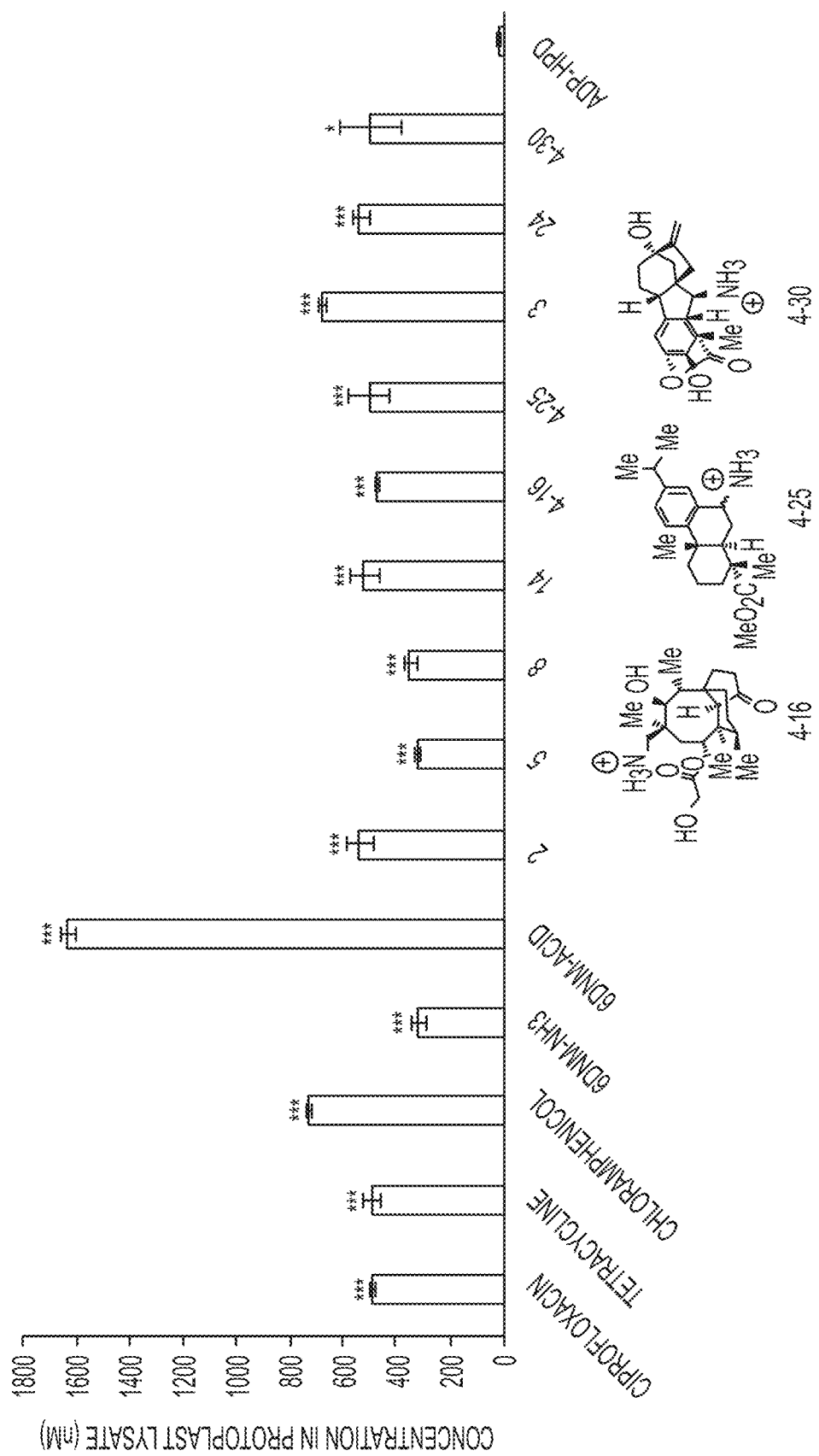
FIG. 17B depicts accumulation in protoplasts of exemplary antibiotics.

A limitation to measuring accumulation in whole cells is that no distinction is made between periplasmic and cytoplasmic accumulation. To reach the cytoplasm of *E. coli* compounds must also diffuse through the inner membrane, whose filtering properties may be different from the filtering properties of the outer membrane. To examine this, high accumulating compounds and some of their derivatives were tested for accumulation in *E. coli* protoplasts, cells lacking the outer membrane and peptidoglycan. As shown in FIG. 17B, minimal variation in accumulation was observed between compounds in this experiment, supporting the hypothesis that traversing the outer membrane is the main barrier to small molecule accumulation in Gram-negative bacteria.

The method for preparing protoplasts was adapted from Weiss. 85 µL of an overnight culture of *E. coli* MG1655 was diluted into 85 mL of fresh LB broth and grown at 37° C. with shaking to an OD$_{600}$=1.0. The bacteria were pelleted at 3,220 rcf for 10 minutes at 4° C. and the supernatant was discarded. The pellet was washed 3 times with 10 mL of 10 mM Tris HCl buffer (pH 8), and the pellet was resuspended in 30 mL of 10 mM Tris HCl (pH 8) containing 0.5 M sucrose. Potassium ethylenediaminetetraacetate (EDTA, 0.5 M, pH 8.0) was added slowly over a period of 20 minutes to a final concentration of 0.01 M. The bacteria were shaken at 130 rpm for 20 minutes at 37° C., and then harvested as before. The supernatant was discarded and the pellets were washed two times with SMM buffer (0.5 M sucrose, 20 mM sodium maleate, 20 mM MgCl$_2$, pH 6.5). The bacteria were then resuspended in 30 mL of SMM buffer, 30 mg of lysozyme was added, and the bacteria were shaken at 130 rpm for 1.5 hour at 37° C. The protoplasts were harvested by centrifuging at 2000 rcf for 20 minutes at 4° C.

The protoplast pellet was resuspended in 20 mL of SMM buffer, and protoplast formation was confirmed by diluting an aliquot in water and observing a 3-fold decrease on OD$_{600}$. To test accumulation, 500 µL aliquots containing 10 µM compound were shaken at 130 rpm for 5 minutes at 37° C. Samples were pelleted at 2000 rcf for 10 minutes at room temperature and the supernatants were discarded. The pellets were resuspended in 200 µL of water and incubated at room temperature for 5 minutes. The lysed protoplasts were pelleted by centrifuging at 21,130 rcf for 10 minutes, and the supernatant was analyzed by LC-MS/MS for compound concentration as before.

Example 5—All-Atom Molecular Dynamics Simulations

Figure 18A:
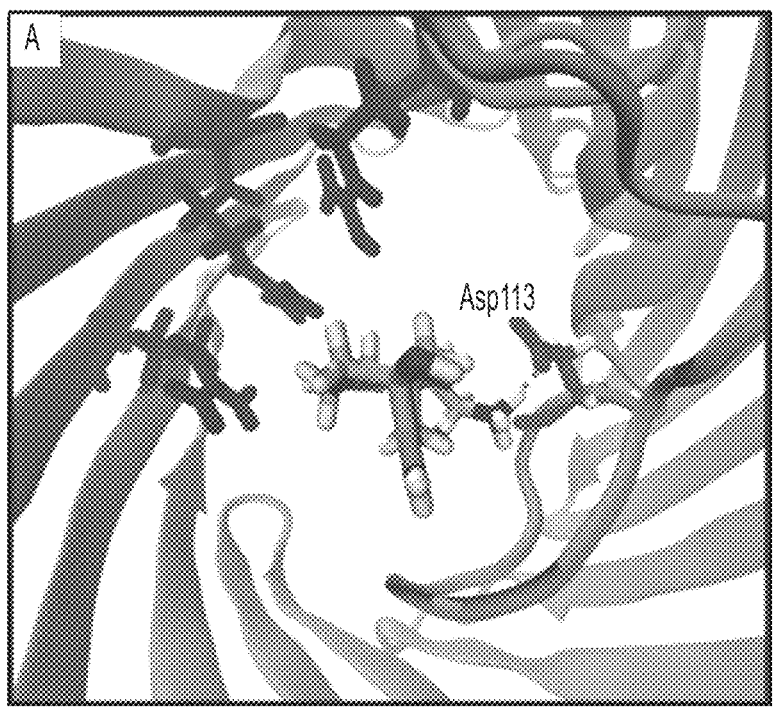
FIG. 18A depicts a snapshot of trajectory with an exemplary compound (Compound 1) showing a key interaction with Asp113 that assists in movement past the porin constriction site.
Figure 18B:
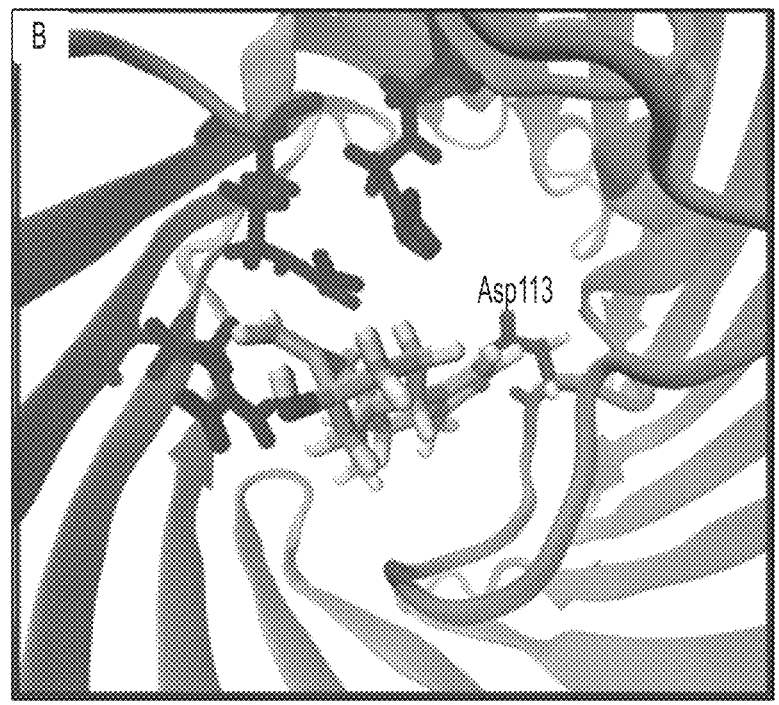
FIG. 18B depicts a snapshot of trajectory with an exemplary compound (Compound 13) without the key interaction with Asp113 in porin.

To better understand the observed accumulation trends, molecular modeling was performed on a subset of test set compounds and antibacterials as they traverse the bacterial porin OmpF. Steered molecular dynamics (SMD) simulations were performed such that molecules were pulled through the constriction site of OmpF. While it does not directly provide the free energy landscape, SMD is frequently employed to map the pathway for long time-scale processes and has been previously utilized to study OmpF. In repeated simulations molecules adopted similar pathways for traversing the porin while often hydrogen bonding with different hydrophilic residues (data not shown). The trajectory of high-accumulating compound 1 reveals a key interaction between the pendant amine and acidic residues (most often Asp113) that assisted in movement through the constriction site (FIG. 19A). This finding is in accord with previous reports of the importance of Asp113 in producing the cation selectivity of OmpF. This interaction was absent in the trajectory of a low-accumulating analogue of 1 (amide 13) (FIG. 18B), in agreement with accumulation data (FIG. 5). Further, amide 13 induces greater distortions in constriction site residues as it is forced through the porin (data not shown).

In addition, SMD simulations were performed with 6DNM and 6DNM-NH3 as these molecules move through the porin OmpF. Similar to SMD simulations in FIG. 18A, the translocation of 6DNM-NH3 was assisted by a key interaction between the primary amine on 6DNM-NH3 and Asp113 (data not shown). 6DNM was incapable of this interaction and instead required distortion in Asp113 and neighboring residues to allow passage (data not shown). Trajectories from SMD clearly suggests 6DNM-NH3 and 6DNM proceed through significantly different pathways.

The simulation model was constructed using CHARMM-GUI and comprised one OmpF monomer (PDB 3POX), 108 (90%) 1-palmitoyl-2-oleoyl-sn-glycero-3-phosphoethanolamine (POPE) lipid molecules, 12 (10%) 1-palmitoyl-2-oleoyl-sn-glycero-3-phospho-(1'-rac-glycerol) (POPG), and solvated with 8,234 water molecules in 150 mM NaCl (36 Na$^+$ and 15 Cl$^-$) for a total of 45,402 atoms. Hexagonal periodic boundary conditions were applied with a distance of 77.3 Å in the XY-direction and 92.8 Å in the Z-direction. Electrostatic interactions were calculated using the Particle-Mesh Ewald (PME) method. Protein residues E296, D312, and D127 were protonated. The simulations were performed at constant pressure (1 atm) and temperature (303 K) with a time step of 2 fs. Each small molecule under investigation was manually placed directly above the pore. Restraints were initially applied to protein backbone and small molecule analyte atoms and then removed to equilibrate the system. For SMD production simulations, each small molecule analyte was pulled at the molecules center of mass (5 kcal/mol Å$^2$) at a constant velocity (10 Å/ns) along the Z-axis for 4 ns. The all-atom CHARMM force field was used for protein and lipids. TIP3P was used for water. All the MD simulations were carried out using the NAMD 2.11 scalable molecular dynamics program and run on Stampede at TACC. CHARMM residue topology and parameter files for the small molecules were constructed using CGenFF. SMD trajectories were analyzed and visualized using VMD 1.9.2 and rendered using Pov-Ray 3.6.

Example 6—Design of Novel Compounds

The natural product deoxynybomycin (DNM) was selected as a good candidate for conversion to a broad-spectrum agent. DNM has antibacterial activity through inhibition of wild-type and mutant DNA gyrase, and DNM and its alkyl-chain derivatives are only active against Gram-positive bacteria. Chemoinformatic analysis shows that DNM has zero rotatable bonds and a Glob of 0.02, suggesting that the addition of an amine to a position that does not alter the DNM antibacterial activity would provide a derivative able to accumulate in and be active against Gram-negative pathogens. To facilitate construction of a derivative with a primary amine, an analogue of DNM was first synthesized where the five-membered ring in DNM is expanded to a six-membered ring, affording the compound 6DNM (structures in Table 1 of FIG. 19; all synthetic routes can be found in Example 6 below). Assessment with the accumulation assay reveals 6DNM has low accumulation in E. coli (298 nmol/$10^{12}$ CFUs) (Table 1 of FIG. 19).

A derivative of 6DNM was then designed that maintains low RB and Glob, but that also contains a primary amine; this compound is named 6DNM-NH3 and its structure is shown in Table 1 of FIG. 19. Synthesis of 6DNM-NH3 followed by antibacterial evaluation reveals that this compound retains activity against S. aureus, but it also accumulates in E. coli to a high degree (1114 nmol/$10^{12}$ CFUs). Consistent with this enhanced accumulation, 6DNM-NH3 shows significant activity against E. coli MG1655 (MIC=0.5 μg/mL). Similar to observed patterns of accumulation from the test compounds, when the amine of 6DNM-NH3 is acetylated or replaced with a carboxylic acid, the resulting compounds (6DNM-amide and 6DNM-acid) do not accumulate in E. coli (Table 1 of FIG. 19).

Example 7—Antibiotic Susceptibility Tests

6DNM is active against *Staphylococcus aureus* (MIC=0.06-1 μg/mL) but shows no activity versus E. coli (MIC>32 μg/mL, Table 1 of FIG. 19). Synthesis of 6DNM-NH3 followed by antibacterial evaluation reveals that this compound retains activity against S. aureus, but it also accumulates in E. coli to a high degree (1114 nmol/$10^{12}$ CFUs). Consistent with this enhanced accumulation, 6DNM-NH3 shows significant activity against E. coli MG1655 (MIC=0.5 μg/mL). When the amine of 6DNM-NH3 is acetylated or replaced with a carboxylic acid, the resulting compounds (6DNM-amide and 6DNM-acid) show no activity against E. coli (Table 1 of FIG. 19). 6DNM and its derivatives were further evaluated against an expanded panel of Gram-negative pathogens, laboratory strains and clinical isolates of ESKAPE pathogens E. coli, Acinetobacter baumannii, Klebsiella pneumoniae, Enterobacter cloacae, and Pseudomonas aeruginosa (Table 1 of FIG. 19). While 6DNM possesses no notable activity against these Gram-negative organisms, 6DNM-NH3 has antibacterial activity against all of these Gram-negative pathogens except P. aeruginosa. Encouragingly, 6DNM-NH3 possesses activity against a multi-drug resistant New Delhi metallo-β-lactamase-1 producing strain of E. coli (ATCC BAA-2469[48]); this clinical isolate is highly resistant to ciprofloxacin (MIC>64 μg/mL, Table 1 of FIG. 19) and many other antibiotics but is killed by 6DNM-NH3 with an MIC of 4 μg/mL (Table 1 of FIG. 19). 6DNM-NH3 also maintains good activity against most of the other clinical isolates of E. coli, A. baumannii, K. pneumonia, and E. cloacae (Table 1 of FIG. 19).

Susceptibility testing was performed in triplicate, using the microdilution broth method as outlined by the Clinical and Laboratory Standards Institute. Mueller Hinton (MH) broth was used.

Example 8—Synthesis of Novel Compounds

General Reagent Information

Chemical reagents were purchased from commercial sources and used without further purification. Anhydrous solvents used during these studies were dried after being passed through columns with activated alumina. Various 2-D NMR experiments were conducted as necessary. $^1$H NMR and $^{13}$C NMR experiments were recorded on Varian Unity spectrometers at either 400 MHz, 500 MHz, or 750 MHz, and 125 MHz or 188 MHz, respectively. Spectra were obtained in the following solvents (reference peaks also included for $^1$H and $^{13}$C NMRs): CDCl$_3$ (1H NMR: 7.26 ppm; $^{13}$C NMR: 77.26 ppm), d$_6$-acetone ($^1$H NMR: 2.05 ppm; $^{13}$C NMR: 206.26 ppm), CD$_3$OD ($^1$H NMR: 3.30 ppm; $^{13}$C NMR: 49.00 ppm), d$_7$-DMF ($^1$H NMR: 2.75 ppm; $^{13}$C NMR: 34.90 ppm) D$_2$O ($^1$H NMR: 4.79 ppm) d$_6$-DMSO ($^1$H NMR: 2.50 ppm; $^{13}$C NMR: 39.52 ppm). NMR experiments were performed at room temperature unless otherwise indicated. Chemical shift values are reported in parts per million (ppm) for all $^1$H NMR and $^{13}$C NMR spectra. $^1$H NMR multiplicities are reported as: s=singlet, d=doublet, t=triplet, q=quartet, m=multiplet, br=broad.

Various novel compounds were synthesized.

Exemplary Pleuromutilin Derivatives

General Procedure A for Pleuromutilin Derivatives

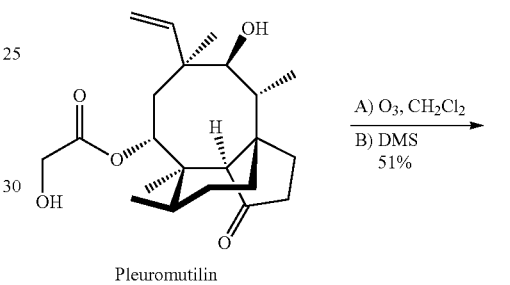

Pleuromutilin

Precursor A for 4-16

A solution of pleuromutilin (1.0 g, 2.6 mmol) in dichloromethane was cooled to −78° C. and a stream of ozone was passed through the reaction mixture until a blue color persisted (12 minutes). The reaction mixture was then purged with oxygen, dimethyl sulfide (0.57 mL, 7.8 mmol) was added, and the reaction was allowed to warm to room temperature while stirring for 24 hours. The crude reaction mixture was washed with brine, extracted with dichloromethane, and the combined organic layers were dried with magnesium sulfate and evaporated. Purification by flash chromatography (2:1 ethyl acetate:hexanes) provided precursor A to 4-16 (503 mg, 51%) as a white solid.

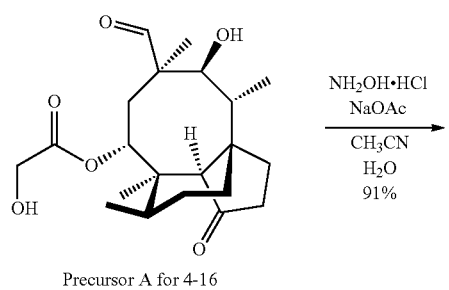

Precursor A for 4-16

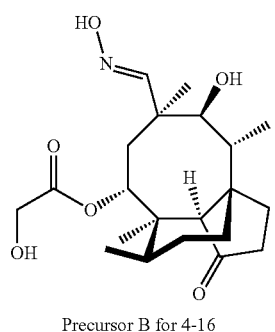

Precursor B for 4-16

Precursor A for 4-16 (450 mg, 1.18 mmol), hydroxylamine hydrochloride (164 mg, 2.36 mmol), and sodium acetate (387, 4.72 mmol) were dissolved in acetonitrile (11.8 mL) and water (2.95 mL) and heated to 50° C. in a sealed vial for 6 hours. The reaction mixture was then cooled to room temperature, diluted with water and extracted with ethyl acetate. The combined organic layers were washed with brine, dried with magnesium sulfate, and evaporated. Purification by flash chromatography (2:1 ethyl acetate:hexanes) provided precursor B for 4-16 (425 mg, 91%) as a white solid.

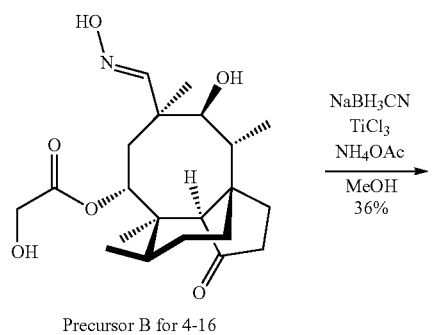

4-16

To a solution of precursor B for 4-16 (372 mg, 0.96) and ammonium acetate (296, 3.84 mmol) in methanol at room temperature was added sodium cyanoborohydride (241 mg, 3.84 mmol). The reaction mixture was then cooled to 0° C., a solution of titanium trichloride (~10 wt. % TiCl₃ in 20-30 wt. % HCl, 0.96 mL) was then added dropwise, and the reaction was stirred for 24 hours while warming to room temperature. The reaction was quenched by addition of 2 M sodium hydroxide and extracted with dichloromethane. The combined organic layers were washed with brine, dried with magnesium sulfate, and evaporated. Purification by flash chromatography (15% methanol and 2% triethylamine in dichloromethane) provided amine 4-16 (134 mg, 36%) as a white solid.

$^1$H NMR (CD3OD, 500 MHz): δ 5.60 (d, J=8.7 Hz, 1H), 4.06 (d, J=17.1 Hz, 1H), 3.98 (d, J=16.9 Hz, 1H), 3.53 (dd, J=15.8, 6.4 Hz, 1H), 3.24-3.16 (m, 1H), 2.78-2.73 (m, 1H), 2.45-2.37 (m, 1H), 1.96-1.86 (m, 2H), 1.82 (dq, J=13.8, 3.0 Hz, 1H), 1.71-1.47 (m, 3H), 1.43 (s, 3H), 1.40-1.35 (m, 1H), 1.27 (t, J=7.3 Hz, 1H), 1.22-1.14 (m, 2H), 1.13 (s, 3H), 1.12-1.07 (m, 2H), 0.98 (d, J=7.1 Hz, 3H), 0.97-0.93 (m, 2H), 0.72 (d, J=6.9 Hz, 3H). (33-nonexchangeable protons).

$^{13}$C NMR (CD3OD, 125 MHz): δ 219.72, 173.80, 76.90, 70.38, 61.91, 58.32, 46.62, 45.50, 43.01, 42.85, 42.33, 37.99, 36.72, 31.54, 28.18, 25.99, 25.43, 18.38, 17.31, 15.16, 11.93.

General Procedure B for Pleuromutilin Derivatives

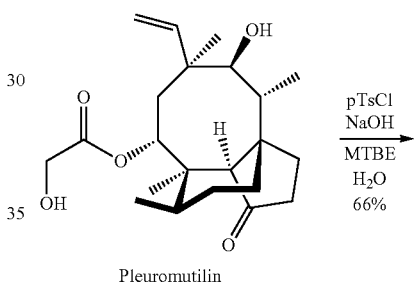

Pleuromutilin

Precursor to 4-57

To a solution of pleuromutilin (757 mg, 2 mmol) and p-tosyl chloride (763 mg, 4 mmol) in methyl t-butyl ether (2 mL) and water (0.5 mL) was added a solution of 10 M sodium hydroxide (0.5 mL) dropwise. The reaction mixture was then heated to reflux for 1 hour, cooled to room temperature, diluted with water, and extracted with ethyl acetate. The combined organic layers were washed with brine, dried with magnesium sulfate, and evaporated. Purification by flash chromatography (2:3 ethyl acetate:hexanes) provide the precursor to 4-57 (706 mg, 66%) as a white solid.

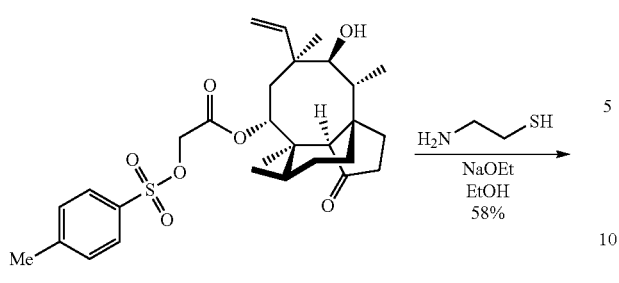

Precursor to 4-57

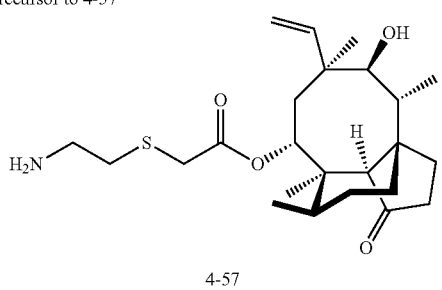

4-57

To a solution of cysteamine hydrochloride (9 mg, 0.11 mmol) in ethanol (903 µL) at room temperature was added a solution of sodium ethoxide (97 µL, 0.26 mmol, 21% in ethanol) and the mixture was stirred for 30 minutes. The solution was then cooled to 0° C., the precursor to 4-57 (53 mg, 0.1 mmol) was added, and the reaction was stirred at 0° C. for 3.5 hours. The crude reaction mixture was then warmed to room temperature diluted with water and extracted with ethyl acetate. The combined organic layers were washed with brine, dried with magnesium sulfate, and evaporated. Purification by flash chromatography (10% methanol and 2% triethylamine in ethyl acetate) provided 4-57 (25 mg, 58%) as a white solid.

$^1$H-NMR (CD3OD, 500 MHz): δ 6.32 (dd, J=17.5, 11.2 Hz, 1H), 5.74 (d, J=8.3 Hz, 1H), 5.35-5.03 (m, 2H), 3.50 (d, J=6.2 Hz, 1H), 3.29-3.19 (m, 2H), 2.97-2.89 (m, 2H), 2.78 (td, J=6.6, 3.1 Hz, 2H), 2.41-2.37 (m, 1H), 2.37-2.22 (m, 2H), 2.23-2.11 (m, 2H), 1.82 (dq, J=14.1, 2.9 Hz, 1H), 1.75-1.52 (m, 3H), 1.52-1.41 (m, 4H), 1.42-1.33 (m, 2H), 1.26-1.17 (m, 1H), 1.16 (s, 3H), 1.14-1.05 (m, 1H), 0.94 (d, J=7.0 Hz, 3H), 0.74 (d, J=6.7 Hz, 3H). (37 non-exchangeable protons).

$^{13}$C-NMR (CD3OD, 125 MHz, 60° C.): δ 219.6, 170.7, 141.3, 116.5, 75.4, 71.3, 59.3, 46.8, 46.0, 45.3, 43.1, 40.6, 38.2, 37.7, 35.3, 34.9, 34.7, 31.5, 28.2, 28.0, 25.8, 17.1, 15.4, 11.8.

HRMS(ESI): m/z calc. for $C_{24}H_{40}NO_4S$ [M+H]+: 438.2678, found: 438.2680.

Exemplary Deoxynybomycin Derivatives
General Procedure A for Deoxynybomycin Derivatives

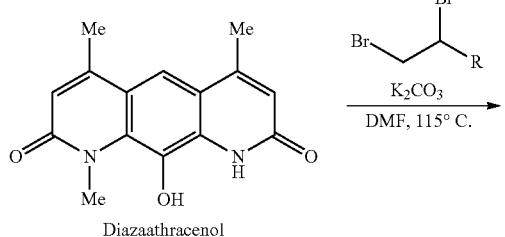

Diazaathracenol

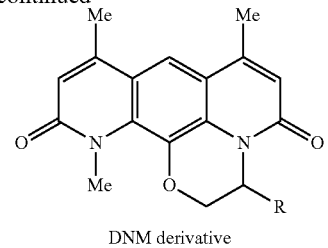

DNM derivative

A flame-dried flask was charged with diazaanthracenol, prepared as previously described (45, 46), and N,N-dimethylformamide (35 mM) then warmed to 115° C. under an atmosphere of nitrogen. The resulting solution was treated sequentially with potassium carbonate (10.0 equiv) and appropriate dibromide (2.0 equiv). An additional equivalent of dibromide was added after 1 hour, 2 hours, and 3 hours. The reaction was monitored by thin layer chromatography (TLC) and upon completion (5-8 h) was cooled to room temperature then diluted with chloroform (30 mL) and water (50 mL). The aqueous layer was further extracted with chloroform (4×30 mL). The combined organic layers were dried over sodium sulfate and concentrated in vacuo. The resulting residue was purified by silica gel chromatography (90-100% ethyl acetate/hexanes).

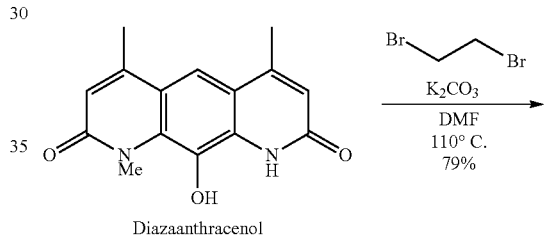

Diazaanthracenol

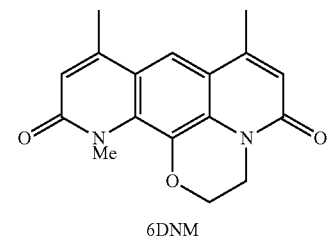

6DNM

Synthesized from diazaanthrecol (30.6 mg, 0.113 mmol) and 1,2-dibromoethane according to General Procedure A to yield 6DNM as a white solid (26.4 mg, 79% yield).

$^1$H NMR (CDCl3, 500 MHz): δ 7.52 (s, 1H), 6.52 (d, J=1.7 Hz, 2H), 4.38 (t, J=4.7 Hz, 2H), 4.27 (t, J=4.7 Hz, 2H), 3.91 (s, 3H), 2.49 (d, J=1.2 Hz, 3H), 2.5 (d, J=1.18 Hz, 3H).

$^{13}$C NMR (CDCl3, 125 MHz): δ 163.36, 160.25, 146.52, 145.65, 131.11, 130.79, 127.72, 120.65, 119.72, 118.41, 116.77, 113.79, 63.59, 39.83, 35.29, 19.19, 18.97.

HRMS (ESI): m/z calc. for C17H17N2O3 [M+H]+: 297.1239, found: 297.1236.

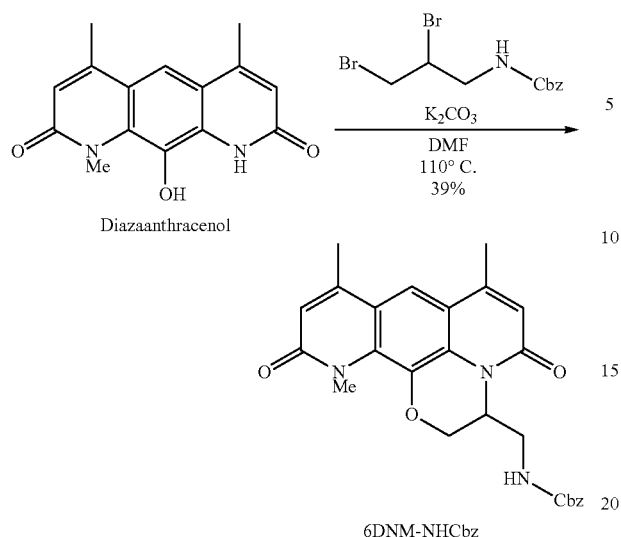

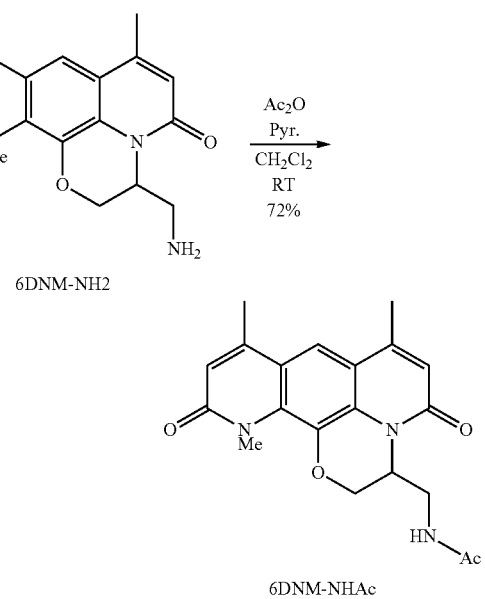

Synthesized from diazaanthrecol (45 mg, 0.166 mmol) and benzyl (2,3-dibromopropyl)carbamate (according to General Procedure A to yield 6DNM-NHCbz as a white solid (30.1 mg, 39% yield).

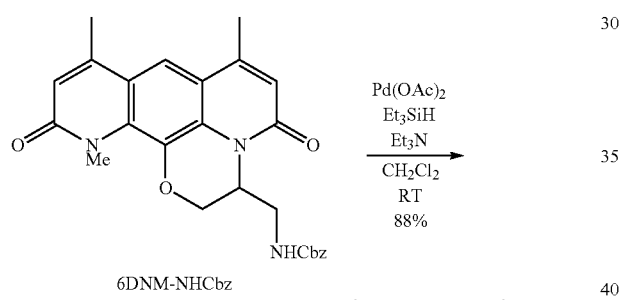

A flame-dried flask was charged with Pd(OAc)$_2$ (25.6 mg, 0.114 mmol) and dichloromethane (10 mL) under an atmosphere of nitrogen. The resulting solution was treated sequentially with Et$_3$SiH (0.27 mL, 1.7 mmol) and triethylamine (32 µL, 0.23 mmol). After stirring for 15 min, 1.0 mL of the black solution was transferred to a solution of DNM-NHCbz (26.2 mg, 0.0570 mmol) in dichloromethane under an atmosphere of nitrogen. After stirring at room temperature for 24 hours, the reaction was quenched with methanol (2 mL) and saturated NH$_4$OH (20 µL) and stirred for an additional 30 minutes. The solvent was removed in vacuo and the resulting residue was purified by silica gel chromatography (0-8% methanol/chloroform) to produce 6DNM-NH$_3$ as an off white solid (16.5 mg, 88%).

A flame-dried flask was charged with 6DNM-NH$_3$ (10.0 mg, 0.0307 mmol) was dissolved in a mixture of dichloromethane (2 mL) and pyridine (2 mL) under an atmosphere of nitrogen. The resulting solution was treated with acetic anhydride (7.6 µL, 0.054 mmol.). After stirring at room temperature for 2 hours, the reaction as diluted with dichloromethane (25 mL) and 3 M HCl (25 mL). The layers were separated and the aqueous layer extracted with additional dichloromethane (2×25 mL). The combined organic layers were washed with brine (30 mL), dried over sodium sulfate and concentrated in vacuo. The resulting residue was purified by silica gel chromatography eluting (0-5% methanol/dichloromethane) to yield 6DNM-NHAc as an off-white solid (8.1 mg, 72%).

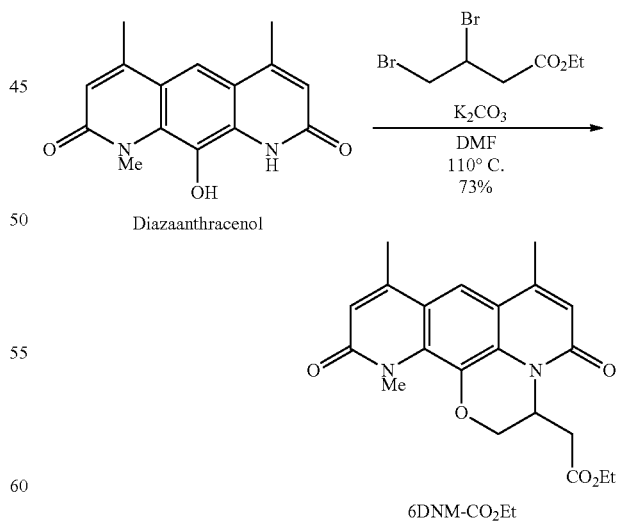

Synthesized from diazaanthrecol (30.0 mg, 0.111 mmol) and ethyl 3,4-dibromobutanoate (53) according to General Procedure A to yield 6DNM-CO$_2$Et as a white solid (31.0 mg, 73% yield).

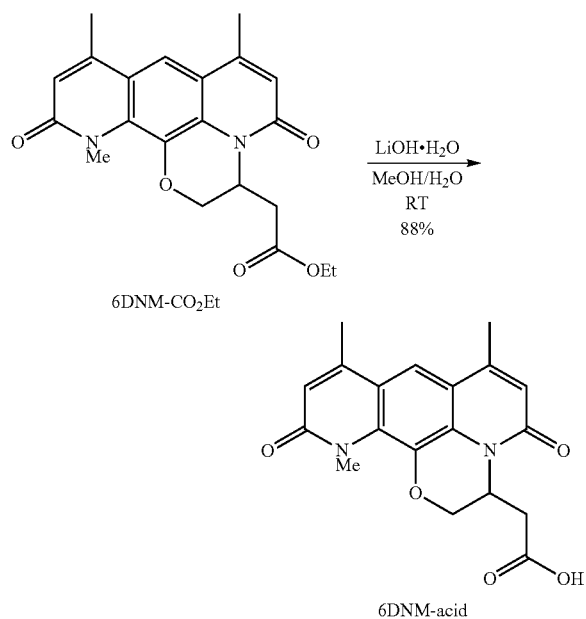

6DNM-CO₂Et

6DNM-acid

A flask was charged with 6DNM-CO₂Et (31.0 mg, 0.0811 mmol) and methanol (6 mL). The resulting solution was treated with concentrated aqueous lithium hydroxide (0.60 mL) at room temperature. After stirring for 4 hours, the solvent was removed in vacuo and the resulting residue redissolved in water (30 mL) and passed through a syringe filter. The solution was acidified with 6 M HCl and extracted with chloroform (5×25 mL). The combined organic layers were dried over sodium sulfate and concentrated in vacuo to yield 6DNM-acid as a white solid (25.2 mg, 88%).

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A compound represented by Formula (IX) or a pharmaceutically acceptable salt thereof:

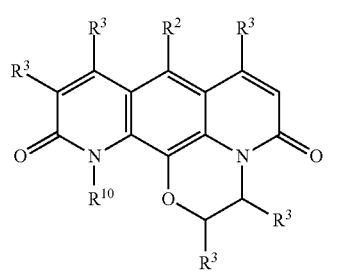

(IX)

wherein, independently for each occurrence:

$R^2$ is selected from the group consisting of hydrogen, halogen, —CN, $(C_1-C_6)$alkyl optionally substituted with 1, 2, or 3 halogen atoms, cycloalkyl, heterocycloalkyl, aryl, heteroaryl, aralkyl, heteroaralkyl, —C(O)OR⁵, —OR⁵, —SR⁵, —S(O)R⁵, —SO₂R⁵, —SO₂NR⁵, —NO₂, —N₃, and —N(R⁵)ₘ;

$R^3$ is selected from the group consisting of hydrogen, halogen, —CN, $(C_1-C_6)$alkyl optionally substituted with 1, 2, or 3 halogen atoms, —(($C_1$-$C_6$)alkylene)N(R⁵)ₘ, —C(O)(($C_1$-$C_6$)alkylene)N(R⁵)ₘ, cycloalkyl, heterocycloalkyl, aryl, heteroaryl, aralkyl, heteroaralkyl, —C(O)OR⁵, —OR⁵, —O(($C_1$-$C_6$)alkylene)N(R⁵)ₘ, —SR⁵, —S(O)R⁵, —SO₂R⁵, —SO₂NR⁵, —NO₂, —N₃, and —N(R⁵)ₘ;

$R^5$ is selected from the group consisting of hydrogen, $(C_1-C_6)$alkyl optionally substituted with 1, 2, or 3 halogen atoms, cycloalkyl, heterocycloalkyl, aryl, heteroaryl, aralkyl, and heteroaralkyl;

$R^{10}$ is selected from the group consisting of $(C_1-C_6)$alkyl, cycloalkyl, heterocycloalkyl, aryl, heteroaryl, aralkyl, and heteroaralkyl; and m is 2 or 3; and provided that at least one of $R^2$ or $R^3$ comprises a terminal —N(R⁵)ₘ.

2. The compound of claim 1 wherein, independently for each occurrence:

$R^2$ is selected from the group consisting of hydrogen, halogen, $(C_1-C_6)$alkyl, —OR⁵, and —N(R⁵)ₘ;

$R^3$ is selected from the group consisting of hydrogen, $(C_1-C_6)$alkyl, —(($C_1$-$C_6$)alkylene)N(R⁵)ₘ, —C(O)(($C_1$-$C_6$)alkylene)N(R⁵)ₘ, —OR⁵, and —N(R⁵)ₘ;

$R^5$ is hydrogen or $(C_1-C_6)$alkyl;

$R^{10}$ is $(C_1-C_6)$alkyl or cycloalkyl; and m is 2 or 3.

3. The compound of claim 1 wherein $R^2$ is hydrogen.

4. The compound of claim 1 wherein $R^3$ is selected from the group consisting of hydrogen, $(C_1-C_6)$alkyl, —(($C_1$-$C_6$)alkylene)N(R⁵)ₘ, and —N(R⁵)ₘ; and $R^5$ is hydrogen or $(C_1-C_6)$alkyl.

5. The compound of claim 1 wherein the compound of formula (IX) is represented by Formula (IXa) or a pharmaceutically acceptable salt thereof:

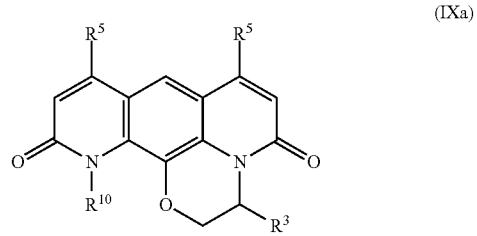

(IXa)

wherein, independently for each occurrence:

$R^3$ is —(($C_1$-$C_6$)alkylene)N(R⁵)ₘ or —N(R⁵)ₘ;

$R^5$ is hydrogen or $(C_1-C_6)$alkyl;

$R^{10}$ is $(C_1-C_6)$alkyl or cycloalkyl; and m is 2 or 3.

6. The compound of claim 1 selected from the group consisting of:
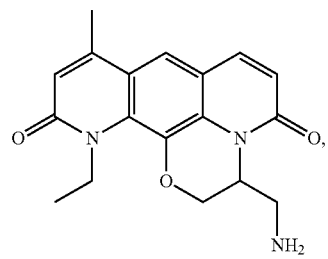
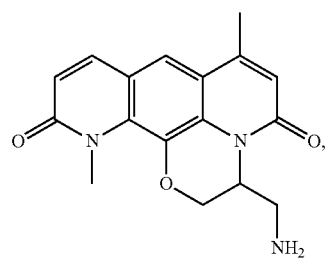
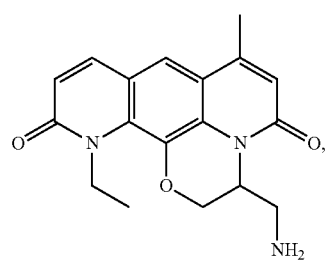
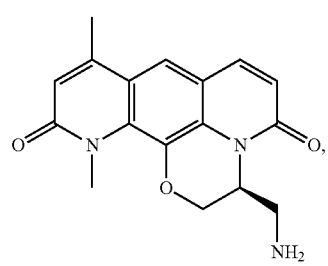
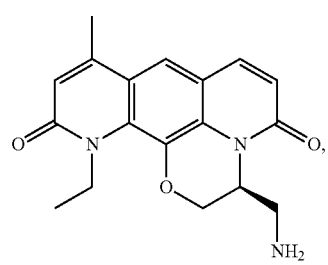
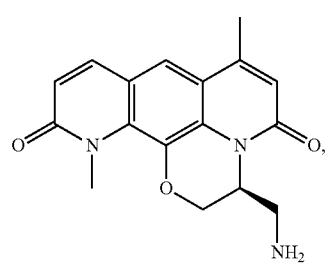
-continued
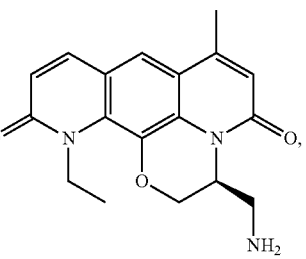
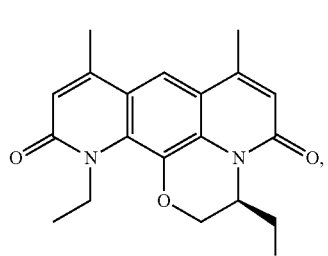
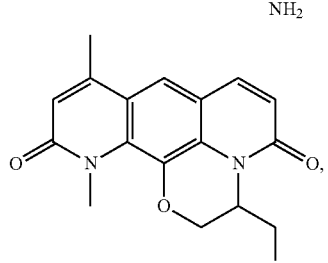
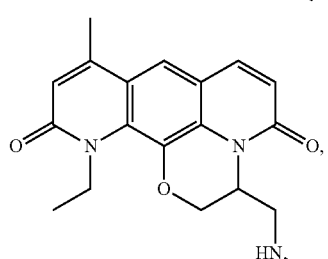
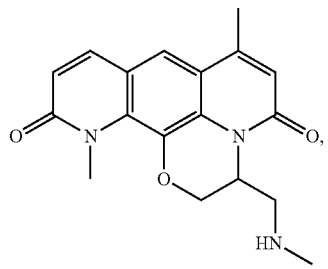
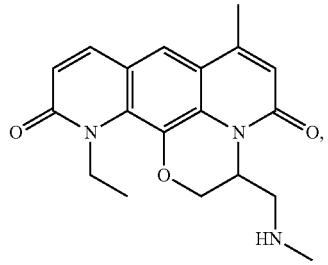

-continued
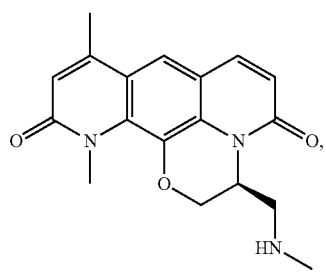
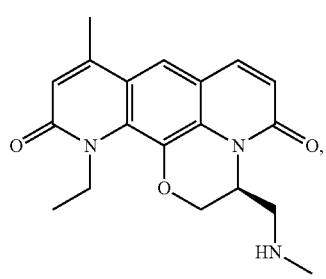
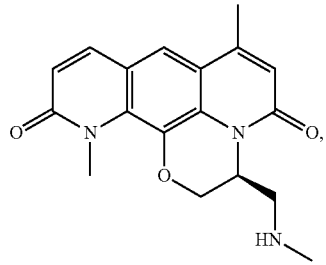
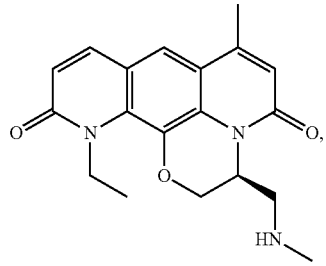
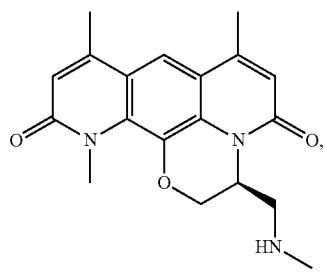
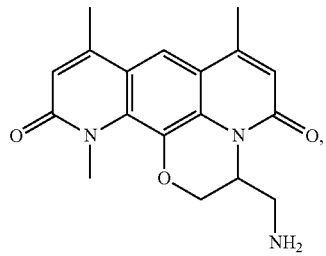
-continued
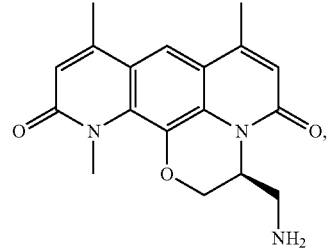
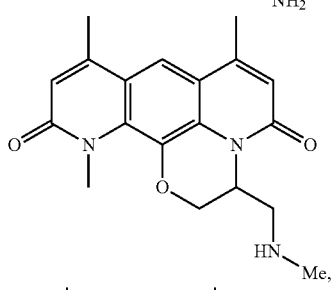
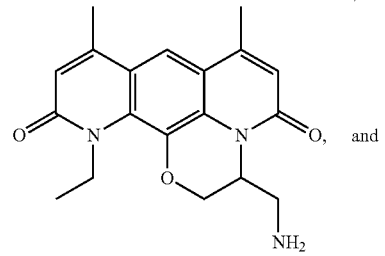
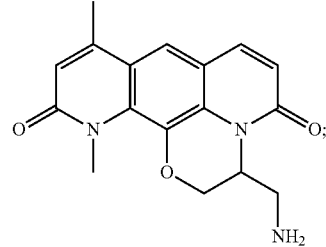
or a pharmaceutically acceptable salt thereof.
7. The compound of claim 6 selected from the group consisting of:
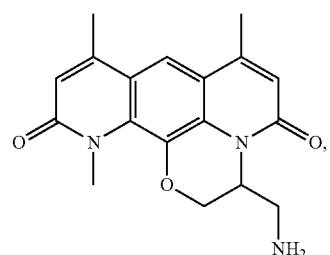
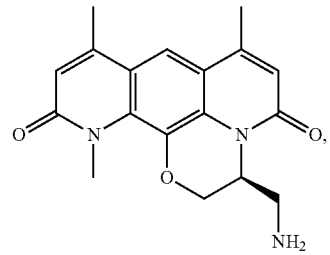

127
-continued

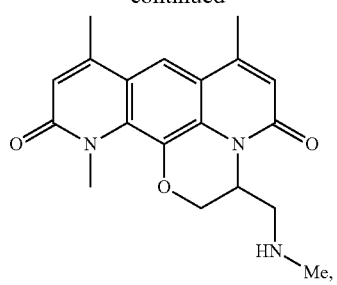

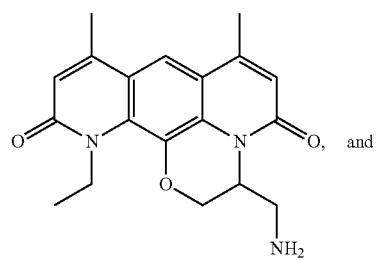

128
-continued

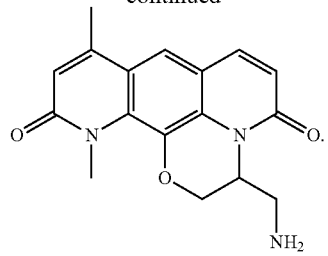

8. A method of antimicrobial treatment, comprising, administering to a subject in need thereof a therapeutically effective amount of a compound of claim 1 or a pharmaceutically acceptable salt thereof,
thereby killing or inhibiting the growth of at least a portion of a plurality of microorganisms in the subject.

9. A method of antimicrobial treatment, comprising:
providing a sample comprising a plurality of microorganisms;
contacting the sample with a compound of claim 1;
thereby killing or inhibiting the growth of at least a portion of the plurality of microorganisms in the sample.

* * * * *